US008044028B2

(12) United States Patent
Moussou et al.

(10) Patent No.: US 8,044,028 B2
(45) Date of Patent: Oct. 25, 2011

(54) OLIGOPEPTIDES AND THEIR USE IN COSMETICS

(75) Inventors: Philippe Moussou, Tomblaine (FR); Louis Danoux, Saulxures les Nancy (FR); Gilles Pauly, Nancy (FR); Jean-Luc Contet-Audonneau, Saint-Max (FR)

(73) Assignee: Cognis France S.A.S., Boussens (FR)

( * ) Notice: Subject to any disclaimer, the term of this patent is extended or adjusted under 35 U.S.C. 154(b) by 1194 days.

(21) Appl. No.: 11/665,810

(22) PCT Filed: Oct. 10, 2005

(86) PCT No.: PCT/EP2005/010893
§ 371 (c)(1),
(2), (4) Date: Apr. 18, 2007

(87) PCT Pub. No.: WO2006/042661
PCT Pub. Date: Apr. 27, 2006

(65) Prior Publication Data
US 2010/0137560 A1    Jun. 3, 2010

(30) Foreign Application Priority Data
Oct. 18, 2004  (EP) .................................... 04292475

(51) Int. Cl.
*A61K 38/00* (2006.01)
(52) U.S. Cl. ..................................................... 514/18.8
(58) Field of Classification Search ........................ None
See application file for complete search history.

(56) References Cited

U.S. PATENT DOCUMENTS

| 4,966,848 | A | * | 10/1990 | Smith et al. .................... 435/193 |
| 5,223,421 | A | * | 6/1993 | Smith et al. .................... 435/193 |
| 5,837,218 | A | * | 11/1998 | Peers et al. .................... 424/1.69 |
| 6,713,605 | B1 | | 3/2004 | Blecha et al. |
| 2005/0142092 | A1 | * | 6/2005 | Lintner ....................... 424/70.14 |

FOREIGN PATENT DOCUMENTS

| DE | 197 56 377 | 6/1999 |
| FR | 74 39242 | 11/1974 |
| WO | WO 00/43417 | 7/2000 |
| WO | WO 00/57895 | 10/2000 |
| WO | WO 01/30368 | * 5/2001 |
| WO | WO 01/47540 | 7/2001 |
| WO | WO 03/037933 | 5/2003 |
| WO | WO 03/042387 | 5/2003 |
| WO | WO 03/068141 | 8/2003 |
| WO | WO 2004/033668 | 4/2004 |
| WO | WO 2006/042661 | 4/2006 |

OTHER PUBLICATIONS

Gaczynska, M., et al, "Proline- and arginine-rich peptides constitute a novel class of allosteric inhibitors of proteasome activity," Biochemistry (2003), 42(29), 8663-8670.*
Chan R.Y. and Gallo R.L.: "PR-39, a Syndecan-inducing Antimicrobial eptide, Binds and Affects p130$^{Cas}$" J. Biol Chem, vol. 273, No. 44, Oct. 30, 1998, pp. 28978-28985, XP-002322010.
Gallo R.L. et al: "Syndecans, cell surface heparan sulfate proteoglycans, are induced by a proline-rich antimicrobial peptide from wounds." Proceedings of the National Academy of Sciences of the United States of America. Nov. 8, 1994, vol. 91, No. 23, Nov. 8, 1994, pp. 11035-11039, XP001022264 ISSN: 0027-8424.
Gaczynska Maria et al: "Proline- and Arginine-Rich Peptides Constitute a Novel Class of Allosteric Inhibitors of Proteasome Activity" Biochemistry, American Chemical Society, Easton, PA, US, vol. 42, No. 29, Jul. 29, 2003, pp. 8663-8670, XP002276092 ISSN: 0006-2960.
Chan Y R, Zanetti M, Gennaro R, Gallo RL: "Anti-Microbial Activity and Cell Binding are Controled by Sequence Determinants in the Anti-Microbial Peptide PR-39" J. Invest.Dermat., vol. 116, No. 2, Feb. 2, 2001, pp. 230-235, XP009045423.
Zaiou M and Gallo RL: "Cathelicidins, essential gene-encoded mammalian antibiotics" J Mol Med, vol. 80, 2002, pp. 549-561, XP009045301.
Gudmundsson G, Magnusson K.P., Chowdhary B.P., Johansson M., Andersson L., Boman H.G.: "Structure of the gene for porcine peptide antiobiotic PR-39, a cathelin gene family member: Comparative mapping of the locus for the human peptide anti biotic FALL-39" Proc. Natl.Acad.Sci USA, vol. 92, Jul. 1995, pp. 7085-7089.
Gallo, R.L. & Huttner K.M., J. Invest. Dermatol. 1998, 111, 739-43 "Antimicrobial Peptides: An Emerging Concept in Cutaneous Biology".
R. Lockhhead et al., "Encyclopedia of Polymers and Thickeners for Cosmetics", Cosmetics & Toiletries, vol. 108, (May 1993), pp. 95-114, 116-124, 127-130, 132-135.
"Kosmetische Färbemittel", Farbstoffkommission der Deutschen Forschungsgemeinschaft, Verlag Chemie, Weinheim, (1984), pp. 81-106.

* cited by examiner

*Primary Examiner* — Cecilia J Tsang
*Assistant Examiner* — Thomas Heard
(74) *Attorney, Agent, or Firm* — Fox Rothschild LLP

(57) ABSTRACT

The present invention relates to the cosmetic use of oligopeptides, cosmetic preparations which comprise such oligopeptides as well as certain oligopeptide derivatives themselves.

11 Claims, No Drawings

SEQUENCE LISTING

<160> NUMBER OF SEQ ID NOS: 375

<210> SEQ ID NO 1
<211> LENGTH: 39
<212> TYPE: PRT
<213> ORGANISM: Artificial
<220> FEATURE:
<223> OTHER INFORMATION: peptide derived from cathelicidin PR-39

<400> SEQUENCE: 1

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Glu Phe Pro Pro
            20                  25                  30

Arg Phe Pro Pro Arg Phe Pro
        35

<210> SEQ ID NO 2
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 2

Arg Arg Arg Pro
1

<210> SEQ ID NO 3
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 3

Arg Arg Pro Arg
1

<210> SEQ ID NO 4
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 4

Arg Pro Arg Pro
1

<210> SEQ ID NO 5
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 5

Pro Arg Pro Pro
1

<210> SEQ ID NO 6
<211> LENGTH: 4
<212> TYPE: PRT
<213> ORGANISM: Artificial

<220> FEATURE:
<223> OTHER INFORMATION: peptide derived from cathelicidin PR-39

<400> SEQUENCE: 6

Arg Pro Pro Tyr
1

<210> SEQ ID NO 7
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 7

Pro Pro Tyr Leu
1

<210> SEQ ID NO 8
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 8

Pro Tyr Leu Pro
1

<210> SEQ ID NO 9
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 9

Tyr Leu Pro Arg
1

<210> SEQ ID NO 10
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 10

Leu Pro Arg Pro
1

<210> SEQ ID NO 11
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 11

Pro Arg Pro Arg
1

<210> SEQ ID NO 12
<211> LENGTH: 4
<212> TYPE: PRT
<213> ORGANISM: Artificial
<220> FEATURE:
<223> OTHER INFORMATION: peptide derived from cathelicidin PR-39

-continued

```
<400> SEQUENCE: 12

Arg Pro Arg Pro
1

<210> SEQ ID NO 13
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 13

Pro Arg Pro Pro
1

<210> SEQ ID NO 14
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 14

Arg Pro Pro Pro
1

<210> SEQ ID NO 15
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 15

Pro Pro Pro Phe
1

<210> SEQ ID NO 16
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 16

Pro Pro Phe Phe
1

<210> SEQ ID NO 17
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 17

Pro Phe Phe Pro
1

<210> SEQ ID NO 18
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 18
```

-continued

Phe Phe Pro Pro
1

<210> SEQ ID NO 19
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 19

Phe Pro Pro Arg
1

<210> SEQ ID NO 20
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 20

Pro Pro Arg Leu
1

<210> SEQ ID NO 21
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 21

Pro Arg Leu Pro
1

<210> SEQ ID NO 22
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 22

Arg Leu Pro Pro
1

<210> SEQ ID NO 23
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 23

Leu Pro Pro Arg
1

<210> SEQ ID NO 24
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 24

Pro Pro Arg Ile

```
<210> SEQ ID NO 25
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 25

Pro Arg Ile Pro
1

<210> SEQ ID NO 26
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 26

Arg Ile Pro Pro
1

<210> SEQ ID NO 27
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 27

Ile Pro Pro Glu
1

<210> SEQ ID NO 28
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 28

Pro Pro Glu Phe
1

<210> SEQ ID NO 29
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 29

Pro Glu Phe Pro
1

<210> SEQ ID NO 30
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 30

Glu Phe Pro Pro
1
```

```
<210> SEQ ID NO 31
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 31

Phe Pro Pro Arg
1

<210> SEQ ID NO 32
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 32

Pro Pro Arg Phe
1

<210> SEQ ID NO 33
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 33

Pro Arg Phe Pro
1

<210> SEQ ID NO 34
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 34

Arg Phe Pro Pro
1

<210> SEQ ID NO 35
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 35

Phe Pro Pro Arg
1

<210> SEQ ID NO 36
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 36

Pro Pro Arg Phe
1

<210> SEQ ID NO 37
```

```
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 37

Pro Arg Phe Pro
 1

<210> SEQ ID NO 38
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 38

Arg Arg Arg Pro Arg
 1               5

<210> SEQ ID NO 39
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 39

Arg Arg Pro Arg Pro
 1               5

<210> SEQ ID NO 40
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 40

Arg Pro Arg Pro Pro
 1               5

<210> SEQ ID NO 41
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 41

Pro Arg Pro Pro Tyr
 1               5

<210> SEQ ID NO 42
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 42

Arg Pro Pro Tyr Leu
 1               5

<210> SEQ ID NO 43
<211> LENGTH: 5
<212> TYPE: PRT
```

```
<213> ORGANISM: Artificial
<220> FEATURE:
<223> OTHER INFORMATION: peptide derived from cathelicidin PR-39

<400> SEQUENCE: 43

Pro Pro Tyr Leu Pro
1               5

<210> SEQ ID NO 44
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 44

Pro Tyr Leu Pro Arg
1               5

<210> SEQ ID NO 45
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 45

Tyr Leu Pro Arg Pro
1               5

<210> SEQ ID NO 46
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 46

Leu Pro Arg Pro Arg
1               5

<210> SEQ ID NO 47
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 47

Pro Arg Pro Arg Pro
1               5

<210> SEQ ID NO 48
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 48

Arg Pro Arg Pro Pro
1               5

<210> SEQ ID NO 49
<211> LENGTH: 5
<212> TYPE: PRT
<213> ORGANISM: Artificial
<220> FEATURE:
```

<223> OTHER INFORMATION: peptide derived from cathelicidin PR-39

<400> SEQUENCE: 49

Pro Arg Pro Pro Pro
1               5

<210> SEQ ID NO 50
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 50

Arg Pro Pro Pro Phe
1               5

<210> SEQ ID NO 51
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 51

Pro Pro Pro Phe Phe
1               5

<210> SEQ ID NO 52
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 52

Pro Pro Phe Phe Pro
1               5

<210> SEQ ID NO 53
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 53

Pro Phe Phe Pro Pro
1               5

<210> SEQ ID NO 54
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 54

Phe Phe Pro Pro Arg
1               5

<210> SEQ ID NO 55
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 55

Phe Pro Pro Arg Leu
1               5

<210> SEQ ID NO 56
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 56

Pro Pro Arg Leu Pro
1               5

<210> SEQ ID NO 57
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 57

Pro Arg Leu Pro Pro
1               5

<210> SEQ ID NO 58
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 58

Arg Leu Pro Pro Arg
1               5

<210> SEQ ID NO 59
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 59

Leu Pro Pro Arg Ile
1               5

<210> SEQ ID NO 60
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 60

Pro Pro Arg Ile Pro
1               5

<210> SEQ ID NO 61
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 61

```
Pro Arg Ile Pro Pro
1               5
```

<210> SEQ ID NO 62
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 62

```
Arg Ile Pro Pro Glu
1               5
```

<210> SEQ ID NO 63
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 63

```
Ile Pro Pro Glu Phe
1               5
```

<210> SEQ ID NO 64
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 64

```
Pro Pro Glu Phe Pro
1               5
```

<210> SEQ ID NO 65
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 65

```
Pro Glu Phe Pro Pro
1               5
```

<210> SEQ ID NO 66
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 66

```
Glu Phe Pro Pro Arg
1               5
```

<210> SEQ ID NO 67
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 67

```
Phe Pro Pro Arg Phe
1               5
```

```
<210> SEQ ID NO 68
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 68

Pro Pro Arg Phe Pro
1               5

<210> SEQ ID NO 69
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 69

Pro Arg Phe Pro Pro
1               5

<210> SEQ ID NO 70
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 70

Arg Phe Pro Pro Arg
1               5

<210> SEQ ID NO 71
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 71

Phe Pro Pro Arg Phe
1               5

<210> SEQ ID NO 72
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 72

Pro Pro Arg Phe Pro
1               5

<210> SEQ ID NO 73
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 73

Arg Arg Arg Pro Arg Pro
1               5
```

```
<210> SEQ ID NO 74
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 74

Arg Arg Pro Arg Pro Pro
1               5

<210> SEQ ID NO 75
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 75

Arg Pro Arg Pro Pro Tyr
1               5

<210> SEQ ID NO 76
<211> LENGTH: 6
<212> TYPE: PRT
<213> ORGANISM: Artificial
<220> FEATURE:
<223> OTHER INFORMATION: peptide derived from cathelicidin PR-39
<223> OTHER INFORMATION:

<400> SEQUENCE: 76

Pro Arg Pro Pro Tyr Leu
1               5

<210> SEQ ID NO 77
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 77

Arg Pro Pro Tyr Leu Pro
1               5

<210> SEQ ID NO 78
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 78

Pro Pro Tyr Leu Pro Arg
1               5

<210> SEQ ID NO 79
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 79

Pro Tyr Leu Pro Arg Pro
1               5

<210> SEQ ID NO 80
```

```
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 80

Tyr Leu Pro Arg Pro Arg
1               5

<210> SEQ ID NO 81
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 81

Leu Pro Arg Pro Arg Pro
1               5

<210> SEQ ID NO 82
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 82

Pro Arg Pro Arg Pro Pro
1               5

<210> SEQ ID NO 83
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 83

Arg Pro Arg Pro Pro Pro
1               5

<210> SEQ ID NO 84
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 84

Pro Arg Pro Pro Pro Phe
1               5

<210> SEQ ID NO 85
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 85

Arg Pro Pro Pro Phe Phe
1               5

<210> SEQ ID NO 86
<211> LENGTH: 6
<212> TYPE: PRT
```

```
<213> ORGANISM: Artificial
<220> FEATURE:
<223> OTHER INFORMATION: peptide derived from cathelicidin PR-39

<400> SEQUENCE: 86

Pro Pro Pro Phe Phe Pro
1               5

<210> SEQ ID NO 87
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 87

Pro Pro Phe Phe Pro Pro
1               5

<210> SEQ ID NO 88
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 88

Pro Phe Phe Pro Pro Arg
1               5

<210> SEQ ID NO 89
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 89

Phe Phe Pro Pro Arg Leu
1               5

<210> SEQ ID NO 90
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 90

Phe Pro Pro Arg Leu Pro
1               5

<210> SEQ ID NO 91
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 91

Pro Pro Arg Leu Pro Pro
1               5

<210> SEQ ID NO 92
<211> LENGTH: 7
<212> TYPE: PRT
<213> ORGANISM: Artificial
<220> FEATURE:
```

<223> OTHER INFORMATION: peptide derived from cathelicidin PR-39

<400> SEQUENCE: 92

Pro Arg Leu Pro Pro Pro Arg
1               5

<210> SEQ ID NO 93
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 93

Arg Leu Pro Pro Arg Ile
1               5

<210> SEQ ID NO 94
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 94

Leu Pro Pro Arg Ile Pro
1               5

<210> SEQ ID NO 95
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 95

Pro Pro Arg Ile Pro Pro
1               5

<210> SEQ ID NO 96
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 96

Pro Arg Ile Pro Pro Glu
1               5

<210> SEQ ID NO 97
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 97

Arg Ile Pro Pro Glu Phe
1               5

<210> SEQ ID NO 98
<211> LENGTH: 6
<212> TYPE: PRT
<213> ORGANISM: Artificial
<220> FEATURE:
<223> OTHER INFORMATION: peptide derived from cathelicidin PR-39

```
<400> SEQUENCE: 98

Ile Pro Pro Glu Phe Pro
1               5

<210> SEQ ID NO 99
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 99

Pro Pro Glu Phe Pro Pro
1               5

<210> SEQ ID NO 100
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 100

Pro Glu Phe Pro Pro Arg
1               5

<210> SEQ ID NO 101
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 101

Glu Phe Pro Pro Arg Phe
1               5

<210> SEQ ID NO 102
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 102

Phe Pro Pro Arg Phe Pro
1               5

<210> SEQ ID NO 103
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 103

Pro Pro Arg Phe Pro Pro
1               5

<210> SEQ ID NO 104
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 104
```

```
Pro Arg Phe Pro Pro Arg
1               5

<210> SEQ ID NO 105
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 105

Arg Phe Pro Pro Arg Phe
1               5

<210> SEQ ID NO 106
<211> LENGTH: 6
<212> TYPE: PRT
<213> ORGANISM: Artificial
<220> FEATURE:
<223> OTHER INFORMATION: peptide derived from cathelicidin PR-39

<400> SEQUENCE: 106

Phe Pro Pro Arg Phe Pro
1               5

<210> SEQ ID NO 107
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 107

Arg Arg Arg Pro Arg Pro Pro
1               5

<210> SEQ ID NO 108
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 108

Arg Arg Pro Arg Pro Pro Tyr
1               5

<210> SEQ ID NO 109
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 109

Arg Pro Arg Pro Pro Tyr Leu
1               5

<210> SEQ ID NO 110
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 110

Pro Arg Pro Pro Tyr Leu Pro
1               5
```

```
<210> SEQ ID NO 111
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 111

Arg Pro Pro Tyr Leu Pro Arg
1               5

<210> SEQ ID NO 112
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 112

Pro Pro Tyr Leu Pro Arg Pro
1               5

<210> SEQ ID NO 113
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 113

Pro Tyr Leu Pro Arg Pro Arg
1               5

<210> SEQ ID NO 114
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 114

Tyr Leu Pro Arg Pro Arg Pro
1               5

<210> SEQ ID NO 115
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 115

Leu Pro Arg Pro Arg Pro Pro
1               5

<210> SEQ ID NO 116
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 116

Pro Arg Pro Arg Pro Pro Pro
1               5
```

<210> SEQ ID NO 117
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 117

Arg Pro Arg Pro Pro Pro Phe
1               5

<210> SEQ ID NO 118
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 118

Pro Arg Pro Pro Pro Phe Phe
1               5

<210> SEQ ID NO 119
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 119

Arg Pro Pro Pro Phe Phe Pro
1               5

<210> SEQ ID NO 120
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 120

Pro Pro Pro Phe Phe Pro Pro
1               5

<210> SEQ ID NO 121
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 121

Pro Pro Phe Phe Pro Pro Arg
1               5

<210> SEQ ID NO 122
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 122

Pro Phe Phe Pro Pro Arg Leu
1               5

<210> SEQ ID NO 123
<211> LENGTH: 7

```
<212> TYPE: PRT
<213> ORGANISM: Artificial
<220> FEATURE:
<223> OTHER INFORMATION: peptide derived from cathelicidin PR-39

<400> SEQUENCE: 123

Phe Phe Pro Pro Arg Leu Pro
1               5

<210> SEQ ID NO 124
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 124

Phe Pro Pro Arg Leu Pro Pro
1               5

<210> SEQ ID NO 125
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 125

Pro Pro Arg Leu Pro Pro Arg
1               5

<210> SEQ ID NO 126
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 126

Pro Arg Leu Pro Pro Arg Ile
1               5

<210> SEQ ID NO 127
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 127

Arg Leu Pro Pro Arg Ile Pro
1               5

<210> SEQ ID NO 128
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 128

Leu Pro Pro Arg Ile Pro Pro
1               5

<210> SEQ ID NO 129
<211> LENGTH: 7
<212> TYPE: PRT
<213> ORGANISM: Artificial
```

<220> FEATURE:
<223> OTHER INFORMATION: peptide derived from cathelicidin PR-39

<400> SEQUENCE: 129

Pro Pro Arg Ile Pro Pro Glu
1               5

<210> SEQ ID NO 130
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 130

Pro Arg Ile Pro Pro Glu Phe
1               5

<210> SEQ ID NO 131
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 131

Arg Ile Pro Pro Glu Phe Pro
1               5

<210> SEQ ID NO 132
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 132

Ile Pro Pro Glu Phe Pro Pro
1               5

<210> SEQ ID NO 133
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 133

Pro Pro Glu Phe Pro Pro Arg
1               5

<210> SEQ ID NO 134
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 134

Pro Glu Phe Pro Pro Arg Phe
1               5

<210> SEQ ID NO 135
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 135

Glu Phe Pro Pro Arg Phe Pro
1               5

<210> SEQ ID NO 136
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 136

Phe Pro Pro Arg Phe Pro Pro
1               5

<210> SEQ ID NO 137
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 137

Pro Pro Arg Phe Pro Pro Arg
1               5

<210> SEQ ID NO 138
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 138

Pro Arg Phe Pro Pro Arg Phe
1               5

<210> SEQ ID NO 139
<211> LENGTH: 7
<212> TYPE: PRT
<213> ORGANISM: Artificial
<220> FEATURE:
<223> OTHER INFORMATION: peptide derived from cathelicidin PR-39

<400> SEQUENCE: 139

Arg Phe Pro Pro Arg Phe Pro
1               5

<210> SEQ ID NO 140
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 140

Arg Arg Arg Pro Arg Pro Pro Tyr
1               5

<210> SEQ ID NO 141
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 141

Arg Arg Pro Arg Pro Pro Tyr Leu
1               5

<210> SEQ ID NO 142
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 142

Arg Pro Arg Pro Pro Tyr Leu Pro
1               5

<210> SEQ ID NO 143
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 143

Pro Arg Pro Pro Tyr Leu Pro Arg
1               5

<210> SEQ ID NO 144
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 144

Arg Pro Pro Tyr Leu Pro Arg Pro
1               5

<210> SEQ ID NO 145
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 145

Pro Pro Tyr Leu Pro Arg Pro Arg
1               5

<210> SEQ ID NO 146
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 146

Pro Tyr Leu Pro Arg Pro Arg Pro
1               5

<210> SEQ ID NO 147
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 147

Tyr Leu Pro Arg Pro Arg Pro Pro

<210> SEQ ID NO 148
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 148

Leu Pro Arg Pro Arg Pro Pro Pro
1               5

<210> SEQ ID NO 149
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 149

Pro Arg Pro Arg Pro Pro Pro Phe
1               5

<210> SEQ ID NO 150
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 150

Arg Pro Arg Pro Pro Pro Phe Phe
1               5

<210> SEQ ID NO 151
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 151

Pro Arg Pro Pro Pro Phe Phe Pro
1               5

<210> SEQ ID NO 152
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 152

Arg Pro Pro Pro Phe Phe Pro Pro
1               5

<210> SEQ ID NO 153
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 153

Pro Pro Pro Phe Phe Pro Pro Arg
1               5

<210> SEQ ID NO 154
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 154

Pro Pro Phe Phe Pro Pro Arg Leu
1               5

<210> SEQ ID NO 155
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 155

Pro Phe Phe Pro Pro Arg Leu Pro
1               5

<210> SEQ ID NO 156
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 156

Phe Phe Pro Pro Arg Leu Pro Pro
1               5

<210> SEQ ID NO 157
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 157

Phe Pro Pro Arg Leu Pro Pro Arg
1               5

<210> SEQ ID NO 158
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 158

Pro Pro Arg Leu Pro Pro Arg Ile
1               5

<210> SEQ ID NO 159
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 159

Pro Arg Leu Pro Pro Arg Ile Pro
1               5

<210> SEQ ID NO 160

```
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 160

Arg Leu Pro Pro Arg Ile Pro Pro
1               5

<210> SEQ ID NO 161
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 161

Leu Pro Pro Arg Ile Pro Pro Glu
1               5

<210> SEQ ID NO 162
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 162

Pro Pro Arg Ile Pro Pro Glu Phe
1               5

<210> SEQ ID NO 163
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 163

Pro Arg Ile Pro Pro Glu Phe Pro
1               5

<210> SEQ ID NO 164
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 164

Arg Ile Pro Pro Glu Phe Pro Pro
1               5

<210> SEQ ID NO 165
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 165

Ile Pro Pro Glu Phe Pro Pro Arg
1               5

<210> SEQ ID NO 166
<211> LENGTH: 8
<212> TYPE: PRT
```

```
<213> ORGANISM: Artificial
<220> FEATURE:
<223> OTHER INFORMATION: peptide derived from cathelicidin PR-39

<400> SEQUENCE: 166

Pro Pro Glu Phe Pro Pro Arg Phe
1               5

<210> SEQ ID NO 167
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 167

Pro Glu Phe Pro Pro Arg Phe Pro
1               5

<210> SEQ ID NO 168
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 168

Glu Phe Pro Pro Arg Phe Pro Pro
1               5

<210> SEQ ID NO 169
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 169

Phe Pro Pro Arg Phe Pro Pro Arg
1               5

<210> SEQ ID NO 170
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 170

Pro Pro Arg Phe Pro Pro Arg Phe
1               5

<210> SEQ ID NO 171
<211> LENGTH: 8
<212> TYPE: PRT
<213> ORGANISM: Artificial
<220> FEATURE:
<223> OTHER INFORMATION: peptide derived from cathelicidin PR-39

<400> SEQUENCE: 171

Pro Arg Phe Pro Pro Arg Phe Pro
1               5

<210> SEQ ID NO 172
<211> LENGTH: 9
<212> TYPE: PRT
<213> ORGANISM: Artificial
<220> FEATURE:
```

<223> OTHER INFORMATION: peptide derived from cathelicidin PR-39

<400> SEQUENCE: 172

Arg Arg Arg Pro Arg Pro Pro Tyr Leu
1               5

<210> SEQ ID NO 173
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 173

Arg Arg Pro Arg Pro Pro Tyr Leu Pro
1               5

<210> SEQ ID NO 174
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 174

Arg Pro Arg Pro Pro Tyr Leu Pro Arg
1               5

<210> SEQ ID NO 175
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 175

Pro Arg Pro Pro Tyr Leu Pro Arg Pro
1               5

<210> SEQ ID NO 176
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 176

Arg Pro Pro Tyr Leu Pro Arg Pro Arg
1               5

<210> SEQ ID NO 177
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 177

Pro Pro Tyr Leu Pro Arg Pro Arg Pro
1               5

<210> SEQ ID NO 178
<211> LENGTH: 9
<212> TYPE: PRT
<213> ORGANISM: Artificial
<220> FEATURE:
<223> OTHER INFORMATION: peptide derived from cathelicidin PR-39

```
<400> SEQUENCE: 178

Pro Tyr Leu Pro Arg Pro Arg Pro Pro
1               5

<210> SEQ ID NO 179
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 179

Tyr Leu Pro Arg Pro Arg Pro Pro Pro
1               5

<210> SEQ ID NO 180
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 180

Leu Pro Arg Pro Arg Pro Pro Pro Phe
1               5

<210> SEQ ID NO 181
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 181

Pro Arg Pro Arg Pro Pro Pro Phe Phe
1               5

<210> SEQ ID NO 182
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 182

Arg Pro Arg Pro Pro Pro Phe Phe Pro
1               5

<210> SEQ ID NO 183
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 183

Pro Arg Pro Pro Pro Phe Phe Pro Pro
1               5

<210> SEQ ID NO 184
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 184
```

```
Arg Pro Pro Pro Phe Phe Pro Pro Arg
1               5
```

<210> SEQ ID NO 185
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 185

```
Pro Pro Pro Phe Phe Pro Pro Arg Leu
1               5
```

<210> SEQ ID NO 186
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 186

```
Pro Pro Phe Phe Pro Pro Arg Leu Pro
1               5
```

<210> SEQ ID NO 187
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 187

```
Pro Phe Phe Pro Pro Arg Leu Pro Pro
1               5
```

<210> SEQ ID NO 188
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 188

```
Phe Phe Pro Pro Arg Leu Pro Pro Arg
1               5
```

<210> SEQ ID NO 189
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 189

```
Phe Pro Pro Arg Leu Pro Pro Arg Ile
1               5
```

<210> SEQ ID NO 190
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 190

```
Pro Pro Arg Leu Pro Pro Arg Ile Pro
1               5
```

```
<210> SEQ ID NO 191
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 191

Pro Arg Leu Pro Pro Arg Ile Pro Pro
1               5

<210> SEQ ID NO 192
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 192

Arg Leu Pro Pro Arg Ile Pro Pro Glu
1               5

<210> SEQ ID NO 193
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 193

Leu Pro Pro Arg Ile Pro Pro Glu Phe
1               5

<210> SEQ ID NO 194
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 194

Pro Pro Arg Ile Pro Pro Glu Phe Pro
1               5

<210> SEQ ID NO 195
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 195

Pro Arg Ile Pro Pro Glu Phe Pro Pro
1               5

<210> SEQ ID NO 196
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 196

Arg Ile Pro Pro Glu Phe Pro Pro Arg
1               5
```

```
<210> SEQ ID NO 197
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 197

Ile Pro Pro Glu Phe Pro Pro Arg Phe
1               5

<210> SEQ ID NO 198
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 198

Pro Pro Glu Phe Pro Pro Arg Phe Pro
1               5

<210> SEQ ID NO 199
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 199

Pro Glu Phe Pro Pro Arg Phe Pro Pro
1               5

<210> SEQ ID NO 200
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 200

Glu Phe Pro Pro Arg Phe Pro Pro Arg
1               5

<210> SEQ ID NO 201
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 201

Phe Pro Pro Arg Phe Pro Pro Arg Phe
1               5

<210> SEQ ID NO 202
<211> LENGTH: 9
<212> TYPE: PRT
<213> ORGANISM: Artificial
<220> FEATURE:
<223> OTHER INFORMATION: peptide derived from cathelicidin PR-39

<400> SEQUENCE: 202

Pro Pro Arg Phe Pro Pro Arg Phe Pro
1               5

<210> SEQ ID NO 203
<211> LENGTH: 10
```

```
<212> TYPE: PRT
<213> ORGANISM: Artificial
<220> FEATURE:
<223> OTHER INFORMATION: peptide derived from cathelicidin PR-39

<400> SEQUENCE: 203

Arg Arg Arg Pro Arg Pro Pro Tyr Leu Pro
1               5                   10

<210> SEQ ID NO 204
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 204

Arg Arg Pro Arg Pro Pro Tyr Leu Pro Arg
1               5                   10

<210> SEQ ID NO 205
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 205

Arg Pro Arg Pro Pro Tyr Leu Pro Arg Pro
1               5                   10

<210> SEQ ID NO 206
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 206

Pro Arg Pro Pro Tyr Leu Pro Arg Pro Arg
1               5                   10

<210> SEQ ID NO 207
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 207

Arg Pro Pro Tyr Leu Pro Arg Pro Arg Pro
1               5                   10

<210> SEQ ID NO 208
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 208

Pro Pro Tyr Leu Pro Arg Pro Arg Pro Pro
1               5                   10

<210> SEQ ID NO 209
<211> LENGTH: 10
<212> TYPE: PRT
<213> ORGANISM: Artificial
```

<220> FEATURE:
<223> OTHER INFORMATION: peptide derived from cathelicidin PR-39

<400> SEQUENCE: 209

Pro Tyr Leu Pro Arg Pro Arg Pro Pro Pro
1               5                   10

<210> SEQ ID NO 210
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 210

Tyr Leu Pro Arg Pro Arg Pro Pro Pro Phe
1               5                   10

<210> SEQ ID NO 211
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 211

Leu Pro Arg Pro Arg Pro Pro Pro Phe Phe
1               5                   10

<210> SEQ ID NO 212
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 212

Pro Arg Pro Arg Pro Pro Pro Phe Phe Pro
1               5                   10

<210> SEQ ID NO 213
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 213

Arg Pro Arg Pro Pro Pro Phe Phe Pro Pro
1               5                   10

<210> SEQ ID NO 214
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 214

Pro Arg Pro Pro Pro Phe Phe Pro Pro Arg
1               5                   10

<210> SEQ ID NO 215
<211> LENGTH: 10
<212> TYPE: PRT
<213> ORGANISM: Artificial
<220> FEATURE:
<223> OTHER INFORMATION: peptide derived from cathelicidin PR-39

```
<400> SEQUENCE: 215

Arg Pro Pro Pro Phe Phe Pro Pro Arg Leu
1               5                   10

<210> SEQ ID NO 216
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 216

Pro Pro Pro Phe Phe Pro Pro Arg Leu Pro
1               5                   10

<210> SEQ ID NO 217
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 217

Pro Pro Phe Phe Pro Pro Arg Leu Pro Pro
1               5                   10

<210> SEQ ID NO 218
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 218

Pro Phe Phe Pro Pro Arg Leu Pro Pro Arg
1               5                   10

<210> SEQ ID NO 219
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 219

Phe Phe Pro Pro Arg Leu Pro Pro Arg Ile
1               5                   10

<210> SEQ ID NO 220
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 220

Phe Pro Pro Arg Leu Pro Pro Arg Ile Pro
1               5                   10

<210> SEQ ID NO 221
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 221
```

```
Pro Pro Arg Leu Pro Pro Arg Ile Pro Pro
1               5                   10

<210> SEQ ID NO 222
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 222

Pro Arg Leu Pro Pro Arg Ile Pro Pro Glu
1               5                   10

<210> SEQ ID NO 223
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 223

Arg Leu Pro Pro Arg Ile Pro Pro Glu Phe
1               5                   10

<210> SEQ ID NO 224
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 224

Leu Pro Pro Arg Ile Pro Pro Glu Phe Pro
1               5                   10

<210> SEQ ID NO 225
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 225

Pro Pro Arg Ile Pro Pro Glu Phe Pro Pro
1               5                   10

<210> SEQ ID NO 226
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 226

Pro Arg Ile Pro Pro Glu Phe Pro Pro Arg
1               5                   10

<210> SEQ ID NO 227
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 227

Arg Ile Pro Pro Glu Phe Pro Pro Arg Phe
```

-continued

<210> SEQ ID NO 228
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 228

Ile Pro Pro Glu Phe Pro Pro Arg Phe Pro
1               5                   10

<210> SEQ ID NO 229
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 229

Pro Pro Glu Phe Pro Pro Arg Phe Pro Pro
1               5                   10

<210> SEQ ID NO 230
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 230

Pro Glu Phe Pro Pro Arg Phe Pro Pro Arg
1               5                   10

<210> SEQ ID NO 231
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 231

Glu Phe Pro Pro Arg Phe Pro Pro Arg Phe
1               5                   10

<210> SEQ ID NO 232
<211> LENGTH: 10
<212> TYPE: PRT
<213> ORGANISM: Artificial
<220> FEATURE:
<223> OTHER INFORMATION: peptide derived from cathelicidin PR-39

<400> SEQUENCE: 232

Phe Pro Pro Arg Phe Pro Pro Arg Phe Pro
1               5                   10

<210> SEQ ID NO 233
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 233

Arg Arg Arg Pro Arg Pro Pro Tyr Leu Pro Arg
1               5                   10

```
<210> SEQ ID NO 234
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 234

Arg Arg Pro Arg Pro Pro Tyr Leu Pro Arg Pro
1               5                   10

<210> SEQ ID NO 235
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 235

Arg Pro Arg Pro Pro Tyr Leu Pro Arg Pro Arg
1               5                   10

<210> SEQ ID NO 236
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 236

Pro Arg Pro Pro Tyr Leu Pro Arg Pro Arg Pro
1               5                   10

<210> SEQ ID NO 237
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 237

Arg Pro Pro Tyr Leu Pro Arg Pro Arg Pro Pro
1               5                   10

<210> SEQ ID NO 238
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 238

Pro Pro Tyr Leu Pro Arg Pro Arg Pro Pro Pro
1               5                   10

<210> SEQ ID NO 239
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 239

Pro Tyr Leu Pro Arg Pro Arg Pro Pro Pro Phe
1               5                   10

<210> SEQ ID NO 240
```

```
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 240

Tyr Leu Pro Arg Pro Arg Pro Pro Pro Phe Phe
1               5                   10

<210> SEQ ID NO 241
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 241

Leu Pro Arg Pro Arg Pro Pro Pro Phe Phe Pro
1               5                   10

<210> SEQ ID NO 242
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 242

Pro Arg Pro Arg Pro Pro Pro Phe Phe Pro Pro
1               5                   10

<210> SEQ ID NO 243
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 243

Arg Pro Arg Pro Pro Pro Phe Phe Pro Pro Arg
1               5                   10

<210> SEQ ID NO 244
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 244

Pro Arg Pro Pro Pro Phe Phe Pro Pro Arg Leu
1               5                   10

<210> SEQ ID NO 245
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 245

Arg Pro Pro Pro Phe Phe Pro Pro Arg Leu Pro
1               5                   10

<210> SEQ ID NO 246
<211> LENGTH: 11
<212> TYPE: PRT
```

-continued

<213> ORGANISM: Artificial
<220> FEATURE:
<223> OTHER INFORMATION: peptide derived from cathelicidin PR-39

<400> SEQUENCE: 246

Pro Pro Pro Phe Phe Pro Pro Arg Leu Pro Pro
1               5                   10

<210> SEQ ID NO 247
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 247

Pro Pro Phe Phe Pro Pro Arg Leu Pro Pro Arg
1               5                   10

<210> SEQ ID NO 248
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 248

Pro Phe Phe Pro Pro Arg Leu Pro Pro Arg Ile
1               5                   10

<210> SEQ ID NO 249
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 249

Phe Phe Pro Pro Arg Leu Pro Pro Arg Ile Pro
1               5                   10

<210> SEQ ID NO 250
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 250

Phe Pro Pro Arg Leu Pro Pro Arg Ile Pro Pro
1               5                   10

<210> SEQ ID NO 251
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 251

Pro Pro Arg Leu Pro Pro Arg Ile Pro Pro Glu
1               5                   10

<210> SEQ ID NO 252
<211> LENGTH: 11
<212> TYPE: PRT
<213> ORGANISM: Artificial
<220> FEATURE:

<223> OTHER INFORMATION: peptide derived from cathelicidin PR-39

<400> SEQUENCE: 252

Pro Arg Leu Pro Pro Arg Ile Pro Pro Glu Phe
1               5                   10

<210> SEQ ID NO 253
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 253

Arg Leu Pro Pro Arg Ile Pro Pro Glu Phe Pro
1               5                   10

<210> SEQ ID NO 254
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 254

Leu Pro Pro Arg Ile Pro Pro Glu Phe Pro Pro
1               5                   10

<210> SEQ ID NO 255
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 255

Pro Pro Arg Ile Pro Pro Glu Phe Pro Pro Arg
1               5                   10

<210> SEQ ID NO 256
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 256

Pro Arg Ile Pro Pro Glu Phe Pro Pro Arg Phe
1               5                   10

<210> SEQ ID NO 257
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 257

Arg Ile Pro Pro Glu Phe Pro Pro Arg Phe Pro
1               5                   10

<210> SEQ ID NO 258
<211> LENGTH: 11
<212> TYPE: PRT
<213> ORGANISM: Artificial
<220> FEATURE:
<223> OTHER INFORMATION: peptide derived from cathelicidin PR-39

-continued

<400> SEQUENCE: 258

Ile Pro Pro Glu Phe Pro Pro Arg Phe Pro Pro
1               5                   10

<210> SEQ ID NO 259
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 259

Pro Pro Glu Phe Pro Pro Arg Phe Pro Pro Arg
1               5                   10

<210> SEQ ID NO 260
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 260

Pro Glu Phe Pro Pro Arg Phe Pro Pro Arg Phe
1               5                   10

<210> SEQ ID NO 261
<211> LENGTH: 11
<212> TYPE: PRT
<213> ORGANISM: Artificial
<220> FEATURE:
<223> OTHER INFORMATION: peptide derived from cathelicidin PR-39

<400> SEQUENCE: 261

Glu Phe Pro Pro Arg Phe Pro Pro Arg Phe Pro
1               5                   10

<210> SEQ ID NO 262
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 262

Arg Arg Arg Pro Arg Pro Pro Tyr Leu Pro Arg Pro
1               5                   10

<210> SEQ ID NO 263
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 263

Arg Arg Pro Arg Pro Pro Tyr Leu Pro Arg Pro Arg
1               5                   10

<210> SEQ ID NO 264
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 264

Arg Pro Arg Pro Pro Tyr Leu Pro Arg Pro Arg Pro
1               5                   10

<210> SEQ ID NO 265
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 265

Pro Arg Pro Pro Tyr Leu Pro Arg Pro Arg Pro Pro
1               5                   10

<210> SEQ ID NO 266
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 266

Arg Pro Pro Tyr Leu Pro Arg Pro Arg Pro Pro Pro
1               5                   10

<210> SEQ ID NO 267
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 267

Pro Pro Tyr Leu Pro Arg Pro Arg Pro Pro Pro Phe
1               5                   10

<210> SEQ ID NO 268
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 268

Pro Tyr Leu Pro Arg Pro Arg Pro Pro Pro Phe Phe
1               5                   10

<210> SEQ ID NO 269
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 269

Tyr Leu Pro Arg Pro Arg Pro Pro Pro Phe Phe Pro
1               5                   10

<210> SEQ ID NO 270
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 270

Leu Pro Arg Pro Arg Pro Pro Pro Phe Phe Pro Pro
1               5                   10

```
<210> SEQ ID NO 271
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 271

Pro Arg Pro Arg Pro Pro Pro Phe Phe Pro Pro Arg
1               5                   10

<210> SEQ ID NO 272
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 272

Arg Pro Arg Pro Pro Pro Phe Phe Pro Pro Arg Leu
1               5                   10

<210> SEQ ID NO 273
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 273

Pro Arg Pro Pro Pro Phe Phe Pro Pro Arg Leu Pro
1               5                   10

<210> SEQ ID NO 274
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 274

Arg Pro Pro Pro Phe Phe Pro Pro Arg Leu Pro Pro
1               5                   10

<210> SEQ ID NO 275
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 275

Pro Pro Pro Phe Phe Pro Pro Arg Leu Pro Pro Arg
1               5                   10

<210> SEQ ID NO 276
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 276

Pro Pro Phe Phe Pro Pro Arg Leu Pro Pro Arg Ile
1               5                   10
```

-continued

```
<210> SEQ ID NO 277
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 277

Pro Phe Phe Pro Pro Arg Leu Pro Pro Arg Ile Pro
1               5                   10

<210> SEQ ID NO 278
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 278

Phe Phe Pro Pro Arg Leu Pro Pro Arg Ile Pro Pro
1               5                   10

<210> SEQ ID NO 279
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 279

Phe Pro Pro Arg Leu Pro Pro Arg Ile Pro Pro Glu
1               5                   10

<210> SEQ ID NO 280
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 280

Pro Pro Arg Leu Pro Pro Arg Ile Pro Pro Glu Phe
1               5                   10

<210> SEQ ID NO 281
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 281

Pro Arg Leu Pro Pro Arg Ile Pro Pro Glu Phe Pro
1               5                   10

<210> SEQ ID NO 282
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 282

Arg Leu Pro Pro Arg Ile Pro Pro Glu Phe Pro Pro
1               5                   10

<210> SEQ ID NO 283
<211> LENGTH: 12
```

```
<212> TYPE: PRT
<213> ORGANISM: Artificial
<220> FEATURE:
<223> OTHER INFORMATION: peptide derived from cathelicidin PR-39

<400> SEQUENCE: 283

Leu Pro Pro Arg Ile Pro Pro Glu Phe Pro Pro Arg
1               5                   10

<210> SEQ ID NO 284
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 284

Pro Pro Arg Ile Pro Pro Glu Phe Pro Pro Arg Phe
1               5                   10

<210> SEQ ID NO 285
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 285

Pro Arg Ile Pro Pro Glu Phe Pro Pro Arg Phe Pro
1               5                   10

<210> SEQ ID NO 286
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 286

Arg Ile Pro Pro Glu Phe Pro Pro Arg Phe Pro Pro
1               5                   10

<210> SEQ ID NO 287
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 287

Ile Pro Pro Glu Phe Pro Pro Arg Phe Pro Pro Arg
1               5                   10

<210> SEQ ID NO 288
<211> LENGTH: 12
<212> TYPE: PRT
<213> ORGANISM: Artificial
<220> FEATURE:
<223> OTHER INFORMATION: peptide derived from cathelicidin PR-39

<400> SEQUENCE: 288

Pro Pro Glu Phe Pro Pro Arg Phe Pro Pro Arg Phe
1               5                   10

<210> SEQ ID NO 289
<211> LENGTH: 12
<212> TYPE: PRT
<213> ORGANISM: Artificial
```

```
<220> FEATURE:
<223> OTHER INFORMATION: peptide derived from cathelicidin PR-39

<400> SEQUENCE: 289

Pro Glu Phe Pro Pro Arg Phe Pro Pro Arg Phe Pro
1               5                   10

<210> SEQ ID NO 290
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 290

Arg Arg Arg Pro Arg Pro Pro Tyr Leu Pro Arg Pro Arg
1               5                   10

<210> SEQ ID NO 291
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 291

Arg Arg Pro Arg Pro Pro Tyr Leu Pro Arg Pro Arg Pro
1               5                   10

<210> SEQ ID NO 292
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 292

Arg Pro Arg Pro Pro Tyr Leu Pro Arg Pro Arg Pro Pro
1               5                   10

<210> SEQ ID NO 293
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 293

Pro Arg Pro Pro Tyr Leu Pro Arg Pro Arg Pro Pro Pro
1               5                   10

<210> SEQ ID NO 294
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 294

Arg Pro Pro Tyr Leu Pro Arg Pro Arg Pro Pro Pro Phe
1               5                   10

<210> SEQ ID NO 295
<211> LENGTH: 13
<212> TYPE: PRT
<213> ORGANISM: Artificial
<220> FEATURE:
<223> OTHER INFORMATION: peptide derived from cathelicidin PR-39
```

<400> SEQUENCE: 295

Pro Pro Tyr Leu Pro Arg Pro Arg Pro Pro Phe Phe
1               5                   10

<210> SEQ ID NO 296
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 296

Pro Tyr Leu Pro Arg Pro Arg Pro Pro Phe Phe Pro
1               5                   10

<210> SEQ ID NO 297
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 297

Tyr Leu Pro Arg Pro Arg Pro Pro Phe Phe Pro Pro
1               5                   10

<210> SEQ ID NO 298
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 298

Leu Pro Arg Pro Arg Pro Pro Pro Phe Phe Pro Pro Arg
1               5                   10

<210> SEQ ID NO 299
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 299

Pro Arg Pro Arg Pro Pro Pro Phe Phe Pro Pro Arg Leu
1               5                   10

<210> SEQ ID NO 300
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 300

Arg Pro Arg Pro Pro Pro Phe Phe Pro Pro Arg Leu Pro
1               5                   10

<210> SEQ ID NO 301
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 301

```
Pro Arg Pro Pro Pro Phe Phe Pro Pro Arg Leu Pro Pro
1               5                   10
```

<210> SEQ ID NO 302
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 302

```
Arg Pro Pro Pro Phe Phe Pro Pro Arg Leu Pro Pro Arg
1               5                   10
```

<210> SEQ ID NO 303
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 303

```
Pro Pro Pro Phe Phe Pro Pro Arg Leu Pro Pro Arg Ile
1               5                   10
```

<210> SEQ ID NO 304
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 304

```
Pro Pro Phe Phe Pro Pro Arg Leu Pro Pro Arg Ile Pro
1               5                   10
```

<210> SEQ ID NO 305
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 305

```
Pro Phe Phe Pro Pro Arg Leu Pro Pro Arg Ile Pro Pro
1               5                   10
```

<210> SEQ ID NO 306
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 306

```
Phe Phe Pro Pro Arg Leu Pro Pro Arg Ile Pro Pro Glu
1               5                   10
```

<210> SEQ ID NO 307
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 307

Phe Pro Pro Arg Leu Pro Pro Arg Ile Pro Pro Glu Phe

-continued

<210> SEQ ID NO 308
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 308

Pro Pro Arg Leu Pro Pro Arg Ile Pro Pro Glu Phe Pro
1               5                   10

<210> SEQ ID NO 309
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 309

Pro Arg Leu Pro Pro Arg Ile Pro Pro Glu Phe Pro Pro
1               5                   10

<210> SEQ ID NO 310
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 310

Arg Leu Pro Pro Arg Ile Pro Pro Glu Phe Pro Pro Arg
1               5                   10

<210> SEQ ID NO 311
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 311

Leu Pro Pro Arg Ile Pro Pro Glu Phe Pro Pro Arg Phe
1               5                   10

<210> SEQ ID NO 312
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 312

Pro Pro Arg Ile Pro Pro Glu Phe Pro Pro Arg Phe Pro
1               5                   10

<210> SEQ ID NO 313
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 313

Pro Arg Ile Pro Pro Glu Phe Pro Pro Arg Phe Pro Pro
1               5                   10

<210> SEQ ID NO 314
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 314

Arg Ile Pro Pro Glu Phe Pro Pro Arg Phe Pro Pro Arg
1               5                   10

<210> SEQ ID NO 315
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 315

Ile Pro Pro Glu Phe Pro Pro Arg Phe Pro Pro Arg Phe
1               5                   10

<210> SEQ ID NO 316
<211> LENGTH: 13
<212> TYPE: PRT
<213> ORGANISM: Artificial
<220> FEATURE:
<223> OTHER INFORMATION: peptide derived from cathelicidin PR-39

<400> SEQUENCE: 316

Pro Pro Glu Phe Pro Pro Arg Phe Pro Pro Arg Phe Pro
1               5                   10

<210> SEQ ID NO 317
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 317

Arg Arg Arg Pro Arg Pro Pro Tyr Leu Pro Arg Pro Arg Pro
1               5                   10

<210> SEQ ID NO 318
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 318

Arg Arg Pro Arg Pro Pro Tyr Leu Pro Arg Pro Arg Pro Pro
1               5                   10

<210> SEQ ID NO 319
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 319

Arg Pro Arg Pro Pro Tyr Leu Pro Arg Pro Arg Pro Pro Pro
1               5                   10

<210> SEQ ID NO 320

```
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 320

Pro Arg Pro Pro Tyr Leu Pro Arg Pro Arg Pro Pro Pro Phe
1               5                   10

<210> SEQ ID NO 321
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 321

Arg Pro Pro Tyr Leu Pro Arg Pro Arg Pro Pro Pro Phe Phe
1               5                   10

<210> SEQ ID NO 322
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 322

Pro Pro Tyr Leu Pro Arg Pro Arg Pro Pro Phe Phe Pro
1               5                   10

<210> SEQ ID NO 323
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 323

Pro Tyr Leu Pro Arg Pro Arg Pro Pro Pro Phe Phe Pro Pro
1               5                   10

<210> SEQ ID NO 324
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 324

Tyr Leu Pro Arg Pro Arg Pro Pro Pro Phe Phe Pro Pro Arg
1               5                   10

<210> SEQ ID NO 325
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 325

Leu Pro Arg Pro Arg Pro Pro Pro Phe Phe Pro Pro Arg Leu
1               5                   10

<210> SEQ ID NO 326
<211> LENGTH: 14
<212> TYPE: PRT
```

```
<213> ORGANISM: Artificial
<220> FEATURE:
<223> OTHER INFORMATION: peptide derived from cathelicidin PR-39

<400> SEQUENCE: 326

Pro Arg Pro Arg Pro Pro Phe Phe Pro Pro Arg Leu Pro
1               5                   10

<210> SEQ ID NO 327
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 327

Pro Arg Pro Pro Pro Phe Phe Pro Pro Arg Leu Pro Pro Arg
1               5                   10

<210> SEQ ID NO 328
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 328

Arg Pro Pro Pro Phe Phe Pro Pro Arg Leu Pro Pro Arg Ile
1               5                   10

<210> SEQ ID NO 329
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 329

Pro Pro Pro Phe Phe Pro Pro Arg Leu Pro Pro Arg Ile Pro
1               5                   10

<210> SEQ ID NO 330
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 330

Pro Pro Phe Phe Pro Pro Arg Leu Pro Pro Arg Ile Pro Pro
1               5                   10

<210> SEQ ID NO 331
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 331

Pro Phe Phe Pro Pro Arg Leu Pro Pro Arg Ile Pro Pro Glu
1               5                   10

<210> SEQ ID NO 332
<211> LENGTH: 14
<212> TYPE: PRT
<213> ORGANISM: Artificial
<220> FEATURE:
```

<223> OTHER INFORMATION: peptide derived from cathelicidin PR-39

<400> SEQUENCE: 332

Phe Phe Pro Pro Arg Leu Pro Pro Arg Ile Pro Pro Glu Phe
1               5                   10

<210> SEQ ID NO 333
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 333

Phe Pro Pro Arg Leu Pro Pro Arg Ile Pro Pro Glu Phe Pro
1               5                   10

<210> SEQ ID NO 334
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 334

Pro Arg Leu Pro Pro Arg Ile Pro Pro Glu Phe Pro Pro Arg
1               5                   10

<210> SEQ ID NO 335
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 335

Arg Leu Pro Pro Arg Ile Pro Pro Glu Phe Pro Pro Arg Phe
1               5                   10

<210> SEQ ID NO 336
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 336

Leu Pro Pro Arg Ile Pro Pro Glu Phe Pro Pro Arg Phe Pro
1               5                   10

<210> SEQ ID NO 337
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 337

Pro Pro Arg Ile Pro Pro Glu Phe Pro Pro Arg Phe Pro Pro
1               5                   10

<210> SEQ ID NO 338
<211> LENGTH: 14
<212> TYPE: PRT
<213> ORGANISM: Artificial
<220> FEATURE:
<223> OTHER INFORMATION: peptide derived from cathelicidin PR-39

```
<400> SEQUENCE: 338

Pro Arg Ile Pro Pro Glu Phe Pro Pro Arg Phe Pro Pro Arg
1               5                   10

<210> SEQ ID NO 339
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 339

Arg Ile Pro Pro Glu Phe Pro Pro Arg Phe Pro Pro Arg Phe
1               5                   10

<210> SEQ ID NO 340
<211> LENGTH: 14
<212> TYPE: PRT
<213> ORGANISM: Artificial
<220> FEATURE:
<223> OTHER INFORMATION: peptide derived from cathelicidin PR-39

<400> SEQUENCE: 340

Ile Pro Pro Glu Phe Pro Pro Arg Phe Pro Pro Arg Phe Pro
1               5                   10

<210> SEQ ID NO 341
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 341

Arg Arg Arg Pro Arg Pro Pro Tyr Leu Pro Arg Pro Arg Pro Pro
1               5                   10                  15

<210> SEQ ID NO 342
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 342

Arg Arg Pro Arg Pro Pro Tyr Leu Pro Arg Pro Arg Pro Pro Pro
1               5                   10                  15

<210> SEQ ID NO 343
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 343

Arg Pro Arg Pro Pro Tyr Leu Pro Arg Pro Arg Pro Pro Pro Phe
1               5                   10                  15

<210> SEQ ID NO 344
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 344
```

```
Pro Arg Pro Pro Tyr Leu Pro Arg Pro Arg Pro Pro Phe Phe
1               5                   10                  15
```

<210> SEQ ID NO 345
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 345

```
Arg Pro Pro Tyr Leu Pro Arg Pro Arg Pro Pro Phe Phe Pro
1               5                   10                  15
```

<210> SEQ ID NO 346
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 346

```
Pro Pro Tyr Leu Pro Arg Pro Arg Pro Pro Phe Phe Pro Pro
1               5                   10                  15
```

<210> SEQ ID NO 347
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 347

```
Pro Tyr Leu Pro Arg Pro Arg Pro Pro Phe Phe Pro Pro Arg
1               5                   10                  15
```

<210> SEQ ID NO 348
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 348

```
Tyr Leu Pro Arg Pro Arg Pro Pro Phe Phe Pro Pro Arg Leu
1               5                   10                  15
```

<210> SEQ ID NO 349
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 349

```
Leu Pro Arg Pro Arg Pro Pro Phe Phe Pro Pro Arg Leu Pro
1               5                   10                  15
```

<210> SEQ ID NO 350
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 350

```
Pro Arg Pro Arg Pro Pro Phe Phe Pro Pro Arg Leu Pro Pro
1               5                   10                  15
```

```
<210> SEQ ID NO 351
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 351

Arg Pro Arg Pro Pro Pro Phe Phe Pro Pro Arg Leu Pro Pro Arg
1               5                   10                  15

<210> SEQ ID NO 352
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 352

Pro Arg Pro Pro Pro Phe Phe Pro Pro Arg Leu Pro Pro Arg Ile
1               5                   10                  15

<210> SEQ ID NO 353
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 353

Arg Pro Pro Pro Phe Phe Pro Pro Arg Leu Pro Pro Arg Ile Pro
1               5                   10                  15

<210> SEQ ID NO 354
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 354

Pro Pro Pro Phe Phe Pro Pro Arg Leu Pro Pro Arg Ile Pro Pro
1               5                   10                  15

<210> SEQ ID NO 355
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 355

Pro Pro Phe Phe Pro Pro Arg Leu Pro Pro Arg Ile Pro Pro Glu
1               5                   10                  15

<210> SEQ ID NO 356
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 356

Pro Phe Phe Pro Pro Arg Leu Pro Pro Arg Ile Pro Pro Glu Phe
1               5                   10                  15
```

```
<210> SEQ ID NO 357
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 357

Phe Phe Pro Pro Arg Leu Pro Pro Arg Ile Pro Pro Glu Phe Pro
1               5                   10                  15

<210> SEQ ID NO 358
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 358

Pro Pro Arg Leu Pro Pro Arg Ile Pro Pro Glu Phe Pro Pro Arg
1               5                   10                  15

<210> SEQ ID NO 359
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 359

Pro Pro Arg Leu Pro Pro Arg Ile Pro Pro Glu Phe Pro Pro Arg
1               5                   10                  15

<210> SEQ ID NO 360
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 360

Pro Arg Leu Pro Pro Arg Ile Pro Pro Glu Phe Pro Pro Arg Phe
1               5                   10                  15

<210> SEQ ID NO 361
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 361

Arg Leu Pro Pro Arg Ile Pro Pro Glu Phe Pro Pro Arg Phe Pro
1               5                   10                  15

<210> SEQ ID NO 362
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 362

Leu Pro Pro Arg Ile Pro Pro Glu Phe Pro Pro Arg Phe Pro Pro
1               5                   10                  15

<210> SEQ ID NO 363
<211> LENGTH: 15
```

```
<212> TYPE: PRT
<213> ORGANISM: Artificial
<220> FEATURE:
<223> OTHER INFORMATION: peptide derived from cathelicidin PR-39

<400> SEQUENCE: 363

Pro Pro Arg Ile Pro Pro Glu Phe Pro Pro Arg Phe Pro Pro Arg
1               5                   10                  15

<210> SEQ ID NO 364
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 364

Pro Arg Ile Pro Pro Glu Phe Pro Pro Arg Phe Pro Pro Arg Phe
1               5                   10                  15

<210> SEQ ID NO 365
<211> LENGTH: 15
<212> TYPE: PRT
<213> ORGANISM: Artificial
<220> FEATURE:
<223> OTHER INFORMATION: peptide derived from cathelicidin PR-39

<400> SEQUENCE: 365

Arg Ile Pro Pro Glu Phe Pro Pro Arg Phe Pro Pro Arg Phe Pro
1               5                   10                  15

<210> SEQ ID NO 366
<211> LENGTH: 3
<212> TYPE: PRT
<213> ORGANISM: Artificial
<220> FEATURE:
<223> OTHER INFORMATION: peptide derived from cathelicidin PR-39

<400> SEQUENCE: 366

Arg Pro Arg
1

<210> SEQ ID NO 367
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 367

Arg Lys Pro Arg
1

<210> SEQ ID NO 368
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 368

Thr Lys Pro Arg
1

<210> SEQ ID NO 369
<211> LENGTH: 4
<212> TYPE: PRT
<213> ORGANISM: Artificial
```

```
-continued

<220> FEATURE:
<223> OTHER INFORMATION: peptide derived from cathelicidin PR-39
<220> FEATURE:
<221> NAME/KEY: MISC_FEATURE
<222> LOCATION: (1)..(1)
<223> OTHER INFORMATION: Thr at N-terminal has N-Palmitoyl attached

<400> SEQUENCE: 369

Thr Lys Pro Arg
1

<210> SEQ ID NO 370
<211> LENGTH: 4
<212> TYPE: PRT
<213> ORGANISM: Artificial
<220> FEATURE:
<223> OTHER INFORMATION: peptide derived from cathelicidin PR-39

<400> SEQUENCE: 370

Gly Gln Pro Arg
1

<210> SEQ ID NO 371
<211> LENGTH: 4
<212> TYPE: PRT
<213> ORGANISM: Artificial
<220> FEATURE:
<223> OTHER INFORMATION: peptide derived from cathelicidin PR-39
<220> FEATURE:
<221> NAME/KEY: MISC_FEATURE
<222> LOCATION: (1)..(1)
<223> OTHER INFORMATION: Gly at N-terminal has N-Palmitoyl attached

<400> SEQUENCE: 371

Gly Gln Pro Arg
1

<210> SEQ ID NO 372
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 372

Phe Tyr Arg Pro Arg
1               5

<210> SEQ ID NO 373
<211> LENGTH: 5
<212> TYPE: PRT
<213> ORGANISM: Artificial
<220> FEATURE:
<223> OTHER INFORMATION: peptide derived from cathelicidin PR-39

<400> SEQUENCE: 373

Ala Arg Asp Pro Arg
1               5

<210> SEQ ID NO 374
<211> LENGTH: 4
<212> TYPE: PRT
<213> ORGANISM: Artificial
<220> FEATURE:
<223> OTHER INFORMATION: peptide derived from cathelicidin PR-39
<220> FEATURE:
<221> NAME/KEY: MISC_FEATURE
<222> LOCATION: (1)..(1)
<223> OTHER INFORMATION: Pro at N-terminal has N-Palmitoyl attached
```

```
<400> SEQUENCE: 374

Pro Pro Tyr Leu
1

<210> SEQ ID NO 375
<211> LENGTH: 4
<212> TYPE: PRT
<213> ORGANISM: Artificial
<220> FEATURE:
<223> OTHER INFORMATION: peptide derived from cathelicidin PR-39
<220> FEATURE:
<221> NAME/KEY: MISC_FEATURE
<222> LOCATION: (1)..(1)
<223> OTHER INFORMATION: Pro at N-terminal has N-Acetyl attached

<400> SEQUENCE: 375

Pro Pro Tyr Leu
1
```

OLIGOPEPTIDES AND THEIR USE IN COSMETICS

CROSS REFERENCES

This application claims priority to International Application No. PCT/EP2005/010893 filed Oct. 10, 2005 and published in English 27 Apr. 2006 as WO 2006/042661 A3, which claims priority from European Application No. 04292475.3 filed 18 Oct. 2004 each of which is incorporated herein by reference in its entirety.

FIELD OF THE INVENTION

The present invention relates to the cosmetic use of oligopeptides, cosmetic preparations which comprise such oligopeptides as well as certain oligopeptide derivatives themselves.

PRIOR ART

Cosmetic preparations are available nowadays to the consumer in a large number of combinations. In this regard, it is not only expected that these cosmetics exhibit a particular care effect or overcome a certain deficiency, but there is an evermore frequent requirement for products which have several properties at the same time and thus exhibit an improved performance spectrum. Of particular interest are substances which both favourably influence the technical properties of the cosmetic product, such as storage stability, photostability and ability to be formulated, and also at the same time constitute active ingredients which confer care, irritation-suppressing and/or photoprotective properties for skin and/or hair for example. Additionally, good skin compatibility and particularly the use of natural products are requested by the customer. There is a further need for effective protection of the skin against environmental ageing effects.

The human skin expresses a number of antimicrobially effective peptides, such as, for example, cathelicidin and β-defensin, during inflammation processes of the skin such as wound healing, contact dermatitis and psoriasis. It is known that these peptides in the skin construct a barrier for protecting the endogenous skin cells against microbial pathogenesis (Gallo R L & Huttner K M. *J Invest. Dermatol.* 1998, 111, 739-43). The peptide cathelicidin PR39 was identified for the first time in wound fluid of pigs through the induction of syndecan (Gallo R.-L., *Proc Natl. Acad. Sci.* USA, 1994, 91, 11035-11039). Supplementary to this prior art, it is reported that in the case of fragment 1-15 of PR39 the antimicrobial properties of the peptide remain completely intact. It was shown that the interaction of the fragment with the lipid double layer is identical to the complete peptide and that the fragment binds with SH3-containing proteins (Chan Y. R., Gallo R. L., *J. Biol. Chem.* 1998, 273, 28978-28985). The same team was then able to show that the N-terminal region is important for peptide activity and specifically for the syndecan induction and the antimicrobial activity and that the C-terminal region is of greater importance for the antibacterial properties (Chan Y. R., Gallo R. L., *J. Invest. Dermat.* 2001, 116, 230-235).

WO 01/47540 describes a method for selectively inhibiting degradation of IkBa using oligopeptides of PR-39. The following oligopeptides of PR-39 are disclosed: the oligopeptide consisting of the 15 aminoterminal amino acids, the oligopeptide consisting of the 11 aminoterminal amino acids, and the oligopeptide consisting of the 8 aminoterminal amino acids. WO 01/30368 describes a method for stimulating angiogenesis with oligopeptides of PR-39 using the oligopeptides as described in WO 01/47540. Gallo R L et al. PNAS 91, 11035-39 (1994) describes the antibacterial activity of the peptide PR39 and its ability to induce syndecan. Gaczynska M et al Biochemistry, 2003, 42, 8663-8670 describes that the shortest functional derivative from PR 39 to still show allosteric inhibitory effects consist of eleven amino-terminal residues. Zaiou M & Gallo R L J Mol Med 80, 549-61 (2002) review the different know activities of PR-39, e.g. induction of syndecan expression, chemoattractant activity etc. Gudmundsson G. et al PCNAS 92, 7085-89 (1995) describes the gene for PR-39.

U.S. Pat. No. 6,713,605 (WO 96/32129) describes PR-39 and truncated analogs consisting of 26, 23, 19, 16, 15, 14, 7 and 6 amino acids of PR-39 and their use as medicaments for inhibiting leucocyte superoxide anion production. WO 00/43417 describes peptides H-Arg-Pro-(AA)$_n$-OH or H-Pro-Arg-(AA)$_n$-OH, wherein n=0 to 3. WO 00/43317 describes the use of these penta-petides for the regulation of immunological dysfunction and in cutaneous inflammation. Specifically disclosed are the following peptides: Arg Pro Arg (Seq. ID No. 366), Arg Lys Pro Arg (Seq. ID No. 367), Thr Lys Pro Arg (Seq. ID No. 368), N-Palmitoyl-Thr Lys Pro Arg (Seq. ID No. 369), Gly Gln Pro Arg (Seq. ID No. 370), N-Palmitoyl-Gly Gln Pro Arg (Seq. ID No. 371), Phe-Tyr-Arg-Pro-Arg (Seq. ID No. 372), Ala-Arg-Asp-Pro-Arg. ID No. 373).

Cosmetic preparations comprising peptides with a large number of amino acids, such as, for example, the entire cathelicidin PR-39, are not practicable and sometimes also not realizable because the production of this type of peptides on an industrial scale is very difficult and very expensive.

The object of the present patent application was to provide cosmetic preparations which lead to protection of the skin, scalp, mucosa and/or hair against environmental effects, oxidative stress, toxic substances or UV radiation and to a stimulation of the renewal rate of skin and/or hair and can thus be used effectively in cosmetics for topical application. It was also an object of the present invention to provide oligopeptides as well as cosmetic preparations having the above mentioned specified profile of requirements and at the same time the shortest possible number of amino acids.

Surprisingly, it has now been found that oligopeptides comprising amino acids of the peptide cathelicidin PR-39 satisfy the requirements made.

None of the document of the prior art describes oligopeptides of the invention nor the cosmetic use of the claimed oligopeptides. None of the documents describes oligopeptides which can be used for stimulating the renewal rate of skin and/or hair or cosmetic compositions comprising oligopeptides with such a profile.

DESCRIPTION OF THE INVENTION

Cosmetic Use of Oligopeptide of Formula (I)

The current invention relates to the cosmetic use of oligopeptides with the structure of formula (I)

$$R1-[AA]_n-R2 \qquad (I)$$

wherein [AA] comprises at least 4 consecutive amino acids, which are identical compared to 4 consecutive amino acids of SEQ ID No. 1 and/or wherein [AA] comprises at least 6 amino acids, of which 4, preferably 5 are identical compared to 6 consecutive amino acids of SEQ ID No. 1 wherein n=4 to 15, preferably n=4 to 10 wherein R1 is linked to the NH$_2$-group of the amino-terminal part of [AA] and is chosen from the group which is formed from
a) —H,
b) a linear saturated or unsaturated or branched saturated or unsaturated acyl group having 1 to 24 carbon atoms, which may be functionalized by a —OH, —SH, —COOH or —CONH$_2$ group,
c) a sterol or a spingolipid group which is joined to the amino terminal part of [AA] via a bifunctional linker wherein R2 is linked to the C═O group of the carboxy-terminal part of [AA] and is chosen from the group which is formed from
a) —OH,
b) —NH$_2$
c) a linear saturated or unsaturated or branched saturated or unsaturated alkoxy group having 1 to 24 carbon atoms
d) or a sterol or a shpingolipid group.

The term "oligopeptide" encompasses single species of formula (I) as well as mixtures of at least 2, at least 3 or more oligopeptides of formula (I).

Oligopeptide (I)

A further embodiment of the invention is directed to oligopeptides with the structure of formula (I)

R1-[AA]$_n$-R2  (I)

wherein [AA] comprises at least 4 consecutive amino acids, which are identical compared to 4 consecutive amino acids of SEQ ID No. 1 and/or wherein [AA] comprises at least 6 amino acids, of which 4, preferably 5, more preferably 6 are identical compared to 6 consecutive amino acids of SEQ ID No. 1
wherein n=4 to 15
wherein R1 is linked to the NH$_2$-group of the amino-terminal part of [AA] and is chosen from the group consisting of
a) —H,
b) is a linear saturated or unsaturated or branched saturated or unsaturated acyl group having 1 to 24 carbon atoms, which may be functionalised by a —OH, —SH, —COOH or —CONH$_2$ group,
c) a sterol or a spingolipid group which is joined to the amino terminal part of [AA] via a bifunctional linker wherein R2 is linked to the C═O group of the carboxy-terminal part of [AA] and is chosen from the group which is formed from
a) —OH,
b) —NH$_2$
c) is a linear saturated or unsaturated or branched saturated or unsaturated alkoxy group having 1 to 24 carbon atoms, which may be functionalised by a —OH, —SH, —COOH or —CONH$_2$ group, or
d) a sterol or a shingolipid group,
with the proviso that if R1 is —H, R2 is not —OH; or that if R2 is —OH, R1 is not —H, and
with the proviso that if R1 is —H, R2 is chosen form the group which is formed from
b) —NH2
c) —a linear saturated or unsaturated or branched saturated or unsaturated alkoxy group having 2 to 24 carbon atoms, or
d) a sterol or a sphingolipid group, These oligopeptides are especially useful in cosmetic preparations.

The total number of amino acids in the oligopeptide (=n) be any number between 4 and 15, thus n can be 4, 5, 6, 7, 8, 9, 10, 11, 12, 13, 14 or 15. In a preferred embodiment the total number of amino acids is at most 15, preferably at most 12, preferably at most 10, preferably at most 8, preferably at most 6, preferably at most 5.

The terms "oligopeptide" and "oligopeptides" are used synonymously to encompass single oligopeptide species of formula (I) as well as mixtures of at least 2, at least 3, or more oligopeptides according to formula (I). In case where at least R1 is not ═H or R2 is not —OH, the term "oligopeptide derivative" would be a more precise term. As used in this description, the term "oligopeptide" or "oligopeptides" encompasses oligopeptides as well as oligopeptide derivatives as well as salt of the oligopeptides as well as salts of the oligopeptide derivatives.

In a further embodiment of the invention, oligopeptides which are able to stimulate the growth of human keratinocytes in-vitro are preferred.

This ability can be tested in standard assays using human primary keratinocytes, which can be obtained by trypsinization of human skin biopsis. These are cultured in standard medium under standard conditions prior to the cultivation of the oligopeptide to be tested. Ususal cultivation with the oligopeptide to be tested are 37° C., 4 or 5 days.

The stimulation of the proliferation can be determined by measuring the number of living cells in a sample cultivated with the oligopeptide to be tested in comparison to control (=no peptide). The number of living cells can for example be determined by measuring the DNA content, e.g. by fluorescence methods.

A stimulation of the proliferation is preferably achieved, if 5% more DNA is detected, preferably 10% more, even more preferably 15% more, even more preferably 20% more DNA when compared to the DNA content of the control.

Cosmetic Use

It has been found that the oligopeptides according to the invention are especially useful for producing a preparation which is effective against the formation of wrinkles and/or for reducing the severity of wrinkles and/or against the loss of elasticity of the skin and/or for strengthening the cutaneous barrier and/or dermis and/or the dermal-epidermal junction (DEJ) and/or for reducing the skin dryness and/or for reducing the "orange skin" phenomenon of subcutaneous tissue. The oligopeptides according to formula (I) are preferably used for stimulating the renewal rate of skin and/or hair. They are preferably useful in cosmetic preparations against the reduction in cell numbers in human skin or for stimulating and/or regenerating hair growth and against hair loss.

It has surprisingly been found that the oligopeptides according to the invention are useful in strengthening of the cutaneous barrier and reducing the skin dryness at the same time.

In one embodiment, the oligopeptide according to the invention are useful for the cosmetic treatment of
a. human skin or hair ageing and/or
b. for preventing against ageing symptoms, such as wrinkles, and/or
c. decrease of the epidermal and dermal skin layers, and/or
d. alterations of the extracellular matrix and/or decrease in the renewal of epidermal and dermal cells and/or
e. modifications of the dermal epidermal junctions and/or
f. loss of elasticity and/or
g. hair damages and/or hair losses.

In one embodiment, the oligopeptide according to the invention are preferably useful for
h. stimulation of the renewal rate of human skin and/or hair.

In a preferred embodiment, the oligopeptide according to the invention are used for cosmetic preparations which are effective
i. for stimulating the production of mRNA and/or
j. for stimulation of matrix proteins such as collagen, elastin or proteoglycans and/or
k. for stimulation of syndecan-1 synthesis It has surprisingly been found, that the oligopeptides according to this invention are especially useful in cosmetic compositions for stimulating syndecan-1 synthesis.

In a preferred embodiment, the oligopeptides according to the invention, are used for producing a preparation which is effective against the formation of wrinkles and for reducing the severity of wrinkles or against the loss of elasticity of the skin or for strengthening the cutaneous barrier and/or the dermis and/or the dermal-epidermal junction (DEJ) or for reducing the "orange skin" phenomenon of subcutaneous tissue or for improved wound healing or against the reduction in cell numbers in human skin.

In one embodiment of the invention the oligopeptides according to the invention are used for stimulating and/or regenerating hair growth and against hair loss.

In a preferred embodiment of the invention the oligopeptides are used in cosmetic preparations which stimulate the growth and the differentiation of human primary keratinocytes, which strengthen the skin barrier function. Preferably the oligopeptides according to the invention can be used effectively as inhibitors of elastase, the enzyme which degrades elastin.

[AA] Moiety: Tetrapeptide

In one embodiment of the invention, [AA] consists of 4 consecutive amino acids, which are identical to 4 consecutive amino acids of SEQ ID No. 1.

Table 1 list these tetra-peptides:

In a preferred embodiment [AA] consists of a tetra-peptide as specified in column I of table 1.

In a preferred embodiment [AA] consists of a tetra-peptide selected from the group consisting of

| | | |
|---|---|---|
| i) | Arg Arg Arg Pro; | (Seq. ID No. 2) |
| | Arg Arg Pro Arg; | (Seq. ID No. 3) |
| ii) | Arg Pro Pro Tyr; | (Seq. ID No. 6) |
| | Pro Pro Tyr Leu; preferably | (Seq. ID No. 7) |
| | Pro Pro Tyr Leu; | (Seq. ID No. 7) |
| iii) | Pro Tyr Leu Pro; | (Seq. ID No. 8) |
| | Tyr Leu Pro Arg; or | (Seq. ID No. 9) |
| iv) | Tyr Leu Pro Arg; | (Seq. ID No. 9) |
| | Leu Pro Arg Pro; | (Seq. ID No. 10) |

In a further embodiment the oligopeptide consists of at most 15, preferably at most 10, more preferably at most 5 amino acids, of which at least 4 consecutive amino acids are identical to 4 consecutive amino acids of SEQ ID No. 1. Thus in one embodiment of the invention, [AA] comprises 4 consecutive amino acids which are identical to 4 consecutive amino acids of SEQ ID No. 1 and has up to 11 further amino acids (resulting in a total number of 15 amino acids), preferably up to 6 further amino acids (resulting in a total number of 10 amino acids), more preferably up to 1 further amino acid (resulting in a total number of 5 amino acids), whereas the further amino acids need not be identical to or even present in SEQ ID No. 1.

In this embodiment [AA] is thus $[X_m\text{-aa-}Y_o]$, wherein aa is a tetra-peptide of table 1 and X and Y are further amino acids, m and o being numbers from 0 to 11, with the proviso that

| 36 tetra peptides of 4 consecutive amino acids of SEQ ID No. 1 | | | | | |
|---|---|---|---|---|---|
| Seq. ID No. | Column I | Seq. ID No. | Column II | Seq. ID No. | Column III |
| Seq. ID No. 2 | Arg Arg Arg Pro | Seq. ID No. 14 | Arg Pro Pro Pro | Seq. ID No. 26 | Arg Ile Pro Pro |
| Seq. ID No. 3 | Arg Arg Pro Arg | Seq. ID No. 15 | Pro Pro Pro Phe | Seq. ID No. 27 | Ile Pro Pro Glu |
| Seq. ID No. 4 | Arg Pro Arg Pro | Seq. ID No. 16 | Pro Pro Phe Phe | Seq. ID No. 28 | Pro Pro Glu Phe |
| Seq. ID No. 5 | Pro Arg Pro Pro | Seq. ID No. 17 | Pro Phe Phe Pro | Seq. ID No. 29 | Pro Glu Phe Pro |
| Seq. ID No. 6 | Arg Pro Pro Tyr | Seq. ID No. 18 | Phe Phe Pro Pro | Seq. ID No. 30 | Glu Phe Pro Pro |
| Seq. ID No. 7 | Pro Pro Tyr Leu | Seq. ID No. 19 | Phe Pro Pro Arg | Seq. ID No. 31 | Phe Pro Pro Arg |
| Seq. ID No. 8 | Pro Tyr Leu Pro | Seq. ID No. 20 | Pro Pro Arg Leu | Seq. ID No. 32 | Pro Pro Arg Phe |
| Seq. ID No. 9 | Tyr Leu Pro Arg | Seq. ID No. 21 | Pro Arg Leu Pro | Seq. ID No. 33 | Pro Arg Phe Pro |
| Seq. ID No. 10 | Leu Pro Arg Pro | Seq. ID No. 22 | Arg Leu Pro Pro | Seq. ID No. 34 | Arg Phe Pro Pro |
| Seq. ID No. 11 | Pro Arg Pro Arg | Seq. ID No. 23 | Leu Pro Pro Arg | Seq. ID No. 35 | Phe Pro Pro Arg |
| Seq. ID No. 12 | Arg Pro Arg Pro | Seq. ID No. 24 | Pro Pro Arg Ile | Seq. ID No. 36 | Pro Pro Arg Phe |
| Seq. ID No. 13 | Pro Arg Pro Pro | Seq. ID No. 25 | Pro Arg Ile Pro | Seq. ID No. 37 | Pro Arg Phe Pro | m+o is ≦11. In a preferred embodiment, aa is selected from the tetra-peptides as specified in column 1 of table 1. In a further preferred embodiment m+o is ≦6, preferably =1.

In a preferred embodiment [AA] comprises a tetra-peptide as specified in column I of table 1.

In a preferred embodiment [AA] comprises a tetra-peptide selected from the group consisting of:

| | | |
|---|---|---|
| i) | Arg Arg Arg Pro; | (Seq. ID No. 2) |
| | Arg Arg Pro Arg; | (Seq. ID No. 3) |
| ii) | Arg Pro Pro Tyr; | (Seq. ID No. 6) |
| | Pro Pro Tyr Leu, preferably | (Seq. ID No. 7) |
| | Pro Pro Tyr Leu; | (Seq. ID No. 7) |
| iii) | Pro Tyr Leu Pro; | (Seq. ID No. 8) |
| | Tyr Leu Pro Arg; or | (Seq. ID No. 9) |
| iv) | Tyr Leu Pro Arg; | (Seq. ID No. 9) |
| | Leu Pro Arg Pro. | (Seq. ID No. 10) |

The further amino acids can be any of the known proteinogenic amino acids including selenocystein (Sec) and L-pyrrolysine, derivatives of the proteinogenic amino acids or non-proteinogenic amino acids, e.g. L-citrullin. L-homocysteine, L-homoserine, (4R)-4-hydroxy-L-prolin, L-Homoserin (Hse), (4R)-4-Hydroxy-L-proline (Hyp), (5R)-5-Hydroxy-L-lysine (Hyl), L-ornithine (Orn), sarkosine to name only a few. Functional groups of the further amino acids can be derivatised, e.g. by linear saturated or unsaturated or branched saturated or unsaturated acyl group having 1 to 24 carbon atoms, by functional groups such as a —OH, —SH, —COOH or —CONH$_2$ group.

The amino acids can be either in D- or in L-configuration.

In a further embodiment of the invention [AA] comprises at most 14, preferably at most 13, preferably at most 13, preferably at most 12, more preferably at most 10, preferably at most 9, preferably at most 8, preferably at most 7, preferably at most 6, preferably at most 5 consecutive amino acids identical to the respective amino acids of the amino acid sequence of SEQ ID No. 1.

In a preferred embodiment of the invention [AA] consists of at most 15, preferably at most 14, preferably at most 13, preferably at most 13, preferably at most 12, more preferably at most 10, preferably at most 9, preferably at most 8, preferably at most 7, preferably at most 6, preferably at most 5 consecutive amino acids identical to the respective amino acids of the amino acid sequence of SEQ ID No. 1.

[AA] Moiety: Pentapeptide

In a further embodiments of the invention [AA] comprises at least 5, at least 6, at least 7, at least 8, at least 9, at least 10, at least 11, at least 12, at least 13, at least 14 or consists of 15 consecutive amino acids which are identical to the respective number of amino acids of SEQ ID No. 1.

In a further embodiments of the invention [AA] consists of at least 5, at least 6, at least 7, at least 8, at least 9, at least 10, at least 11, at least 12, at least 13, at least 14 consecutive amino acids which are identical to the respective number of amino acids of SEQ ID No. 1.

In one embodiment of the invention, [AA] consists of 5 consecutive amino acids, which are identical to 5 consecutive amino acids of SEQ ID No. 1.

TABLE 2

35 penta-peptides of 5 consecutive amino acids of SEQ ID NO. 1

| Seq. ID No. | Column I | Seq. ID No. | Column II | Seq. ID No. | Column III |
|---|---|---|---|---|---|
| Seq. ID No. 38 | Arg Arg Arg Pro Arg | Seq. ID No. 49 | Pro Arg Pro Pro Pro | Seq. ID No. 60 | Pro Pro Arg Ile Pro |
| Seq. ID No. 39 | Arg Arg Pro Arg Pro | Seq. ID No. 50 | Arg Pro Pro Pro Phe | Seq. ID No. 61 | Pro Arg Ile Pro Pro |
| Seq. ID No. 40 | Arg Pro Arg Pro Pro | Seq. ID No. 51 | Pro Pro Pro Phe Phe | Seq. ID No. 62 | Arg Ile Pro Pro Glu |
| Seq. ID No. 41 | Pro Arg Pro Pro Tyr | Seq. ID No. 52 | Pro Pro Phe Phe Pro | Seq. ID No. 63 | Ile Pro Pro Glu Phe |
| Seq. ID No. 42 | Arg Pro Pro Tyr Leu | Seq. ID No. 53 | Pro Phe Phe Pro Pro | Seq. ID No. 64 | Pro Pro Glu Phe Pro |
| Seq. ID No. 43 | Pro Pro Tyr Leu Pro | Seq. ID No. 54 | Phe Phe Pro Pro Arg | Seq. ID No. 65 | Pro Glu Phe Pro Pro |
| Seq. ID No. 44 | Pro Tyr Leu Pro Arg | Seq. ID No. 55 | Phe Pro Pro Arg Leu | Seq. ID No. 66 | Glu Phe Pro Pro Arg |
| Seq. ID No. 45 | Tyr Leu Pro Arg Pro | Seq. ID No. 56 | Pro Pro Arg Leu Pro | Seq. ID No. 67 | Phe Pro Pro Arg Phe |
| Seq. ID No. 46 | Leu Pro Arg Pro Arg | Seq. ID No. 57 | Pro Arg Leu Pro Pro | Seq. ID No. 68 | Pro Pro Arg Phe Pro |
| Seq. ID No. 47 | Pro Arg Pro Arg Pro | Seq. ID No. 58 | Arg Leu Pro Pro Arg | Seq. ID No. 69 | Pro Arg Phe Pro Pro |
| Seq. ID No. 48 | Arg Pro Arg Pro Pro | Seq. ID No. 59 | Leu Pro Pro Arg Ile | Seq. ID No. 70 | Arg Phe Pro Pro Arg |
| | | | | Seq. ID No. 71 | Phe Pro Pro Arg Phe |
| | | | | Seq. ID No. 72 | Pro Pro Arg Phe Pro |

In a preferred embodiment [AA] consists of a penta-peptide as specified in column I of table 2.

In a preferred embodiment [AA] consists of a penta-peptide selected from the group consisting of Arg Arg Arg Pro Arg (Seq. ID No. 38); Arg Pro Pro Tyr Leu (Seq. ID No. 42); Pro Tyr Leu Pro Arg (Seq. ID No. 44); and Tyr Leu Pro Arg Pro (Seq. ID No. 45).

In a further embodiment the oligopeptide consists of at most 15, preferably at most 10, more preferably at most 7 amino acids, of which 5 consecutive amino acids are identical to 5 consecutive amino acids of SEQ ID No. 1; Thus in one embodiment of the invention, [AA] comprises 5 consecutive amino acids which are identical to 5 consecutive amino acids of SEQ ID No. 1 and has up to 10 further amino acids (resulting in a total number of 15 amino acids), preferably up to 5 further amino acids (resulting in a total number of 10 amino acids), preferably up to 2 further amino acids (resulting in a total number of 7 amino acids) whereas the further amino acids need not be identical to or even present in SEQ ID No. 1.

In this embodiment [AA] is thus [$X_m$-aa-$Y_o$], wherein aa is a penta-peptide of table 2, and X and Y are further amino acids, m and o being numbers from 0 to 10, with the proviso that m+o is $\leq 10$. In a preferred embodiment, aa is selected from the penta-peptide as specified in column 1 of table 2. In a further preferred embodiment m+o is $\leq 5$, more preferably $\leq 2$.

In a preferred embodiment [AA] comprises a penta-peptide as specified in column I of table 2.

In a preferred embodiment [AA] comprises a penta-peptide selected from the group consisting of Arg Arg Arg Pro Arg (Seq. ID No. 38); Arg Pro Pro Tyr Leu (Seq. ID No. 42); Pro Tyr Leu Pro Arg (Seq. ID No. 44) and Tyr Leu Pro Arg Pro (Seq. ID No. 45).

[AA] Moiety: Hexapapetide

In one embodiment of the invention, [AA] consists of 6 consecutive amino acids, which are identical to 6 consecutive amino acids of SEQ ID No. 1.

In a preferred embodiment [AA] consists of a hexa-peptide as specified in column I of table 3.

In a further embodiment of the oligopeptide consists of at most 15, preferably at most 10, more preferably at most 8 amino acids, of which 6 consecutive amino acids are identical to 6 consecutive amino acids of SEQ ID No. 1; Thus in one embodiment of the invention, [AA] comprises 6 consecutive amino acids which are identical to 6 consecutive amino acids of SEQ ID No. 1 and has up to 9 further amino acids (resulting in a total number of 15 amino acids), preferably up to 5 further amino acids (resulting in a total number of 10 amino acids), preferably up to 2 further amino acids (resulting in a total number of 8 amino acids) whereas the further amino acids need not be identical to or even present in SEQ ID No. 1.

In this embodiment [AA] is thus [$X_m$-aa-$Y_o$], wherein aa is a hexa-peptide of table 3, and X and Y are further amino acids, m and o being numbers from 0 to 9, with the proviso that m+o is $\leq 9$. In a preferred embodiment, aa is selected from the hexa-peptide as specified in column 1 of table 3. In a further preferred embodiment m+o is $\leq 4$, more preferably $\leq 2$.

[AA] Moiety: Heptapeptide

In one embodiment of the invention, [AA] consists of 7 consecutive amino acids, which are identical to 7 consecutive amino acids of SEQ ID No. 1.

TABLE 3

34 hexa-peptides of 6 consecutive amino acids of SEQ ID NO. 1

| Column I | Column II | Column III |
|---|---|---|
| Seq. ID No. 73 Arg Arg Arg Pro Arg Pro | Seq. ID No. 83 Arg Pro Arg Pro Pro Pro | Seq. ID No. 93 Arg Leu Pro Pro Arg Ile |
| Seq. ID No. 74 Arg Arg Pro Arg Pro Pro | Seq. ID No. 84 Pro Arg Pro Pro Pro Phe | Seq. ID No. 94 Leu Pro Pro Arg Ile Pro |
| Seq. ID No. 75 Arg Pro Arg Pro Pro Tyr | Seq. ID No. 85 Arg Pro Pro Pro Phe Phe | Seq. ID No. 95 Pro Pro Arg Ile Pro Pro |
| Seq. ID No. 76 Pro Arg Pro Pro Tyr Leu | Seq. ID No. 86 Pro Pro Pro Phe Phe Pro | Seq. ID No. 96 Pro Arg Ile Pro Pro Glu |
| Seq. ID No. 77 Arg Pro Pro Tyr Leu Pro | Seq. ID No. 87 Pro Pro Phe Phe Pro Pro | Seq. ID No. 97 Arg Ile Pro Pro Glu Phe |
| Seq. ID No. 78 Pro Pro Tyr Leu Pro Arg | Seq. ID No. 88 Pro Phe Phe Pro Pro Arg | Seq. ID No. 98 Ile Pro Pro Glu Phe Pro |
| Seq. ID No. 79 Pro Tyr Leu Pro Arg Pro | Seq. ID No. 89 Phe Phe Pro Pro Arg Leu | Seq. ID No. 99 Pro Pro Glu Phe Pro Pro |
| Seq. ID No. 80 Tyr Leu Pro Arg Pro Arg | Seq. ID No. 90 Phe Pro Pro Arg Leu Pro | Seq. ID No. 100 Pro Glu Phe Pro Pro Arg |
| Seq. ID No. 81 Leu Pro Arg Pro Arg Pro | Seq. ID No. 91 Pro Pro Arg Leu Pro Pro | Seq. ID No. 101 Glu Phe Pro Pro Arg Phe |
| Seq. ID No. 82 Pro Arg Pro Arg Pro Pro | Seq. ID No. 92 Pro Arg Leu Pro Pro Arg | Seq. ID No. 102 Phe Pro Pro Arg Phe Pro |
| | | Seq. ID No. 103 Pro Pro Arg Phe Pro Pro |
| | | Seq. ID No. 104 Pro Arg Phe Pro Pro Arg |
| | | Seq. ID No. 105 Arg Phe Pro Pro Arg Phe |
| | | Seq. ID No. 106 Phe Pro Pro Arg Phe Pro |

Table 4 list these hepta-peptides:

| | | | | Seq. ID No. | |
|---|---|---|---|---|---|
| Seq. ID No. | Column I | Seq. ID No. | Column II | | Column III |
| Seq. ID No. 107 | Arg Arg Arg Pro Arg Pro Pro | Seq. ID No. 116 | Pro Arg Pro Arg Pro Pro Pro | Seq. ID No. 125 | Pro Pro Arg Leu Pro Pro Arg |
| Seq. ID No. 108 | Arg Arg Pro Arg Pro Pro Tyr | Seq. ID No. 117 | Arg Pro Arg Pro Pro Pro Phe | Seq. ID No. 126 | Pro Arg Leu Pro Pro Arg Ile |
| Seq. ID No. 109 | Arg Pro Arg Pro Pro Tyr Leu | Seq. ID No. 118 | Pro Arg Pro Pro Pro Phe Phe | Seq. ID No. 127 | Arg Leu Pro Pro Arg Ile Pro |
| Seq. ID No. 110 | Pro Arg Pro Pro Tyr Leu Pro | Seq. ID No. 119 | Arg Pro Pro Pro Phe Phe Pro | Seq. ID No. 128 | Leu Pro Pro Arg Ile Pro Pro |
| Seq. ID No. 111 | Arg Pro Pro Tyr Leu Pro Arg | Seq. ID No. 120 | Pro Pro Pro Phe Phe Pro Pro | Seq. ID No. 129 | Pro Pro Arg Ile Pro Pro Glu |
| Seq. ID No. 112 | Pro Pro Tyr Leu Pro Arg Pro | Seq. ID No. 121 | Pro Pro Phe Phe Pro Pro Arg | Seq. ID No. 130 | Pro Arg Ile Pro Pro Glu Phe |
| Seq. ID No. 113 | Pro Tyr Leu Pro Arg Pro Arg | Seq. ID No. 122 | Pro Phe Phe Pro Pro Arg Leu | Seq. ID No. 131 | Arg Ile Pro Pro Glu Phe Pro |
| Seq. ID No. 114 | Tyr Leu Pro Arg Pro Arg Pro | Seq. ID No. 123 | Phe Phe Pro Pro Arg Leu Pro | Seq. ID No. 132 | Ile Pro Pro Glu Phe Pro Pro |
| Seq. ID No. 115 | Leu Pro Arg Pro Arg Pro Pro | Seq. ID No. 124 | Phe Pro Pro Arg Leu Pro Pro | Seq. ID No. 133 | Pro Pro Glu Phe Pro Pro Arg |
| | | | | Seq. ID No. 134 | Pro Glu Phe Pro Pro Arg Phe |
| | | | | Seq. ID No. 135 | Glu Phe Pro Pro Arg Phe Pro |
| | | | | Seq. ID No. 136 | Phe Pro Pro Arg Phe Pro Pro |
| | | | | Seq. ID No. 137 | Pro Pro Arg Phe Pro Pro Arg |
| | | | | Seq. ID No. 138 | Pro Arg Phe Pro Pro Arg Phe |
| | | | | Seq. ID No. 139 | Arg Phe Pro Pro Arg Phe Pro |

In a preferred embodiment [AA] consists of a heptapeptide as specified in column I of table 4.

In a further embodiment the oligopeptide consists of at most 15, preferably at most 10, more preferably at most 9 amino acids, of which at least 7 consecutive amino acids are identical to 7 consecutive amino acids of SEQ ID No. 1. Thus in one embodiment of the invention, [AA] comprises 7 consecutive amino acids which are identical to 7 consecutive amino acids of SEQ ID No. 1 and has up to 8 further amino acids (resulting in a total number of 15 amino acids), preferably up to 3 further amino acids (resulting in a total number of 10 amino acids), more preferably up to 2 further amino acid (resulting in a total number of 9 amino acids), whereas the further amino acids need not be identical to or even present in SEQ ID No. 1.

In this embodiment [AA] is thus $[X_m\text{-aa-}Y_o]$, wherein aa is a hepta-peptide of table 4 and X and Y are further amino acids, m and o being numbers from 0 to 8, with the proviso that m+o is $\leq 8$. In a preferred embodiment, aa is selected from the hepta-peptides as specified in column 1 of table 4. In a further preferred embodiment m+o is $\leq 3$, preferably =2.

[AA] Moiety: Octapeptide

In one embodiment of the invention, [AA] consists of 8 consecutive amino acids, which are identical to 8 consecutive amino acids of SEQ ID No. 1.

Table 5 list these octa-peptides:

| 32 octa-peptides of 8 consecutive amino acids of SEQ ID No. 1 | | | |
|---|---|---|---|
| Seq. ID No. | Column I | Seq. ID No. | Column II |
| Seq. ID No. 140 | Arg Arg Arg Pro Arg Pro Pro Tyr | Seq. ID No. 148 | Leu Pro Arg Pro Arg Pro Pro Pro |
| Seq. ID No. 141 | Arg Arg Pro Arg Pro Pro Tyr Leu | Seq. ID No. 149 | Pro Arg Pro Arg Pro Pro Pro Phe |
| Seq. ID No. 142 | Arg Pro Arg Pro Pro Tyr Leu Pro | Seq. ID No. 150 | Arg Pro Arg Pro Pro Pro Phe Phe |
| Seq. ID No. 143 | Pro Arg Pro Pro Tyr Leu Pro Arg | Seq. ID No. 151 | Pro Arg Pro Pro Pro Phe Phe Pro |
| Seq. ID No. 144 | Arg Pro Pro Tyr Leu Pro Arg Pro | Seq. ID No. 152 | Arg Pro Pro Pro Phe Phe Pro Pro |
| Seq. ID No. 145 | Pro Pro Tyr Leu Pro Arg Pro Arg | Seq. ID No. 153 | Pro Pro Pro Phe Phe Pro Pro Arg |
| Seq. ID No. 146 | Pro Tyr Leu Pro Arg Pro Arg Pro | Seq. ID No. 154 | Pro Pro Phe Phe Pro Pro Arg Leu |
| Seq. ID No. 147 | Tyr Leu Pro Arg Pro Arg Pro Pro | Seq. ID No. 155 | Pro Phe Phe Pro Pro Arg Leu Pro |
| | | Seq. ID No. 156 | Phe Phe Pro Pro Arg Leu Pro Pro |
| | | Seq. ID No. 157 | Phe Pro Pro Arg Leu Pro Pro Arg |
| | | Seq. ID No. 158 | Pro Pro Arg Leu Pro Pro Arg Ile |
| | | Seq. ID No. 159 | Pro Arg Leu Pro Pro Arg Ile Pro |
| | | Seq. ID No. 160 | Arg Leu Pro Pro Arg Ile Pro Pro |
| | | Seq. ID No. 161 | Leu Pro Pro Arg Ile Pro Pro Glu |
| | | Seq. ID No. 162 | Pro Pro Arg Ile Pro Pro Glu Phe |
| | | Seq. ID No. 163 | Pro Arg Ile Pro Pro Glu Phe Pro |
| | | Seq. ID No. 164 | Arg Ile Pro Pro Glu Phe Pro Pro |
| | | Seq. ID No. 165 | Ile Pro Pro Glu Phe Pro Pro Arg |
| | | Seq. ID No. 166 | Pro Pro Glu Phe Pro Pro Arg Phe |
| | | Seq. ID No. 167 | Pro Glu Phe Pro Pro Arg Phe Pro |
| | | Seq. ID No. 168 | Glu Phe Pro Pro Arg Phe Pro Pro |
| | | Seq. ID No. 169 | Phe Pro Pro Arg Phe Pro Pro Arg |
| | | Seq. ID No. 170 | Pro Pro Arg Phe Pro Pro Arg Phe |
| | | Seq. ID No. 171 | Pro Arg Phe Pro Pro Arg Phe Pro |

In a preferred embodiment [AA] consists of an octapeptide as specified in column I of table 5.

In a further embodiment the oligopeptide consists of at most 15, preferably at most 10 amino acids, of which at least 8 consecutive amino acids are identical to 8 consecutive amino acids of SEQ ID No. 1. Thus in one embodiment of the invention, [AA] comprises 8 consecutive amino acids which are identical to 8 consecutive amino acids of SEQ ID No. 1 and has up to 7 further amino acids (resulting in a total number of 15 amino acids), preferably up to 2 further amino acids (resulting in a total number of 10 amino acids), whereas the further amino acids need not be identical to or even present in SEQ ID No. 1.

In this embodiment [AA] is thus [$X_m$-aa-$Y_o$], wherein aa is a octa-peptide of table 5 and X and Y are further amino acids, m and o being numbers from 0 to 7, with the proviso that m+o is $\leq 7$. In a preferred embodiment, aa is selected from the octa-peptides as specified in column I of table 5. In a further preferred embodiment m+o is $\leq 2$.

[AA] Moiety: Nonapeptide

In one embodiment of the invention, [AA] consists of 9 consecutive amino acids, which are identical to 9 consecutive amino acids of SEQ ID No. 1.

Table 6 list these nona-peptides:

| 31 nona peptides of 9 consecutive amino acids of SEQ ID No. 1 | |
|---|---|
| Seq. ID No. | Column I |
| Seq. ID No. 172 | Arg Arg Arg Pro Arg Pro Pro Tyr Leu |

| 31 nona peptides of 9 consecutive amino acids of SEQ ID No. 1 | |
|---|---|
| Seq. ID No. 173 | Arg Arg Pro Arg Pro Pro Tyr Leu Pro |
| Seq. ID No. 174 | Arg Pro Arg Pro Pro Tyr Leu Pro Arg |
| Seq. ID No. 175 | Pro Arg Pro Pro Tyr Leu Pro Arg Pro |
| Seq. ID No. 176 | Arg Pro Pro Tyr Leu Pro Arg Pro Arg |
| Seq. ID No. 177 | Pro Pro Tyr Leu Pro Arg Pro Arg Pro |
| Seq. ID No. 178 | Pro Tyr Leu Pro Arg Pro Arg Pro Pro |

| Column II | |
|---|---|
| Seq. ID No. 179 | Tyr Leu Pro Arg Pro Arg Pro Pro Pro |
| Seq. ID No. 180 | Leu Pro Arg Pro Arg Pro Pro Pro Phe |
| Seq. ID No. 181 | Pro Arg Pro Arg Pro Pro Pro Phe Phe |
| Seq. ID No. 182 | Arg Pro Arg Pro Pro Pro Phe Phe Pro |
| Seq. ID No. 183 | Pro Arg Pro Pro Pro Phe Phe Pro Pro |
| Seq. ID No. 184 | Arg Pro Pro Pro Phe Phe Pro Pro Arg |
| Seq. ID No. 185 | Pro Pro Pro Phe Phe Pro Pro Arg Leu |
| Seq. ID No. 186 | Pro Pro Phe Phe Pro Pro Arg Leu Pro |
| Seq. ID No. 187 | Pro Phe Phe Pro Pro Arg Leu Pro Pro |
| Seq. ID No. 188 | Phe Phe Pro Pro Arg Leu Pro Pro Arg |
| Seq. ID No. 189 | Phe Pro Pro Arg Leu Pro Pro Arg Ile |
| Seq. ID No. 190 | Pro Pro Arg Leu Pro Pro Arg Ile Pro |
| Seq. ID No. 191 | Pro Arg Leu Pro Pro Arg Ile Pro Pro |
| Seq. ID No. 192 | Arg Leu Pro Pro Arg Ile Pro Pro Glu |
| Seq. ID No. 193 | Leu Pro Pro Arg Ile Pro Pro Glu Phe |
| Seq. ID No. 194 | Pro Pro Arg Ile Pro Pro Glu Phe Pro |
| Seq. ID No. 195 | Pro Arg Ile Pro Pro Glu Phe Pro Pro |
| Seq. ID No. 196 | Arg Ile Pro Pro Glu Phe Pro Pro Arg |
| Seq. ID No. 197 | Ile Pro Pro Glu Phe Pro Pro Arg Phe |
| Seq. ID No. 198 | Pro Pro Glu Phe Pro Pro Arg Phe Pro |
| Seq. ID No. 199 | Pro Glu Phe Pro Pro Arg Phe Pro Pro |
| Seq. ID No. 200 | Glu Phe Pro Pro Arg Phe Pro Pro Arg |
| Seq. ID No. 201 | Phe Pro Pro Arg Phe Pro Pro Arg Phe |
| Seq. ID No. 202 | Pro Pro Arg Phe Pro Pro Arg Phe Pro |

In a preferred embodiment [AA] consists of a nona-peptide as specified in column I of table 6.

In a further embodiment the oligopeptide consists of at most 15, preferably at most 10 amino acids, of which at least 9 consecutive amino acids are identical to 9 consecutive amino acids of SEQ ID No. 1. Thus in one embodiment of the invention, [AA] comprises 9 consecutive amino acids which are identical to 9 consecutive amino acids of SEQ ID No. 1 and has up to 6 further amino acids (resulting in a total number of 15 amino acids), preferably up to 1 further amino acid (resulting in a total number of 10 amino acids), whereas the further amino acids need not be identical to or even present in SEQ ID No. 1.

In this embodiment [AA] is thus [$X_m$-aa-$Y_o$], wherein aa is a nona-peptide of table 9 and X and Y are further amino acids, m and o being numbers from 0 to 5, with the proviso that m+o is $\leq 5$. In a preferred embodiment, aa is selected from the nona-peptides as specified in column I of table 6. In a further preferred embodiment m+o is =1.

[AA] Moiety: Decapeptide

In one embodiment of the invention, [AA] consists of 10 consecutive amino acids, which are identical to 10 consecutive amino acids of SEQ ID No. 1.

Table 7 list these deca-peptides:

| 30 deca peptides of 10 consecutive amino acids of SEQ ID No. 1 | |
|---|---|
| Seq. ID No. | |
| | Column I |
| Seq. ID No. 203 | Arg Arg Arg Pro Arg Pro Pro Tyr Leu Pro |
| Seq. ID No. 204 | Arg Arg Pro Arg Pro Pro Tyr Leu Pro Arg |
| Seq. ID No. 205 | Arg Pro Arg Pro Pro Tyr Leu Pro Arg Pro |
| Seq. ID No. 206 | Pro Arg Pro Pro Tyr Leu Pro Arg Pro Arg |
| Seq. ID No. 207 | Arg Pro Pro Tyr Leu Pro Arg Pro Arg Pro |
| Seq. ID No. 208 | Pro Pro Tyr Leu Pro Arg Pro Arg Pro Pro |

| 30 deca peptides of 10 consecutive amino acids of SEQ ID No. 1 |
| --- |
| Seq. ID No. |
| Column II |
| Seq. ID No. 209 Pro Tyr Leu Pro Arg Pro Arg Pro Pro Pro |
| Seq. ID No. 210 Tyr Leu Pro Arg Pro Arg Pro Pro Pro Phe |
| Seq. ID No. 211 Leu Pro Arg Pro Arg Pro Pro Pro Phe Phe |
| Seq. ID No. 212 Pro Arg Pro Arg Pro Pro Pro Phe Phe Pro |
| Seq. ID No. 213 Arg Pro Arg Pro Pro Pro Phe Phe Pro Pro |
| Seq. ID No. 214 Pro Arg Pro Pro Pro Phe Phe Pro Pro Arg |
| Seq. ID No. 215 Arg Pro Pro Pro Phe Phe Pro Pro Arg Leu |
| Seq. ID No. 216 Pro Pro Pro Phe Phe Pro Pro Arg Leu Pro |
| Seq. ID No. 217 Pro Pro Phe Phe Pro Pro Arg Leu Pro Pro |
| Seq. ID No. 218 Pro Phe Phe Pro Pro Arg Leu Pro Pro Arg |
| Seq. ID No. 219 Phe Phe Pro Pro Arg Leu Pro Pro Arg Ile |
| Seq. ID No. 220 Phe Pro Pro Arg Leu Pro Pro Arg Ile Pro |
| Seq. ID No. 221 Pro Pro Arg Leu Pro Pro Arg Ile Pro Pro |
| Seq. ID No. 222 Pro Arg Leu Pro Pro Arg Ile Pro Pro Glu |
| Seq. ID No. 223 Arg Leu Pro Pro Arg Ile Pro Pro Glu Phe |
| Seq. ID No. 224 Leu Pro Pro Arg Ile Pro Pro Glu Phe Pro |
| Seq. ID No. 225 Pro Pro Arg Ile Pro Pro Glu Phe Pro Pro |
| Seq. ID No. 226 Pro Arg Ile Pro Pro Glu Phe Pro Pro Arg |
| Seq. ID No. 227 Arg Ile Pro Pro Glu Phe Pro Pro Arg Phe |
| Seq. ID No. 228 Ile Pro Pro Glu Phe Pro Pro Arg Phe Pro |
| Seq. ID No. 229 Pro Pro Glu Phe Pro Pro Arg Phe Pro Pro |
| Seq. ID No. 230 Pro Glu Phe Pro Pro Arg Phe Pro Pro Arg |
| Seq. ID No. 231 Glu Phe Pro Pro Arg Phe Pro Pro Arg Phe |
| Seq. ID No. 232 Phe Pro Pro Arg Phe Pro Pro Arg Phe Pro |

In a preferred embodiment [AA] consists of a deca-peptide as specified in column I of table 7.

In a further embodiment the oligopeptide consists of at most 15, preferably at most 12 amino acids, of which at least 10 consecutive amino acids are identical to 10 consecutive amino acids of SEQ ID No. 1. Thus in one embodiment of the invention, [AA] comprises 10 consecutive amino acids which are identical to 10 consecutive amino acids of SEQ ID No. 1 and has up to 4 further amino acids (resulting in a total number of 15 amino acids), preferably up to 2 further amino acids (resulting in a total number of 12 amino acids), whereas the further amino acids need not be identical to or even present in SEQ ID No. 1.

In this embodiment [AA] is thus [$X_m$-aa-$Y_o$], wherein aa is a deca-peptide of table 7 and X and Y are further amino acids, m and o being numbers from 0 to 5, with the proviso that m+o is $\leq 5$. In a preferred embodiment, aa is selected from the deca-peptides as specified in column 1 of table 7. In a further preferred embodiment m+o is $\leq 2$.

[AA] Moiety: Undecapeptide

In one embodiment of the invention, [AA] consists of 11 consecutive amino acids, which are identical to 11 consecutive amino acids of SEQ ID No. 1.

Table 8 list these undeca-peptides:

| 29 undeca-peptides of 11 consecutive amino acids of SEQ ID No. 1 |
| --- |
| Seq. ID No. |
| Column I |
| Seq. ID No. 233 Arg Arg Arg Pro Arg Pro Pro Tyr Leu Pro Arg |
| Seq. ID No. 234 Arg Arg Pro Arg Pro Pro Tyr Leu Pro Arg Pro |
| Seq. ID No. 235 Arg Pro Arg Pro Pro Tyr Leu Pro Arg Pro Arg |
| Seq. ID No. 236 Pro Arg Pro Pro Tyr Leu Pro Arg Pro Arg Pro |
| Seq. ID No. 237 Arg Pro Pro Tyr Leu Pro Arg Pro Arg Pro Pro |

29 undeca-peptides of 11 consecutive amino acids of SEQ ID No. 1

| Seq. ID No. | Column II |
|---|---|
| Seq. ID No. 238 | Pro Pro Tyr Leu Pro Arg Pro Arg Pro Pro Pro |
| Seq. ID No. 239 | Pro Tyr Leu Pro Arg Pro Arg Pro Pro Pro Phe |
| Seq. ID No. 240 | Tyr Leu Pro Arg Pro Arg Pro Pro Pro Phe Phe |
| Seq. ID No. 241 | Leu Pro Arg Pro Arg Pro Pro Pro Phe Phe Pro |
| Seq. ID No. 242 | Pro Arg Pro Arg Pro Pro Pro Phe Phe Pro Pro |
| Seq. ID No. 243 | Arg Pro Arg Pro Pro Pro Phe Phe Pro Pro Arg |
| Seq. ID No. 244 | Pro Arg Pro Pro Pro Phe Phe Pro Pro Arg Leu |
| Seq. ID No. 245 | Arg Pro Pro Pro Phe Phe Pro Pro Arg Leu Pro |
| Seq. ID No. 246 | Pro Pro Pro Phe Phe Pro Pro Arg Leu Pro Pro |
| Seq. ID No. 247 | Pro Pro Phe Phe Pro Pro Arg Leu Pro Pro Arg |
| Seq. ID No. 248 | Pro Phe Phe Pro Pro Arg Leu Pro Pro Arg Ile |
| Seq. ID No. 249 | Phe Phe Pro Pro Arg Leu Pro Pro Arg Ile Pro |
| Seq. ID No. 250 | Phe Pro Pro Arg Leu Pro Pro Arg Ile Pro Pro |
| Seq. ID No. 251 | Pro Pro Arg Leu Pro Pro Arg Ile Pro Pro Glu |
| Seq. ID No. 252 | Pro Arg Leu Pro Pro Arg Ile Pro Pro Glu Phe |
| Seq. ID No. 253 | Arg Leu Pro Pro Arg Ile Pro Pro Glu Phe Pro |
| Seq. ID No. 254 | Leu Pro Pro Arg Ile Pro Pro Glu Phe Pro Pro |
| Seq. ID No. 255 | Pro Pro Arg Ile Pro Pro Glu Phe Pro Pro Arg |
| Seq. ID No. 256 | Pro Arg Ile Pro Pro Glu Phe Pro Pro Arg Phe |
| Seq. ID No. 257 | Arg Ile Pro Pro Glu Phe Pro Pro Arg Phe Pro |
| Seq. ID No. 258 | Ile Pro Pro Glu Phe Pro Pro Arg Phe Pro Pro |
| Seq. ID No. 259 | Pro Pro Glu Phe Pro Pro Arg Phe Pro Pro Arg |
| Seq. ID No. 260 | Pro Glu Phe Pro Pro Arg Phe Pro Pro Arg Phe |
| Seq. ID No. 261 | Glu Phe Pro Pro Arg Phe Pro Pro Arg Phe Pro |

In a preferred embodiment [AA] consists of an undeca-peptide as specified in column I of table 8.

In a further embodiment the oligopeptide consists of at most 15, preferably at most 12 amino acids, of which at least 11 consecutive amino acids are identical to 11 consecutive amino acids of SEQ ID No. 1. Thus in one embodiment of the invention, [AA] comprises 11 consecutive amino acids which are identical to 11 consecutive amino acids of SEQ ID No. 1 and has up to 4 further amino acids (resulting in a total number of 15 amino acids), preferably up to 1 further amino acids (resulting in a total number of 12 amino acids), whereas the further amino acids need not be identical to or even present in SEQ ID No. 1.

In this embodiment [AA] is thus $[X_m\text{-aa-}Y_o]$, wherein aa is an undeca-peptide of table 8 and X and Y are further amino acids, m and o being numbers from 0 to 4, with the proviso that m+o is $\leq 4$. In a preferred embodiment, aa is selected from the undeca-peptides as specified in column I of table 8. In a further preferred embodiment m+o is =1.

[AA] Moiety: Dodecapeptide

In one embodiment of the invention, [AA] consists of 12 consecutive amino acids, which are identical to 12 consecutive amino acids of SEQ ID No. 1.

Table 9 list these dodeca-peptides:

```
          28 dodeca-peptides of 12 consecutive amino acids
                         of SEQ ID No. 1
```

Seq. ID No.

Column I

Seq. ID No. 262  Arg Arg Arg Pro Arg Pro Pro Tyr Leu Pro Arg Pro

Seq. ID No. 263  Arg Arg Pro Arg Pro Pro Tyr Leu Pro Arg Pro Arg

Seq. ID No. 264  Arg Pro Arg Pro Pro Tyr Leu Pro Arg Pro Arg Pro

Seq. ID No. 265  Pro Arg Pro Pro Tyr Leu Pro Arg Pro Arg Pro Pro

Column II

Seq. ID No. 266  Arg Pro Pro Tyr Leu Pro Arg Pro Arg Pro Pro Pro

Seq. ID No. 267  Pro Pro Tyr Leu Pro Arg Pro Arg Pro Pro Pro Phe

Seq. ID No. 268  Pro Tyr Leu Pro Arg Pro Arg Pro Pro Pro Phe Phe

Seq. ID No. 269  Tyr Leu Pro Arg Pro Arg Pro Pro Pro Phe Phe Pro

Seq. ID No. 270  Leu Pro Arg Pro Arg Pro Pro Pro Phe Phe Pro Pro

Seq. ID No. 271  Pro Arg Pro Arg Pro Pro Pro Phe Phe Pro Pro Arg

Seq. ID No. 272  Arg Pro Arg Pro Pro Pro Phe Phe Pro Pro Arg Leu

Seq. ID No. 273  Pro Arg Pro Pro Pro Phe Phe Pro Pro Arg Leu Pro

Seq. ID No. 274  Arg Pro Pro Pro Phe Phe Pro Pro Arg Leu Pro Pro

Seq. ID No. 275  Pro Pro Pro Phe Phe Pro Pro Arg Leu Pro Pro Arg

Seq. ID No. 276  Pro Pro Phe Phe Pro Pro Arg Leu Pro Pro Arg Ile

Seq. ID No. 277  Pro Phe Phe Pro Pro Arg Leu Pro Pro Arg Ile Pro

Seq. ID No. 278  Phe Phe Pro Pro Arg Leu Pro Pro Arg Ile Pro Pro

Seq. ID No. 279  Phe Pro Pro Arg Leu Pro Pro Arg Ile Pro Pro Glu

Seq. ID No. 280  Pro Pro Arg Leu Pro Pro Arg Ile Pro Pro Glu Phe

Seq. ID No. 281  Pro Arg Leu Pro Pro Arg Ile Pro Pro Glu Phe Pro

Seq. ID No. 282  Arg Leu Pro Pro Arg Ile Pro Pro Glu Phe Pro Pro

Seq. ID No. 283  Leu Pro Pro Arg Ile Pro Pro Glu Phe Pro Pro Arg

Seq. ID No. 284  Pro Pro Arg Ile Pro Pro Glu Phe Pro Pro Arg Phe

Seq. ID No. 285  Pro Arg Ile Pro Pro Glu Phe Pro Pro Arg Phe Pro

Seq. ID No. 286  Arg Ile Pro Pro Glu Phe Pro Pro Arg Phe Pro Pro

Seq. ID No. 287  Ile Pro Pro Glu Phe Pro Pro Arg Phe Pro Pro Arg

Seq. ID No. 288  Pro Pro Glu Phe Pro Pro Arg Phe Pro Pro Arg Phe

Seq. ID No. 289  Pro Glu Phe Pro Pro Arg Phe Pro Pro Arg Phe Pro

In a preferred embodiment [AA] consists of a dodeca-peptide as specified in column I of table 9.

In a further embodiment the oligopeptide consists of at most 15, of which at least 12 consecutive amino acids are identical to 12 consecutive amino acids of SEQ ID No. 1. Thus in one embodiment of the invention, [AA] comprises 12 consecutive amino acids which are identical to 12 consecutive amino acids of SEQ ID No. 1 and has up to 3 further amino acids (resulting in a total number of 15 amino acids), preferably up to 2 further amino acids (resulting in a total number of 14 amino acids), more preferably up to 1 further amino acid (resulting in a total number of 13 amino acids), whereas the further amino acids need not be identical to or even present in SEQ ID No. 1.

In this embodiment [AA] is thus $[X_m\text{-aa-}Y_o]$, wherein aa is a dodeca-peptide of table 9 and X and Y are further amino acids, m and o being numbers from 0 to 3, with the proviso that m+o is $\leq 3$. In a preferred embodiment, aa is selected from the dodeca-peptides as specified in column I of table 9. In a further preferred embodiment m+o is $\leq 2$, preferably =1.

[AA] Moiety: Tridecapeptide

In one embodiment of the invention, [AA] consists of 13 consecutive amino acids, which are identical to 13 consecutive amino acids of SEQ ID No. 1.

Table 10 list these trideca-peptides:

amino acids of SEQ ID No. 1. Thus in one embodiment of the invention, [AA] comprises 13 consecutive amino acids which are identical to 13 consecutive amino acids of SEQ ID No. 1 and has up to 2 further amino acids (resulting in a total number of 15 amino acids), preferably up to 1 further amino 27 trideca peptides of 13 consecutive amino acids of SEQ ID No. 1

Seq. ID No.

Column I

Seq. ID No. 290  Arg Arg Arg Pro Arg Pro Pro Tyr Leu Pro Arg Pro Arg

Seq. ID No. 291  Arg Arg Pro Arg Pro Pro Tyr Leu Pro Arg Pro Arg Pro

Seq. ID No. 292  Arg Pro Arg Pro Pro Tyr Leu Pro Arg Pro Arg Pro Pro

Column II

Seq. ID No. 293  Pro Arg Pro Pro Tyr Leu Pro Arg Pro Arg Pro Pro Pro

Seq. ID No. 294  Arg Pro Pro Tyr Leu Pro Arg Pro Arg Pro Pro Pro Phe

Seq. ID No. 285  Pro Pro Tyr Leu Pro Arg Pro Arg Pro Pro Pro Phe Phe

Seq. ID No. 296  Pro Tyr Leu Pro Arg Pro Arg Pro Pro Pro Phe Phe Pro

Seq. ID No. 297  Tyr Leu Pro Arg Pro Arg Pro Pro Pro Phe Phe Pro Pro

Seq. ID No. 298  Leu Pro Arg Pro Arg Pro Pro Pro Phe Phe Pro Pro Arg

Seq. ID No. 299  Pro Arg Pro Arg Pro Pro Pro Phe Phe Pro Pro Arg Leu

Seq. ID No. 300  Arg Pro Arg Pro Pro Pro Phe Phe Pro Pro Arg Leu Pro

Seq. ID No. 301  Pro Arg Pro Pro Pro Phe Phe Pro Pro Arg Leu Pro Pro

Seq. ID No. 302  Arg Pro Pro Pro Phe Phe Pro Pro Arg Leu Pro Pro Arg

Seq. ID No. 303  Pro Pro Pro Phe Phe Pro Pro Arg Leu Pro Pro Arg Ile

Seq. ID No. 304  Pro Pro Phe Phe Pro Pro Arg Leu Pro Pro Arg Ile Pro

Seq. ID No. 305  Pro Phe Phe Pro Pro Arg Leu Pro Pro Arg Ile Pro Pro

Seq. ID No. 306  Phe Phe Pro Pro Arg Leu Pro Pro Arg Ile Pro Pro Glu

Seq. ID No. 307  Phe Pro Pro Arg Leu Pro Pro Arg Ile Pro Pro Glu Phe

Seq. ID No. 308  Pro Pro Arg Leu Pro Pro Arg Ile Pro Pro Glu Phe Pro

Seq. ID No. 309  Pro Arg Leu Pro Pro Arg Ile Pro Pro Glu Phe Pro Pro

Seq. ID No. 310  Arg Leu Pro Pro Arg Ile Pro Pro Glu Phe Pro Pro Arg

Seq. ID No. 311  Leu Pro Pro Arg Ile Pro Pro Glu Phe Pro Pro Arg Phe

Seq. ID No. 312  Pro Pro Arg Ile Pro Pro Glu Phe Pro Pro Arg Phe Pro

Seq. ID No. 313  Pro Arg Ile Pro Pro Glu Phe Pro Pro Arg Phe Pro Pro

Seq. ID No. 314  Arg Ile Pro Pro Glu Phe Pro Pro Arg Phe Pro Pro Arg

Seq. ID No. 315  Ile Pro Pro Glu Phe Pro Pro Arg Phe Pro Pro Arg Phe

Seq. ID No. 316  Pro Pro Glu Phe Pro Pro Arg Phe Pro Pro Arg Phe Pro

In a preferred embodiment [AA] consists of a tridecapeptide as specified in column I of table 10.

In a further embodiment the oligopeptide consists of at most 15, preferably at most 14 amino acids, of which at least 13 consecutive amino acids are identical to 13 consecutive amino acids of SEQ ID No. 1 (resulting in a total number of 14 amino acids), whereas the further amino acids need not be identical to or even present in SEQ ID No. 1.

In this embodiment [AA] is thus $[X_m\text{-aa-}Y_o]$, wherein aa is a trideca-peptide of table 10 and X and Y are further amino acids, m and o being numbers from 0 to 2, with the proviso that m+o is ≦2. In a preferred embodiment, aa is selected from the trdeca-peptides as specified in column I of table 10. In a further preferred embodiment m+o is =1.

[AA] Moiety: Tetradecapeptide

In one embodiment of the invention, [AA] consists of 14 consecutive amino acids, which are identical to 14 consecutive amino acids of SEQ ID No. 1.

Table 11 list these tetradeca-peptides:

consecutive amino acids which are identical to 14 consecutive amino acids of SEQ ID No. 1 and has up to 1 further amino acids (resulting in a total number of 15 amino acids), whereas the further amino acids need not be identical to or even present in SEQ ID No. 1.

In this embodiment [AA] is thus $[X_m\text{-aa-}Y_o]$, wherein aa is a tetradeca-peptide of table 1 and X and Y are further amino acids, m and o being numbers from 0 to 1, with the proviso

| 26 tetradeca peptides of 14 consecutive amino acids of SEQ ID No. 1 |
|---|
| Seq. ID No. |
| Column I |
| Seq. ID No. 317  Arg Arg Arg Pro Arg Pro Pro Tyr Leu Pro Arg Pro Arg Pro |
| Seq. ID No. 318  Arg Arg Pro Arg Pro Pro Tyr Leu Pro Arg Pro Arg Pro Pro |
| Column II |
| Seq. ID No. 319  Arg Pro Arg Pro Pro Tyr Leu Pro Arg Pro Arg Pro Pro Pro |
| Seq. ID No. 320  Pro Arg Pro Pro Tyr Leu Pro Arg Pro Arg Pro Pro Pro Phe |
| Seq. ID No. 321  Arg Pro Pro Tyr Leu Pro Arg Pro Arg Pro Pro Pro Phe Phe |
| Seq. ID No. 322  Pro Pro Tyr Leu Pro Arg Pro Arg Pro Pro Pro Phe Phe Pro |
| Seq. ID No. 323  Pro Tyr Leu Pro Arg Pro Arg Pro Pro Pro Phe Phe Pro Pro |
| Seq. ID No. 324  Tyr Leu Pro Arg Pro Arg Pro Pro Pro Phe Phe Pro Pro Arg |
| Seq. ID No. 325  Leu Pro Arg Pro Arg Pro Pro Pro Phe Phe Pro Pro Arg Leu |
| Seq. ID No. 326  Pro Arg Pro Arg Pro Pro Pro Phe Phe Pro Pro Arg Leu Pro |
| Seq. ID No. 327  Pro Arg Pro Pro Pro Phe Phe Pro Pro Arg Leu Pro Pro Arg |
| Seq. ID No. 328  Arg Pro Pro Pro Phe Phe Pro Pro Arg Leu Pro Pro Arg Ile |
| Seq. ID No. 329  Pro Pro Pro Phe Phe Pro Pro Arg Leu Pro Pro Arg Ile Pro |
| Seq. ID No. 330  Pro Pro Phe Phe Pro Pro Arg Leu Pro Pro Arg Ile Pro Pro |
| Seq. ID No. 331  Pro Phe Phe Pro Pro Arg Leu Pro Pro Arg Ile Pro Pro Glu |
| Seq. ID No. 332  Phe Phe Pro Pro Arg Leu Pro Pro Arg Ile Pro Pro Glu Phe |
| Seq. ID No. 333  Phe Pro Pro Arg Leu Pro Pro Arg Ile Pro Pro Glu Phe Pro |
| Seq. ID No. 334  Pro Arg Leu Pro Pro Arg Ile Pro Pro Glu Phe Pro Pro Arg |
| Seq. ID No. 335  Arg Leu Pro Pro Arg Ile Pro Pro Glu Phe Pro Pro Arg Phe |
| Seq. ID No. 336  Leu Pro Pro Arg Ile Pro Pro Glu Phe Pro Pro Arg Phe Pro |
| Seq. ID No. 337  Pro Pro Arg Ile Pro Pro Glu Phe Pro Pro Arg Phe Pro Pro |
| Seq. ID No. 338  Pro Arg Ile Pro Pro Glu Phe Pro Pro Arg Phe Pro Pro Arg |
| Seq. ID No. 339  Arg Ile Pro Pro Glu Phe Pro Pro Arg Phe Pro Pro Arg Phe |
| Seq. ID No. 340  Ile Pro Pro Glu Phe Pro Pro Arg Phe Pro Pro Arg Phe Pro |

In a preferred embodiment [AA] consists of a tetradeca-peptide as specified in column I of table 11.

In a further embodiment the oligopeptide consists of at most 15, of which at least 14 consecutive amino acids are identical to 14 consecutive amino acids of SEQ ID No. 1. Thus in one embodiment of the invention, [AA] comprises 14 that m+o is =1. In a preferred embodiment, aa is selected from the tetradeca-peptides as specified in column I of table 11.

[AA] Moiety: Pentadecapeptide

In one embodiment of the invention, [AA] consists of 15 consecutive amino acids, which are identical to 15 consecutive amino acids of SEQ ID No. 1.

Table 12 lists these pentadeca peptides:

25 pentadeca-peptides of 15 consecutive amino acids of SEQ ID No. 1

Seq. ID No.

Column I

Seq. ID No. 341  Arg Arg Arg Pro Arg Pro Pro Tyr Leu Pro Arg Pro Arg Pro Pro

Column II

Seq. ID No. 342  Arg Arg Pro Arg Pro Pro Tyr Leu Pro Arg Pro Arg Pro Pro Pro

Seq. ID No. 343  Arg Pro Arg Pro Pro Tyr Leu Pro Arg Pro Arg Pro Pro Pro Phe

Seq. ID No. 344  Pro Arg Pro Pro Tyr Leu Pro Arg Pro Arg Pro Pro Pro Phe Phe

Seq. ID No. 345  Arg Pro Pro Tyr Leu Pro Arg Pro Arg Pro Pro Pro Phe Phe Pro

Seq. ID No. 346  Pro Pro Tyr Leu Pro Arg Pro Arg Pro Pro Pro Phe Phe Pro Pro

Seq. ID No. 347  Pro Tyr Leu Pro Arg Pro Arg Pro Pro Pro Phe Phe Pro Pro Arg

Seq. ID No. 348  Tyr Leu Pro Arg Pro Arg Pro Pro Pro Phe Phe Pro Pro Arg Leu

Seq. ID No. 349  Leu Pro Arg Pro Arg Pro Pro Pro Phe Phe Pro Pro Arg Leu Pro

Seq. ID No. 350  Pro Arg Pro Arg Pro Pro Pro Phe Phe Pro Pro Arg Leu Pro Pro

Seq. ID No. 351  Arg Pro Arg Pro Pro Pro Phe Phe Pro Pro Arg Leu Pro Pro Arg

Seq. ID No. 352  Pro Arg Pro Pro Pro Phe Phe Pro Pro Arg Leu Pro Pro Arg Ile

Seq. ID No. 353  Arg Pro Pro Pro Phe Phe Pro Pro Arg Leu Pro Pro Arg Ile Pro

Seq. ID No. 354  Pro Pro Pro Phe Phe Pro Pro Arg Leu Pro Pro Arg Ile Pro Pro

Seq. ID No. 355  Pro Pro Phe Phe Pro Pro Arg Leu Pro Pro Arg Ile Pro Pro Glu

Seq. ID No. 356  Pro Phe Phe Pro Pro Arg Leu Pro Pro Arg Ile Pro Pro Glu Phe

Seq. ID No. 357  Phe Phe Pro Pro Arg Leu Pro Pro Arg Ile Pro Pro Glu Phe Pro

Seq. ID No. 358  Phe Pro Pro Arg Leu Pro Pro Arg Ile Pro Pro Glu Phe Pro Pro

Seq. ID No. 359  Pro Pro Arg Leu Pro Pro Arg Ile Pro Pro Glu Phe Pro Pro Arg

Seq. ID No. 360  Pro Arg Leu Pro Pro Arg Ile Pro Pro Glu Phe Pro Pro Arg Phe

Seq. ID No. 361  Arg Leu Pro Pro Arg Ile Pro Pro Glu Phe Pro Pro Arg Phe Pro

Seq. ID No. 362  Leu Pro Pro Arg Ile Pro Pro Glu Phe Pro Pro Arg Phe Pro Pro

Seq. ID No. 363  Pro Pro Arg Ile Pro Pro Glu Phe Pro Pro Arg Phe Pro Pro Arg

Seq. ID No. 364  Pro Arg Ile Pro Pro Glu Phe Pro Pro Arg Phe Pro Pro Arg Phe

Seq. ID No. 365  Arg Ile Pro Pro Glu Phe Pro Pro Arg Phe Pro Pro Arg Phe Pro

In a preferred embodiment [AA] consists of the pentadecapeptide as specified in column I of table 12.

[AA] Moiety: Hexapeptides

In an embodiment [AA] comprises at least 6 amino acids, of which 4, preferably 5, more preferably 6 are identical compared to 6 consecutive amino acids of SEQ ID No. 1. Any possible 6 consecutive amino acids of SEQ ID No. 1 are listed in Table 3.

Thus in this embodiment of the invention, [AA] comprises at least 6 amino acids, of which at least 66.6%, preferably at least 83.3%, preferably 100% are identical to 6 consecutive amino acids of SEQ ID No. 1.

In a preferred embodiment [AA] comprises at least 6 amino acids, of which 4 amino acids, preferably 5 amino acids are identical compared to 6 consecutive amino acids of SEQ ID No. 1 and the position of the 4, respective 5 identical amino acids is also identical when compared to the respective positions of the 6 amino acids of SEQ ID No. 1.

Thus in this embodiment of the invention [AA] comprises at least 6 amino acids, of which at least 66.6%, preferably at least 83.3% are identical to 6 consecutive amino acids of SEQ ID No. 1 and the position of the 4, respective 5 identical amino acids is also identical when compared to the respective positions of the 6 amino acids of SEQ ID No. 1.

In following chart illustrates this embodiment of the invention. X and Y are further amino acids.

|  | Position No. | | | | | |
| --- | --- | --- | --- | --- | --- | --- |
|  | 1 | 2 | 3 | 4 | 5 | 6 |
| SEQ ID No. 1 | Arg | Arg | Arg | Pro | Arg | Pro |
| [AA] | Arg | X | Arg | Y | Arg | Pro |
| [AA] | Arg | Arg | Arg | Y | Arg | Pro |

In a preferred embodiment [AA] comprises at least 6 amino acids, of which 4, preferably 5 are identical to 6 consecutive amino acids of column I of table 3.

In a further embodiment [AA] consists of 6 amino acids, of which 4, preferably 5, more preferably 6 are identical compared to 6 consecutive amino acids of SEQ ID No. 1. Any possible 6 consecutive amino acids of SEQ ID No. 1 are listed in Table 3.

Thus in this embodiment of the invention, [AA] consists of 6 amino acids, of which at least 66.6%, preferably at least 83.3%, more preferably 100% are identical to 6 consecutive amino acids of SEQ ID No. 1.

In a preferred embodiment [AA] consists of 6 amino acids, of which 4 amino acids, preferably 5 amino acids are identical compared to 6 consecutive amino acids of SEQ ID No. 1 and the position of the 4, respective 5 identical amino acids is also identical when compared to the respective position of the 6 amino acids of SEQ ID No. 1.

In a preferred embodiment [AA] consists of least 6 amino acids, of which 4, preferably 5 are identical to 6 consecutive amino acids of column I of table 3.

In a further embodiment [AA] consists of at most 15, preferably at most 10, more preferably at most 8 amino acids, of which 4 amino acids, preferably 5 amino acids, more preferably 6, are identical to 6 consecutive amino acids of SEQ ID No. 1.

In a further embodiment [AA] consists of at most 15, preferably at most 10, more preferably at most 8 amino acids, of which 4 amino acids, preferably 5 amino acids, are identical to 6 consecutive amino acids of SEQ ID No. 1 and the position of the 4, respective 5 amino acids is identical to the positions of respective amino acids of the 6 amino acids of SEQ ID no. 1. In this embodiment of the invention, also the position of the 4, respective 5 amino acids is identical when compared to the respective positions of 6 consecutive amino acids of SEQ ID No. 1.

[AA] Moiety: Heptapeptides

In a further embodiment [AA] comprises at least 7 amino acids, of which 5, preferably 6, more preferably 7 are identical compared to 7 consecutive amino acids of SEQ ID No. 1. Any possible 7 consecutive amino acids of SEQ ID No. 1 are listed in Table 4.

Thus in this embodiment of the invention, [AA] comprises at least 7 amino acids, of which at least 71.4%, preferably at least 85.7%, preferably 100% are identical to 7 consecutive amino acids of SEQ ID No. 1.

In a preferred embodiment [AA] comprises at least 7 amino acids, of which 5 amino acids, preferably 6 amino acids are identical compared to 7 consecutive amino acids of SEQ ID No. 1 and the position of the 5, respective 6 identical amino acids is also identical when compared to the respective positions of the 7 amino acids of SEQ ID No. 1.

Thus in this embodiment of the invention [AA] comprises at least 7 amino acids, of which at least 71.4%, preferably at least 85.7% are identical to 7 consecutive amino acids of SEQ ID No. 1 and the position of the 5, respective 6 identical amino acids is also identical when compared to the respective positions of the 7 amino acids of SEQ ID No. 1.

In a preferred embodiment [AA] comprises at least 7 amino acids, of which 5, preferably 6 are identical to 7 consecutive amino acids of column I of table 4.

In a further embodiment [AA] consists of 7 amino acids, of which 5, preferably 6, preferably 7 are identical compared to 7 consecutive amino acids of SEQ ID No. 1. Any possible 7 consecutive amino acids of SEQ ID No. 1 are listed in table 4.

Thus in this embodiment of the invention, [AA] consists of 7 amino acids, of which at least 71.4%, preferably at least 85.7%, preferably 100% are identical to 7 consecutive amino acids of SEQ ID No. 1.

In a preferred embodiment [AA] consists of 7 amino acids, of which 5 amino acids, preferably 6 amino acids are identical compared to 7 consecutive amino acids of SEQ ID No. 1 and the position of the 5, respective 6 identical amino acids is also identical when compared to the respective position of the 7 amino acids of SEQ ID No. 1.

In a preferred embodiment [AA] consists of least 7 amino acids, of which 5, preferably 6 are identical to 7 consecutive amino acids of column I of table 4.

In a further embodiment [AA] consists of at most 15, preferably at most 10, more preferably at most 8 amino acids, of which 5, preferably 6, preferably 7 amino acids, are identical to 7 consecutive amino acids of SEQ ID No. 1.

In a further embodiment [AA] consists of at most 15, preferably at most 10, more preferably at most 8 amino acids, of which 5 amino acids, preferably 6 amino acids, are identical to 7 consecutive amino acids of SEQ ID No. 1 and the position of the 5, respective 6 amino acids is identical to the positions of respective amino acids of the 7 amino acids of SEQ ID no. 1. In this embodiment of the invention, also the position of the 5, respective 6 amino acids is identical when compared to the respective positions of 7 consecutive amino acids of SEQ ID No. 1.

[AA] Moiety: Octapeptides

In a further embodiment [AA] comprises at least 8 amino acids, of which 6, preferably 7, preferably 8 are identical compared to 8 consecutive amino acids of SEQ ID No. 1. Any possible 8 consecutive amino acids of SEQ ID No. 1 are listed in Table 5.

Thus in this embodiment of the invention, [AA] comprises at least 8 amino acids, of which at least 75%, preferably at least 87.5%, preferably 100% are identical to 8 consecutive amino acids of SEQ ID No. 1.

In a preferred embodiment [AA] comprises at least 8 amino acids, of which 6 amino acids, preferably 7 amino acids are identical compared to 8 consecutive amino acids of SEQ ID No. 1 and the position of the 6, respective 7 identical amino acids is also identical when compared to the respective positions of the 8 amino acids of SEQ ID No. 1.

Thus in this embodiment of the invention [AA] comprises at least 8 amino acids, of which at least 75° A), preferably at least 87.5% are identical to 8 consecutive amino acids of SEQ ID NO. 1 and the position of the 6, respective 7 identical amino acids is also identical when compared to the respective positions of the 8 amino acids of SEQ ID No. 1.

In a preferred embodiment [AA] comprises at least 8 amino acids, of which 6, preferably 7 are identical to 8 consecutive amino acids of column I of table 5.

In a further embodiment [AA] consists of 8 amino acids, of which 6, preferably 7, preferably 8 are identical compared to 8 consecutive amino acids of SEQ ID No. 1.

Any possible 8 consecutive amino acids of SEQ ID No. 1 are listed in table 5.

Thus in this embodiment of the invention, [AA] consists of 8 amino acids, of which at least 75%, preferably at least 87.5%, preferably 100% are identical to 8 consecutive amino acids of SEQ ID No. 1.

In a preferred embodiment [AA] consists of 8 amino acids, of which 6 amino acids, preferably 7 amino acids are identical compared to 8 consecutive amino acids of SEQ ID No. 1 and the position of the 6, respective 7 identical amino acids is also identical when compared to the respective position of the 8 amino acids of SEQ ID No. 1.

In a preferred embodiment [AA] consists of least 8 amino acids, of which 6, preferably 7 are identical to 8 consecutive amino acids of column I of table 5.

In a further embodiment [AA] consists of at most 15, preferably at most 10, more preferably at most 9 amino acids, of which 6, preferably 7, preferably 8 amino acids, are identical to 8 consecutive amino acids of SEQ ID No. 1.

In a further embodiment [AA] consists of at most 15, preferably at most 10, more preferably at most 9 amino acids, of which 6 amino acids, preferably 7 amino acids, are identical to 8 consecutive amino acids of SEQ ID No. 1 and the position of the 6, respective 7 amino acids is identical to the positions of respective amino acids of the 8 amino acids of SEQ ID no. 1. In this embodiment of the invention, also the position of the 6, respective 7 amino acids is identical when compared to the respective positions of 8 consecutive amino acids of SEQ ID No. 1.

[AA] Moiety: Nonapeptides

In a further embodiment [AA] comprises at least 9 amino acids, of which 6, preferably 7, more preferably 8, more preferably 9 amino acids are identical compared to 9 consecutive amino acids of SEQ ID No. 1. Any possible 9 consecutive amino acids of SEQ ID No. 1 are listed in Table 6.

Thus in this embodiment of the invention, [AA] comprises at least 9 amino acids, of which at least 66.6%, preferably at least 77.7%, more preferably at least 88.8%, more preferably 100% are identical to 9 consecutive amino acids of SEQ ID No. 1.

In a preferred embodiment [AA] comprises at least 9 amino acids, of which 6 amino acids, preferably 7 amino acids, more preferably 8 amino acids are identical compared to 9 consecutive amino acids of SEQ ID No. 1 and the position of the 6, respective 7 or 8 identical amino acids is also identical when compared to the respective positions of the 9 amino acids of SEQ ID No. 1.

Thus in this embodiment of the invention [AA] comprises at least 9 amino acids, of which at least 66.6%, preferably at least 77.7%, more preferably at least 88.8% are identical to 9 consecutive amino acids of SEQ ID No. 1 and the position of the 6, respective 7 or 8 identical amino acids is also identical when compared to the respective positions of the 9 amino acids of SEQ ID No. 1.

In a preferred embodiment [AA] comprises at least 9 amino acids, of which 6, preferably 7, more preferably 8 are identical to 9 consecutive amino acids of column I of table 6.

In a further embodiment [AA] consists of 9 amino acids, of which 6, preferably 7, more preferably 8, more preferably 9, are identical compared to 9 consecutive amino acids of SEQ ID No. 1. Any possible 9 consecutive amino acids of SEQ ID No. 1 are listed in table 6.

Thus in this embodiment of the invention, [AA] consists of 9 amino acids, of which at least 66.6%, preferably at least 77.7%, more preferably at least 88.8%, more preferably 100% are identical to 9 consecutive amino acids of SEQ ID No. 1.

In a preferred embodiment [AA] consists of 9 amino acids, of which 6 amino acids, preferably 7 amino acids, more preferably 8 amino acids are identical compared to 9 consecutive amino acids of SEQ ID No. 1 and the position of the 6, respective 7 or 8 identical amino acids is also identical when compared to the respective position of the 9 amino acids of SEQ ID No. 1.

In a preferred embodiment [AA] consists of least 9 amino acids, of which 6, preferably 7, more preferably 8 are identical to 9 consecutive amino acids of column I of table 6.

In a further embodiment [AA] consists of at most 15, preferably at most 12, more preferably at most 10 amino acids, of which 6, preferably 7, more preferably 8, more preferably 9 amino acids are identical to 9 consecutive amino acids of SEQ ID No. 1.

In a further embodiment [AA] consists of at most 15, preferably at most 12, more preferably at most 10 amino acids, of which 6 amino acids, preferably 7, more preferably 8 amino acids, are identical to 9 consecutive amino acids of SEQ ID No. 1 and the position of the 6, respective 7 or 8 amino acids is identical to the positions of respective amino acids of the 9 amino acids of SEQ ID No. 1. In this embodiment of the invention, also the position of the 6, respective 7 or 8 amino acids is identical when compared to the respective positions of 9 consecutive amino acids of SEQ ID No. 1.

[AA] Moiety: Decapeptides

In a further embodiment [AA] comprises at least 10 amino acids, of which 7, preferably 8, more preferably 9, more preferably 10 amino acids are identical compared to 10 consecutive amino acids of SEQ ID No. 1. Any possible 10 consecutive amino acids of SEQ ID No. 1 are listed in Table 7.

Thus in this embodiment of the invention, [AA] comprises at least 10 amino acids, of which at least 70%, preferably at least 80%, more preferably at least 90%, more preferably 100% are identical to 10 consecutive amino acids of SEQ ID No. 1.

In a preferred embodiment [AA] comprises at least 10 amino acids, of which 7 amino acids, preferably 8 amino acids, more preferably 9 amino acids are identical compared to 10 consecutive amino acids of SEQ ID No. 1 and the position of the 7, respective 8 or 9 identical amino acids is also identical when compared to the respective positions of the 10 amino acids of SEQ ID No. 1.

Thus in this embodiment of the invention [AA] comprises at least 10 amino acids, of which at least 70%, preferably at least 80%, more preferably at least 90% are identical to 10 consecutive amino acids of SEQ ID No. 1 and the position of the 7, respective 8 or 9 identical amino acids is also identical when compared to the respective positions of the 10 amino acids of SEQ ID No. 1.

In a preferred embodiment [AA] comprises at least 10 amino acids, of which 7, preferably 8, more preferably 9 are identical to 10 consecutive amino acids of column I of table 7.

In a further embodiment [AA] consists of 10 amino acids, of which 7, preferably 8, more preferably 9, more preferably 10 are identical compared to 10 consecutive amino acids of SEQ ID No. 1. Any possible 10 consecutive amino acids of SEQ ID No. 1 are listed in table 7.

Thus in this embodiment of the invention, [AA] consists of 10 amino acids, of which at least 70%, preferably at least 80%, more preferably at least 90%, more preferably 100% are identical to 10 consecutive amino acids of SEQ ID No. 1.

In a preferred embodiment [AA] consists of 10 amino acids, of which 7 amino acids, preferably 8 amino acids, more preferably 9 amino acids are identical compared to 10 consecutive amino acids of SEQ ID No. 1 and the position of the 7, respective 8 or 9 identical amino acids is also identical when compared to the respective position of the 10 amino acids of SEQ ID No. 1.

In a preferred embodiment [AA] consists of least 10 amino acids, of which 7, preferably 8, more preferably 9 are identical to 10 consecutive amino acids of column I of table 7.

In a further embodiment [AA] consists of at most 15, preferably at most 14, more preferably at most 12 amino acids, of which, preferably 8, more preferably 9, more preferably 10 amino acids, are identical to 10 consecutive amino acids of SEQ ID No. 1.

In a further embodiment [AA] consists of at most 15, preferably at most 14, more preferably at most 12 amino acids, of which 7 amino acids, preferably 8, more preferably 9 amino acids, are identical to 10 consecutive amino acids of SEQ ID No. 1 and the position of the 7, respective 8 or 9 amino acids is identical to the positions of respective amino acids of the 10 amino acids of SEQ ID No. 1. In this embodiment of the invention, also the position of the 7, respective 8 or 9 amino acids is identical when compared to the respective positions of 10 consecutive amino acids of SEQ ID No. 1.

[AA] Moiety: Undecapeptides

In a further embodiment [AA] comprises at least 11 amino acids, of which 8, preferably 9, more preferably 10, more preferably 11 amino acids are identical compared to 11 consecutive amino acids of SEQ ID No. 1. Any possible 11 consecutive amino acids of SEQ ID No. 1 are listed in Table 8.

Thus in this embodiment of the invention, [AA] comprises at least 11 amino acids, of which at least 72.7%, preferably at least 81.8%, more preferably at least 90.9%, more preferably 100% are identical to 11 consecutive amino acids of SEQ ID No. 1.

In a preferred embodiment [AA] comprises at least 11 amino acids, of which 8 amino acids, preferably 9 amino acids, more preferably 10 amino acids are identical compared to 11 consecutive amino acids of SEQ ID No. 1 and the position of the 8, respective 9 or 10 identical amino acids is also identical when compared to the respective positions of the 11 amino acids of SEQ ID No. 1.

Thus in this embodiment of the invention [AA] comprises at least 11 amino acids, of which at least 72.7%, preferably at least 81.8%, more preferably at least 90.9% are identical to 11 consecutive amino acids of SEQ ID No. 1 and the position of the 8, respective 9 or 10 identical amino acids is also identical when compared to the respective positions of the 11 amino acids of SEQ ID No. 1.

In a preferred embodiment [AA] comprises at least 11 amino acids, of which 8, preferably 9, more preferably 10 are identical to 11 consecutive amino acids of column I of table 8.

In a further embodiment [AA] consists of 11 amino acids, of which 8, preferably 9, more preferably 10, more preferably 11 are identical compared to 11 consecutive amino acids of SEQ ID No. 1. Any possible 11 consecutive amino acids of SEQ ID No. 1 are listed in table 8.

Thus in this embodiment of the invention, [AA] consists of 11 amino acids, of which at least 72.7%, preferably at least 81.8%, more preferably at least 90.9%, more preferably 100% are identical to 11 consecutive amino acids of SEQ ID No. 1.

In a preferred embodiment [AA] consists of 11 amino acids, of which 8 amino acids, preferably 9 amino acids, more preferably 10 amino acids are identical compared to 11 consecutive amino acids of SEQ ID No. 1 and the position of the 8, respective 9 or 10 identical amino acids is also identical when compared to the respective position of the 11 amino acids of SEQ ID No. 1.

In a preferred embodiment [AA] consists of least 11 amino acids, of which 8, preferably 9, more preferably 10 are identical to 11 consecutive amino acids of column I of table 8.

In a further embodiment [AA] consists of at most 15, preferably at most 14, more preferably at most 12 amino acids, of which 8, preferably 9, more preferably 10, more preferably 11 amino acids, are identical to 11 consecutive amino acids of SEQ ID No. 1.

In a further embodiment [AA] consists of at most 15, preferably at most 14, more preferably at most 12 amino acids, of which 8 amino acids, preferably 9, more preferably 10 amino acids, are identical to 11 consecutive amino acids of SEQ ID No. 1 and the position of the 8, respective 9 or 10 amino acids is identical to the positions of respective amino acids of the 11 amino acids of SEQ ID No. 1. In this embodiment of the invention, also the position of the 8, respective 9 or 10 amino acids is identical when compared to the respective positions of 11 consecutive amino acids of SEQ ID No. 1.

[AA] Moiety: Dodecapeptides

In a further embodiment [AA] comprises at least 12 amino acids, of which 8, preferably 9, more preferably 10, most preferably 11, most preferably 12 amino acids are identical compared to 12 consecutive amino acids of SEQ ID No. 1. Any possible 12 consecutive amino acids of SEQ ID No. 1 are listed in Table 9.

Thus in this embodiment of the invention, [AA] comprises at least 12 amino acids, of which at least 66.6%, preferably at least 75%, more preferably at least 83.3%, most preferably at least 91.6%, most preferably 100% are identical to 12 consecutive amino acids of SEQ ID No. 1.

In a preferred embodiment [AA] comprises at least 12 amino acids, of which 8 amino acids, preferably 9 amino acids, more preferably 10, most preferably 11 amino acids are identical compared to 12 consecutive amino acids of SEQ ID No. 1 and the position of the 8, respective 9 or 10 or 11 identical amino acids is also identical when compared to the respective positions of the 12 amino acids of SEQ ID No. 1.

Thus in this embodiment of the invention [AA] comprises at least 12 amino acids, of which at least 66.6%, preferably at least 75%, more preferably at least 83.3%, most preferably at least 91.6% are identical to 12 consecutive amino acids of SEQ ID No. 1 and the position of the 8, respective 9 or 10 or 11 identical amino acids is also identical when compared to the respective positions of the 12 amino acids of SEQ ID No. 1.

In a preferred embodiment [M] comprises at least 12 amino acids, of which 8, preferably 9, more preferably 10, most preferably 11 are identical to 12 consecutive amino acids of column I of table 9.

In a further embodiment [AA] consists of 12 amino acids, of which 8, preferably 9, more preferably 10, most preferably 11, most preferably 12 are identical compared to 12 consecutive amino acids of SEQ ID No. 1. Any possible 12 consecutive amino acids of SEQ ID No. 1 are listed in table 9.

Thus in this embodiment of the invention, [AA] consists of 12 amino acids, of which at least 66.6%, preferably at least 75%, more preferably at least 83.3%, most preferably at least 91.6%, most preferably 100% are identical to 12 consecutive amino acids of SEQ ID No. 1.

In a preferred embodiment [AA] consists of 12 amino acids, of which 8 amino acids, preferably 9 amino acids, more preferably 10 amino acids, most preferably 11 amino acids are identical compared to 12 consecutive amino acids of SEQ ID No. 1 and the position of the 8, respective 9 or 10 or 11 identical amino acids is also identical when compared to the respective position of the 12 amino acids of SEQ ID No. 1.

In a preferred embodiment [AA] consists of least 12 amino acids, of which 8, preferably 9, more preferably 10, most preferably 11 are identical to 12 consecutive amino acids of column I of table 9.

In a further embodiment [AA] consists of at most 15, preferably at most 14, more preferably at most 13 amino acids, of which 8, preferably 9, more preferably 10, most preferably 11, most preferably 12 amino acids, are identical to 12 consecutive amino acids of SEQ ID No. 1.

In a further embodiment [AA] consists of at most 15, preferably at most 14, more preferably at most 13 amino acids, of which 8 amino acids, preferably 9, more preferably 10, most preferably 11 amino acids, are identical to 12 consecutive amino acids of SEQ ID No. 1 and the position of the 8, respective 9 or 10 or 11 amino acids is identical to the positions of respective amino acids of the 12 amino acids of SEQ ID No. 1. In this embodiment of the invention, also the position of the 8, respective 9 or 10 or 11 amino acids is identical when compared to the respective positions of 12 consecutive amino acids of SEQ ID No. 1.

[AA] Moiety: Tridecapeptides

In a further embodiment [AA] comprises at least 13 amino acids, of which 9, preferably 10, more preferably 11, most preferably 12, most preferably 13 amino acids are identical compared to 13 consecutive amino acids of SEQ ID No. 1. Any possible 13 consecutive amino acids of SEQ ID No. 1 are listed in Table 10.

Thus in this embodiment of the invention, [AA] comprises at least 13 amino acids, of which at least 69.2%, preferably at least 76.9%, more preferably at least 84.6%, most preferably at least 92.3%, most preferably 100% are identical to 13 consecutive amino acids of SEQ ID No. 1.

In a preferred embodiment [AA] comprises at least 13 amino acids, of which 9 amino acids, preferably 10 amino acids, more preferably 11, most preferably 12 amino acids are identical compared to 13 consecutive amino acids of SEQ ID No. 1 and the position of the 9, respective 10, 11 or 12 identical amino acids is also identical when compared to the respective positions of the 13 amino acids of SEQ ID No. 1.

Thus in this embodiment of the invention [AA] comprises at least 13 amino acids, of which at least 69.2%, preferably at least 76.9%, more preferably at least 84.6%, most preferably at least 92.3% are identical to 13 consecutive amino acids of SEQ ID No. 1 and the position of the 9, respective 10 or 11 or 12 identical amino acids is also identical when compared to the respective positions of the 13 amino acids of SEQ ID No. 1.

In a preferred embodiment [AA] comprises at least 13 amino acids, of which 9, preferably 10, more preferably 11, most preferably 12 are identical to 13 consecutive amino acids of column I of table 10.

In a further embodiment [AA] consists of 13 amino acids, of which 9, preferably 10, more preferably 11, most preferably 12, more preferably 13 are identical compared to 13 consecutive amino acids of SEQ ID No. 1. Any possible 13 consecutive amino acids of SEQ ID No. 1 are listed in table 10.

Thus in this embodiment of the invention, [AA] consists of 13 amino acids, of which at least 69.2%, preferably at least 76.9%, more preferably at least 84.6%, most preferably at least 92.3%, most preferably 100% are identical to 13 consecutive amino acids of SEQ ID No. 1.

In a preferred embodiment [AA] consists of 13 amino acids, of which 9 amino acids, preferably 10 amino acids, more preferably 11 amino acids, most preferably 12 amino acids are identical compared to 13 consecutive amino acids of SEQ ID No. 1 and the position of the 9, respective 10 or 11 or 12 identical amino acids is also identical when compared to the respective position of the 13 amino acids of SEQ ID No. 1.

In a preferred embodiment [AA] consists of least 13 amino acids, of which 9, preferably 10, more preferably 11, most preferably 12 are identical to 13 consecutive amino acids of column I of table 10.

In a further embodiment [AA] consists of at most 15, preferably at most 14, of which 9, preferably 10, more preferably 11, most preferably 12, most preferably 13 amino acids, are identical to 13 consecutive amino acids of SEQ ID No. 1.

In a further embodiment [AA] consists of at most 15, preferably at most 14, of which 9 amino acids, preferably 10, more preferably 11, most preferably 12 amino acids, are identical to 13 consecutive amino acids of SEQ ID No. 1 and the position of the 9, respective 10 or 11 or 12 amino acids is identical to the positions of respective amino acids of the 13 amino acids of SEQ ID No. 1. In this embodiment of the invention, also the position of the 9, respective 10 or 11 or 12 amino acids is identical when compared to the respective positions of 13 consecutive amino acids of SEQ ID No. 1.

[AA] Moiety: Tetradecapeptides

In a further embodiment [AA] comprises at least 14 amino acids, of which 10, preferably 11, more preferably 12, most preferably 13, most preferably 14 amino acids are identical compared to 14 consecutive amino acids of SEQ ID No. 1. Any possible 14 consecutive amino acids of SEQ ID No. 1 are listed in Table 11.

Thus in this embodiment of the invention, [AA] comprises at least 14 amino acids, of which at least 71.4%, preferably at least 78.6%, more preferably at least 85.7%, most preferably at least 92.9%, most preferably 100% are identical to 14 consecutive amino acids of SEQ ID No. 1.

In a preferred embodiment [AA] comprises at least 14 amino acids, of which 10 amino acids, preferably 11 amino acids, more preferably 12, most preferably 13 amino acids are identical compared to 14 consecutive amino acids of SEQ ID No. 1 and the position of the 10, respective 11, 12 or 13 identical amino acids is also identical when compared to the respective positions of the 14 amino acids of SEQ ID No. 1.

Thus in this embodiment of the invention [AA] comprises at least 14 amino acids, of which at least 71.4%, preferably at least 78.6%, more preferably at least 85.7%, most preferably at least 92.9% are identical to 14 consecutive amino acids of SEQ ID No. 1 and the position of the 10, respective 11, 12 or 13 identical amino acids is also identical when compared to the respective positions of the 14 amino acids of SEQ ID No. 1.

In a preferred embodiment [AA] comprises at least 14 amino acids, of which 10, preferably 11, more preferably 12, most preferably 13 are identical to 14 consecutive amino acids of column I of table 11.

In a further embodiment [AA] consists of 14 amino acids, of which 10, preferably 11, more preferably 12, most preferably 13, most preferably 14 are identical compared to 14 consecutive amino acids of SEQ ID No. 1. Any possible 14 consecutive amino acids of SEQ ID No. 1 are listed in table 11.

Thus in this embodiment of the invention, [AA] consists of 14 amino acids, of which at least 71.4%, preferably at least 78.6%, more preferably at least 85.7%, most preferably at least 92.9%, most preferably 100% are identical to 14 consecutive amino acids of SEQ ID No. 1.

In a preferred embodiment [AA] consists of 14 amino acids, of which 10 amino acids, preferably 11 amino acids, more preferably 12 amino acids, most preferably 13 amino acids are identical compared to 14 consecutive amino acids of SEQ ID No. 1 and the position of the 10, respective 11 or 12 or 13 identical amino acids is also identical when compared to the respective position of the 14 amino acids of SEQ ID No. 1.

In a preferred embodiment [AA] consists of 14 amino acids, of which 10, preferably 11, more preferably 12, most preferably 13 are identical to 14 consecutive amino acids of column I of table 11.

In a further embodiment [AA] consists of at most 15, preferably at most 14, of which 10 amino acids, preferably 11, more preferably 12, most preferably 13, most preferably 14 amino acids, are identical to 14 consecutive amino acids of SEQ ID No. 1.

In a further embodiment [AA] consists of at most 15, preferably at most 14, of which 10 amino acids, preferably 11, more preferably 12, most preferably 13 amino acids, are identical to 14 consecutive amino acids of SEQ ID No. 1 and the position of the 10, respective 11, 12 or 13 amino acids is identical to the positions of respective amino acids of the 14 amino acids of SEQ ID No. 1. In this embodiment of the invention, also the position of the 109, respective 11 or 12 or 123 amino acids is identical when compared to the respective positions of 14 consecutive amino acids of SEQ ID No. 1.

[AA] Moiety: Pentadecapeptides

In a further embodiment [AA] consists of 15 amino acids, of which 10, preferably 11, more preferably 12, most preferably 13, most preferably 14, most preferably 15 amino acids are identical compared to 15 consecutive amino acids of SEQ ID No. 1. Any possible 15 consecutive amino acids of SEQ ID No. 1 are listed in Table 12.

Thus in this embodiment of the invention, [AA] consists of 15 amino acids, of which at least 66.6%, preferably at least 73.3%, more preferably at least 80%, most preferably at least 86.7%, most preferably at least 93.3%, most preferably 100% are identical to 15 consecutive amino acids of SEQ ID No. 1.

In a preferred embodiment [AA] consists of 15 amino acids, of which 10 amino acids, preferably 11 amino acids, more preferably 12 amino acids, most preferably 13, most preferably 14 amino acids are identical compared to 15 consecutive amino acids of SEQ ID No. 1 and the position of the 10, respective 11, 12, 13 or 14 identical amino acids is also identical when compared to the respective positions of the 15 amino acids of SEQ ID No. 1.

Thus in this embodiment of the invention [AA] consists of 15 amino acids, of which at least 66.6%, preferably at least 73.3%, more preferably at least 80%, most preferably at least 86.7%, most preferably at least 93.3% are identical to 15 consecutive amino acids of SEQ ID No. 1 and the position of the 10, respective 11, 12, 13 or 14 identical amino acids is also identical when compared to the respective positions of the 15 amino acids of SEQ ID No. 1.

In a preferred embodiment [AA] consists of 15 amino acids, of which 10, preferably 11, more preferably 12, most preferably 13, most preferably 14, most preferable 15 are identical to 15 consecutive amino acids of column I of table 12.

[AA] Moiety Pentapeptides

In a preferred embodiment [AA] comprises at least 5 amino acids, of which 4 amino acids, preferably 5 amino acids are identical compared to 5 consecutive amino acids of SEQ ID No. 1 and the position of the 4, respective 5 identical amino acids is also identical when compared to the respective positions of the 5 amino acids of SEQ ID No. 1. Any possible 5 consecutive amino acids of SEQ ID No. 1 are listed in Table 2.

Thus in this embodiment of the invention [AA] comprises at least 5 amino acids, of which at least 70%, preferably 100% are identical to 5 consecutive amino acids of SEQ ID No. 1 and the position of the 4, respective 5 identical amino acids is also identical when compared to the respective positions of the 5 amino acids of SEQ ID No. 1, preferably when compared to 5 consecutive amino acids of column I of table 2.

In a preferred embodiment [AA] consists of 5 amino acids, of which 4 amino acids, preferably 5 amino acids are identical compared to 5 consecutive amino acids of SEQ ID No. 1 and the position of the 4, respective 5 identical amino acids is also identical when compared to the respective position of the 6 amino acids of SEQ ID No. 1, preferably when compared to 5 consecutive amino acids of column I of table 2.

In a further embodiment [AA] consists of at most 15, preferably at most 10, more preferably at most 8 amino acids, of which 4 amino acids, preferably 5 amino acids, are identical to 5 consecutive amino acids of SEQ ID No. 1 and the position of the 4, respective 5 identical amino acids is also identical when compared to the respective positions of the 5 amino acids of SEQ ID No. 1, preferably when compared to 5 consecutive amino acids of column I of table 2.

In a further embodiment [AA] consists of at most 15, preferably at most 10, more preferably at most 8 amino acids, of which 4 amino acids, preferably 5 amino acids, are identical to 5 consecutive amino acids of SEQ ID No. 1 and the position of the 4, respective 5 amino acids is identical to the positions of respective amino acids of the 5 amino acids of SEQ ID no. 1, preferably when compared to 5 consecutive amino acids of column I of table 2.

R1 Moiety

The amino-terminal part of [AA] is linked via R1. R1 is chosen from the group consisting of a) —H b) is a linear saturated or unsaturated or branched saturated or unsaturated acyl group having 1 to 24 carbon atoms, which may be functionalised by a —OH, —SH, —COOH or —CONH$_2$ group, or c) a sterol or a sphingolipid group which is joined to the amino terminal part of [AA] via a bifunctional linker.

In embodiment a) the amino terminal is not substituted but consists of an amino group. It is within the scope of the invention that, in case R1=H, the oligopeptide of the invention can be protonated, and be present as salt, e.g. as chloride, bromide, fluoride or iodide.

In a preferred embodiment of the invention R1 is a linear saturated or unsaturated or branched saturated or unsaturated acyl group having 1 to 24 carbon atoms, preferably 1 to 6, preferably 1 to 12, preferably 10 to 20, more preferably 12 to 18 carbon atoms.

The radical R1 is preferably chosen from the group which is formed by acetyl ($CH_3$—CO—), ethanoyl ($CH_3$—$CH_2$—CO—), propionyl, butanoyl (=butyryl; $CH_3$—$(CH_2)_2$—CO—), decanoyl, palmitoyl ($CH_3$—$(CH_2)_{14}$—CO—), stearoyl ($CH_3$—$(CH_2)_{16}$—CO—), oleyl, lipoyl, linoleyl or conjugated linoleyl, particularly preferable the group is acetyl.

In one embodiment of the invention the acyl group can be further functionalised by one or more of the functional groups selected from the group consisting of —OH, —SH, —COOH and —CONH$_2$.

In one embodiment of the invention R1 is a sterol group. The sterol group can be selected from plant sterol or from sterol of animal origin.

Sterols in the context of the invention are steroids which only contain a hydroxyl group but no other functional groups at C-3. Formally, therefore, they are alcohols which is why this group of compounds is also referred to occasionally as sterols. In general, sterols contain from about 27 to about 30 carbon atoms and one double bond in the 5/6 position and occasionally in the 7/8, 8/9 or other positions. Sterols which may be used for the purposes of the invention are those obtained from natural products such as, for example, soya, rapeseed, sunflower, coconut, palm kernel and palm oil. Preferred sterols are sigmasterol, campesterol, sitosterol, brassicasterols, stigmasterol, D5 avenasterol, D7 avenasterol, ergosterol, citrostadienol, cholesterol, lanosterols, spongosterols, fungisterols, stellasterols, zymosterols and mixtures thereof and, more particularly, phytosterols based on ergosterols, avenasterols (D5 and D7 avenasterol), campesterols, stigmasterols, sitosterols, brassicasterols, citrosdandiols, sigmastandiols and mixtures thereof. Any other phytosterols known to the expert may also be used.

In a preferred embodiment the sterol group is selected from the group consisting of cholesterol, stigmasterol, sitosterol, or brassicasterol.

In one embodiment R1 is a sphingolipid, preferably sphingolipids are selected from the group consisting of sphingosine, phytosphingosine, dehydrosphingosine or deshuydrophytosphingosine.

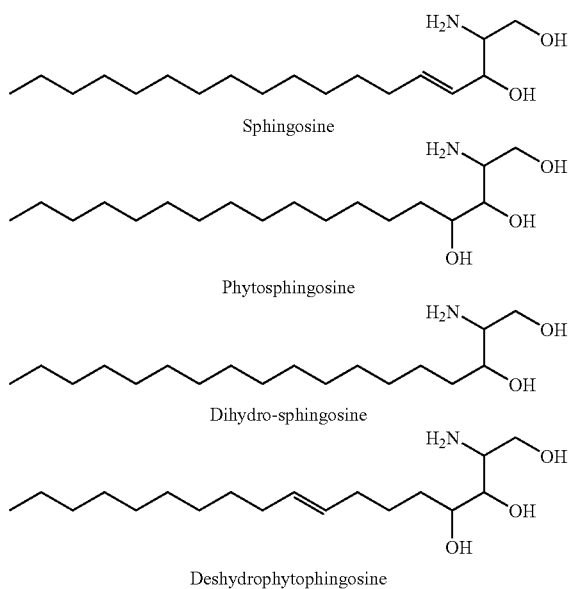

Sphingosine

Phytosphingosine

Dihydro-sphingosine

Deshydrophytophingosine

The sterol or the sphingolipide are linked to the oligopeptides using a bifunctional linker such as a diacid, for example succinic acid. The sterol hydroxyl group at C-3 can be linked via an ester bond to the bifunctional linker, with can be linked via an amide bond to the amino-terminal part of [AA]. The sphingolipid amino group at C-1 can be linked via an amide bond to the bifunctional linker, which can be linked via an amide bond to the amino-terminal part of [AA].

R2 Moiety

The carboxy terminal part of [AA] is linked via the C=O group of the carboxy terminal amino acids of [AA] and is chosen from the group which consists of
a) —OH
b) —$NH_2$ c) —a linear saturated or unsaturated or branched saturated or unsaturated alkoxy group having 1 to 24 carbon atoms, which may be functionalised by a —OH, —SH, —COOH or —$CONH_2$ group, or
d) a sterol or a spingolipid group.

In embodiment a) the carboxy terminal is not substituted but consists of a free carboxy group. It is within the scope of the invention that, in case R2=OH, the carboxy group of the oligopeptide of the invention can be deprotonated, and be present as salt, e.g. as potassium or sodium salt.

In embodiment b) the carboxy terminal is linked to an amino group. It is within the scope of the invention, that, in case R2=$NH_2$, the $NH_2$ group of can be protonated, and be present as a salt, e.g. as chloride, bromide, fluoride or iodide.

In a preferred embodiment of the invention R2 is a linear saturated or unsaturated or branched saturated or unsaturated alkoxy group having 1 to 24 carbon atoms, preferably 1 to 6, preferably 10 to 20, more preferably 12 to 18 carbon atoms.

In one embodiment of the invention the alkoxy group can be further functionalised by one or more of the functional groups selected from the group consisting of —OH, —SH, —COOH and —$CONH_2$.

In one embodiment of the invention R2 is a sterol. Suitable sterols are described under "R1 moieties". The sterol is linked to the C=O group of the carboxy terminus of [AA] via the 3-hydroxy group, thus resulting in an ester.

In one embodiment of the invention R1 is a sphingolipid. Suitable sphingolipids are described under "R2 moieties". The sphingolipid is linked to via its amino group to the terminal C=O group of the carboxy terminus of [AA], resulting in an amide.

Preferred Oligopeptides

Preferred oligopeptides according to the invention are oligopeptides with the structure of formula (I) wherein R1=a linear saturated or unsaturated or branched saturated or unsaturated acyl group having 1 to 24, preferably 1 to 12 carbon atoms, preferably 1 to 6, most preferably 2 (=acetyl), which may be functionalised by a —OH, —SH, —COOH or —$CONH_2$ group, Preferred according to the invention are oligopeptides of formula (I), wherein [AA] consists of a tetra peptide as specified in table 1, preferably column I of table 1 and R1 is selected from a linear saturated or unsaturated or branched saturated or unsaturated acyl group having 1 to 12 carbon atoms, preferably 1 to 6, most preferably 2 (=acetyl).

Especially preferred are oligopeptides of formula (I), wherein [AA] consist of a tetra-peptide selected from the group consisting of:

| | | |
|---|---|---|
| i) | Arg Arg Arg Pro; | (Seq. ID No. 2) |
| | Arg Arg Pro Arg; | (Seq. ID No. 3) |
| ii) | Arg Pro Pro Tyr; | (Seq. ID No. 6) |
| | Pro Pro Tyr Leu, preferably | (Seq. ID No. 7) |
| | Pro Pro Tyr Leu, | (Seq. ID No. 8) |
| iii) | Pro Tyr Leu Pro; | (Seq. ID No. 8) |
| | Tyr Leu Pro Arg; or | (Seq. ID No. 9) |
| iv) | Tyr Leu Pro Arg; | (Seq. ID No. 9) |
| | Leu Pro Arg Pro; | (Seq. ID No. 10) | and R1 is selected from a linear saturated or unsaturated or branched saturated or unsaturated acyl group having 1 to 12 carbon atoms, preferably 1 to 6, most preferably 2 (=acetyl).

Preferred according to the invention are oligopeptides of formula (I), wherein [AA] consists of a tetra peptide as specified in table 1, preferably column I of table 1 and R1 is selected from a linear saturated or unsaturated or branched saturated or unsaturated acyl group having 1 to 12 carbon atoms, preferably 1 to 6, most preferably 2 (=acetyl) and R2=—OH.

Especially preferred are oligopeptides of formula (I), wherein [AA] consist of a tetra-peptide selected from the group consisting of:

| | | |
|---|---|---|
| i) | Arg Arg Arg Pro; | (Seq. ID No. 2) |
| | Arg Arg Pro Arg; | (Seq. ID No. 3) |
| ii) | Arg Pro Pro Tyr; | (Seq. ID No. 6) |
| | Pro Pro Tyr Leu, preferably | (Seq. ID No. 7) |
| | Pro Pro Tyr Leu; | (Seq. ID No. 7) |
| iii) | Pro Tyr Leu Pro; | (Seq. ID No. 8) |
| | Tyr Leu Pro Arg; or | (Seq. ID No. 9) |
| iv) | Tyr Leu Pro Arg; | (Seq. ID No. 9) |
| | Leu Pro Arg Pro; | (Seq. ID No. 10) | and wherein R1=acetyl and R2=OH.

Preferred according to the invention are oligopeptides of formula (I), wherein [AA] is selected from the group consisting of Arg Arg Arg Pro Arg (Seq. ID No. 38); Arg Pro Pro Tyr Leu (Seq. ID No. 42); Pro Tyr Leu Pro Arg (Seq. ID No. 44); or Tyr Leu Pro Arg Pro (Seq. ID No. 45) and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] is selected from the group consisting of Arg Arg Arg Pro Arg (Seq. ID No. 38); Arg Pro Pro Tyr Leu (Seq. ID No. 42); Pro Tyr Leu Pro Arg (Seq. ID No. 38); or Tyr Leu Pro Arg Pro (Seq. ID No. 45); and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of a penta peptide as specified in table 2, preferably column I of table 2 and R1 is selected from a linear saturated or unsaturated or branched saturated or unsaturated acyl group having 1 to 12 carbon atoms, preferably 1 to 6, most preferably 2 (=acetyl) and R2=OH.

Preferred according to the invention are oligopeptides of formula (I), wherein [AA] is selected from the group consisting of Arg Arg Arg Pro Arg (Seq. ID No. 38); Arg Pro Pro Tyr Leu (Seq. ID No. 42); Pro Tyr Leu Pro Arg (Seq. ID No. 38); and Tyr Leu Pro Arg Pro (Seq. ID No. 45); and wherein R1=acteyl and R2=OH Preferred according to the invention are oligopeptides of formula (I), wherein [AA] consists of a hexa peptide as specified in table 3, preferably column I of table 3 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] is selected from the group consisting of Arg Arg Arg Pro Arg (Seq. ID No. 38); Arg Pro Pro Tyr Leu (Seq. ID No. 42); Pro Tyr Leu Pro Arg (Seq. ID No. 44); and Tyr Leu Pro Arg Pro (Seq. ID No. 45); and wherein R1=acteyl and R2=OH.

Preferred according to the invention are oligopeptides of formula (I), wherein [AA] consists of a hepta peptide as specified in table 4, preferably column I of table 4 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of a hepta peptide as specified in table 4, preferably column I of table 4 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of an octa peptide as specified in table 5, preferably column I of table 5 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of an octa peptide as specified in table 5, preferably column I of table 5 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of a nona peptide as specified in table 6, preferably column I of table 6 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of a nona peptide as specified in table 6, preferably column I of table 6 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of a deca peptide as specified in table 7, preferably column I of table 7 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of a deca peptide as specified in table 7, preferably column I of table 7 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of an undeca peptide as specified in table 8, preferably column I of table 8 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of an undeca peptide as specified in table 8, preferably column I of table 8 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of an dodeca peptide as specified in table 9, preferably column I of table 9 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of an dodeca peptide as specified in table 9, preferably column I of table 9 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of a trideca peptide as specified in table 10, preferably column I of table 10 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of a trideca peptide as specified in table 10, preferably column I of table 10 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of a tetradeca peptide as specified in table 11, preferably column I of table 11 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of a tetradeca peptide as specified in table 11, preferably column I of table 11 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

Preferred according to the invention are oligopeptides of formula (I), wherein [AA] consists of a pentadeca peptide as specified in table 12, preferably column I of table 11 and R1 is selected from a linear saturated or unsaturated or branched saturated or unsaturated acyl group having 1 to 24, preferably 1 to 12 carbon atoms, preferably 1 to 6, most preferably 2 (=acetyl).

Preferred according to the invention are oligopeptides of formula (I), wherein [AA] consists of a pentadeca peptide as specified in table 12, preferably column I of table 12 and R1 is selected from a linear saturated or unsaturated or branched saturated or unsaturated acyl group having 1 to 24, preferably 1 to 12 carbon atoms, preferably 1 to 6, most preferably 2 (=acetyl) and R2=—OH.

In a preferred embodiment of the invention n is at least 4, preferably at least 5; [AA] is selected from the amino acids no. 1 to 15 of SEQ ID No. 1, preferably from the amino acids no. 1-5, preferably from the amino acids 5-9, more preferably from the amino acids 6-9, preferably from the amino acids 7-11, more preferably from the amino acids 8-12 of SEQ ID No. 1.

Oligopeptides of Formula (II)

One embodiment of the invention is directed to the cosmetic use of oligopeptides of structure (II) for stimulating the renewal rate of skin and/or hair. They are preferably useful cosmetic preparations against the reduction in cell numbers in human skin or for stimulating and/or regenerating hair growth and against hair loss.

In one embodiment, the oligopeptide according to the formula (II) are especially useful for the cosmetic treatment of
l. human skin or hair ageing and/or
m. for preventing against ageing symptoms, such as wrinkles, and/or
n. decrease of the epidermal and dermal skin layers, and/or
o. alterations of the extracellular matrix and/or decrease in the renewal of epidermal
  and dermal cells and/or
p. modifications of the dermal epidermal junctions and/or
q. loss of elasticity and/or
r. hair damages and/or hair losses.

In one embodiment, the oligopeptides are preferably useful for
s. stimulation of the renewal rate of human skin and/or hair.

In a preferred embodiment, the oligopeptides are used for
t. producing cosmetic preparations which are effective for stimulating the production of mRNA and/or
u. for stimulation of matrix proteins such as collagen, elastin or proteoglycans and/or
v. for stimulation of syndecan-1 synthesis Oligopeptides of formula (II):

R1-[AA]$_n$-R2     (II)

wherein [AA] comprises at least 4 amino acids of which at least 3, are identical compared to 4 consecutive amino acids of SEQ ID No. 1 and/or wherein [AA] comprises at least 5 amino acids of which at least 4 are identical to 5 consecutive amino acids of SEQ ID No. 1
wherein n=4 to 15
wherein R1 is linked to the NH$_2$-group of the amino-terminal part of [AA] and is chosen from the group which is formed from
  a) —H
  b) a linear saturated or unsaturated or branched saturated or unsaturated acyl group having 1 to 24 carbon atoms, which may be functionalized by a —OH, —SH, —COOH or —CONH$_2$ group,
  c) a sterol or a spingolipid group which is joined to the amino terminal part of [AA] via a bifunctional linker
wherein R2 is linked to the C=O group of the carboxy-terminal part of [AA] and is chosen from the group which is formed from
  a) —OH,
  b) NH$_2$
  c) a linear saturated or unsaturated or branched saturated or unsaturated alkoxy group having 1 to 24 carbon atoms
  d) or a sterol or a sphingolipid group.

In this embodiment [AA] comprises at least 4 amino acids, of which at least 3 are identical compared to 4 consecutive amino acids of SEQ ID No. 1. Any possible 4 consecutive amino acids of SEQ ID No. 1 are listed in Table 1.

Thus in this embodiment of the invention, [AA] comprises at least 4 amino acids, of which at least 75%, preferably 100% are identical to 4 consecutive amino acids of SEQ ID No. 1.

In a preferred embodiment [AA] comprises at least 4 amino acids, of which at least 3 amino acids are identical compared to 4 consecutive amino acids of SEQ ID No. 1 and the position of the 3 identical amino acids is also identical when compared to the respective positions of the 4 amino acids of SEQ ID No. 1.

Thus in this embodiment of the invention [AA] comprises at least 4 amino acids, of which at least 75%, are identical to 4 consecutive amino acids of SEQ ID No. 1 and the position of the 3 identical amino acids is also identical when compared to the respective positions of the 4 amino acids of SEQ ID No. 1.

In following chart illustrates this embodiment of the invention. X and Y are further amino acids.

|  | Position No. | | | |
| --- | --- | --- | --- | --- |
|  | 1 | 2 | 3 | 4 |
| SEQ ID No. 1 | Arg | Arg | Arg | Pro |
| [AA] | Arg | X | Arg | Pro |
| [AA] | Arg | Arg | Arg | Y |

In a preferred embodiment [AA] comprises at least 4 amino acids, of which at least 3, are identical to 4 consecutive amino acids of column I of table 1.

In a further embodiment [AA] consists of 4 amino acids, of which at least 3 are identical compared to 4 consecutive amino acids of SEQ ID No. 1. Any possible 4 consecutive amino acids of SEQ ID No. 1 are listed in Table 1.

Thus in this embodiment of the invention, [AA] consists of 4 amino acids, of which at least 75%, preferably 100% are identical to 4 consecutive amino acids of SEQ ID No. 1.

In a preferred embodiment [AA] consists of 4 amino acids, of which at least 3 amino acids, are identical compared to 4 consecutive amino acids of SEQ ID No. 1 and the position of the 3 identical amino acids is also identical when compared to the respective position of the 4 amino acids of SEQ ID No. 1.

In this embodiment [AA] comprises at least 5 amino acids, of which at least 4 are identical compared to 5 consecutive amino acids of SEQ ID No. 1. Any possible 5 consecutive amino acids of SEQ ID No. 1 are listed in Table 2.

Thus in this embodiment of the invention, [AA] comprises at least 5 amino acids, of which at least 80%, preferably 100% are identical to 4 consecutive amino acids of SEQ ID No. 1.

In a preferred embodiment [AA] comprises at least 5 amino acids, of which at least 4 amino acids are identical compared to 5 consecutive amino acids of SEQ ID No. 1 and the position of the 4 identical amino acids is also identical when compared to the respective positions of the 5 amino acids of SEQ ID No. 1.

Thus in this embodiment of the invention [AA] comprises at least 5 amino acids, of which at least 80%, are identical to 5 consecutive amino acids of SEQ ID No. 1 and the position of the 4 identical amino acids is also identical when compared to the respective positions of the 5 amino acids of SEQ ID No. 1.

In a preferred embodiment [AA] comprises at least 5 amino acids, of which at least 4, are identical to 5 consecutive amino acids of column I of table 1.

In a further embodiment [AA] consists of 5 amino acids, of which at least 4 are identical compared to 5 consecutive amino acids of SEQ ID No. 1. Any possible 5 consecutive amino acids of SEQ ID No. 1 are listed in Table 2.

Thus in this embodiment of the invention, [AA] consists of 5 amino acids, of which at least 80%, preferably 100% are identical to 5 consecutive amino acids of SEQ ID No. 1.

In a preferred embodiment [AA] consists of 5 amino acids, of which at least 4 amino acids, are identical compared to 5 consecutive amino acids of SEQ ID No. 1 and the position of the 4 identical amino acids is also identical when compared to the respective position of the 5 amino acids of SEQ ID No. 1.

Oligopeptides

A further embodiment of the invention relates to oligopeptides of formula (II)

$$R1\text{-}[AA]_n\text{-}R2 \tag{II}$$

wherein [AA] comprises at least 4 amino acids of which at least 3, are identical compared to 4 consecutive amino acids of SEQ ID No. 1 and/or wherein [AA] comprises at least 5 amino acids of which at least 4 are identical to 5 consecutive amino acids of SEQ ID No. 1 wherein n=4 to 15, preferably n=4, n=5.

wherein R1 is linked to the $NH_2$-group of the amino-terminal part of [AA] and is chosen from the group which is formed from a) —H, b) a linear saturated or unsaturated or branched saturated or unsaturated acyl group having 1 to 24 carbon atoms, which may be functionalized by a —OH, —SH, —COOH or —$CONH_2$ group, c) a sterol or a spingolipid group which is joined to the amino terminal part of [AA] via a bifunctional linker wherein R2 is linked to the C=O group of the carboxy-terminal part of [AA] and is chosen from the group which is formed from a) —OH, b) —$NH_2$ c) a linear saturated or unsaturated or branched saturated or unsaturated alkoxy group having 1 to 24 carbon atoms d) or a sterol or a sphingolipid group with the proviso that if R1 is —H, R2 is not —OH; or that if R2 is —OH, R1 is not —H; and with the proviso that [AA] is not Arg Lys Pro Arg (Seq. ID No. 367), Phe-Tyr-Arg-Pro-Arg (Seq. ID No. 372), Ala-Arg-Asp-Pro-Arg. ID No. 373).

Surprisingly it has been found that these oligopeptides can be used in cosmetic compositions, preferably for stimulating the renewal rate of skin and/or hair.

Synthesis of Oligopeptides

The oligopeptides according to the invention can be obtained by chemical or enzymatic synthesis or by controlled hydrolysis of natural proteins of microorganisms, plants or animals which contain the sequence as in SEQ ID No. 1. The hydrolysate comprising the sequence as in SEQ ID No. 1 or at least one fragment of at least four amino acids of SEQ ID No. 1 or the position 1-15 or 1-5, or 5-9, or 6-9, or 7-11, or 8-12 of SEQ ID No. 1 obtained by hydrolysis of natural proteins can be purified by known techniques such as membrane filtration, chromatography or immunoprecipitation. The oligopeptides can also be produced by microorganisms, which either naturally form the oligopeptides, or have possibly been genetically modified or are manipulated in some other way during fermentation through fermentation conditions such that they form the oligopeptides according to the invention. The amino acids can either occur in the L, the D, or the DL form in the peptide fragment.

Cosmetic Compositions

One embodiment of the invention is directed to cosmetic compositions comprising at least one oligopeptide of the structure of formula (I).

The oligopeptide are preferably used in a concentration from 0.05 to 500 ppm, preferably from 0.5 to 100 ppm.

The oligopeptides are preferably dissolved in one or more solvents which are approved for cosmetic preparations, such as, for example, water, glycerin, propylene glycol, butylene glycol, ethoxylated or propoxylated diglycols, ethanol, propanol, isopropanol or mixtures of said solvents. Furthermore, it is possible to use the oligopeptides solubilized in liposomes or adsorbed to organic polymers or similar material which is acceptable for topical application.

Besides the solvents, further auxiliaries and additives may also be present in the preparations which are used according to the invention.

Cosmetic and/or Dermatological Preparations

The oligopeptides and the cosmetic uses according to the invention can serve for producing cosmetic preparations, such as, for example, hair shampoos, hair lotions, foam baths, shower baths, creams, gels, lotions, alcoholic and aqueous/alcoholic solutions, emulsions, wax/fat masses, stick preparations, powders or ointments. These preparations can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, tyrosine inhibitors (depigmentation agents), hydrotropes, solubilizers, preservatives, perfume oils, dyes and the like.

Surfactants

Surface-active substances which may be present are anionic, nonionic, cationic and/or amphoteric or zwitterionic surfactants, the content of which in the compositions is usually about 1 to 70% by weight, preferably 5 to 50% by weight and in particular 10 to 30% by weight. Typical examples of anionic surfactants are soaps, alkylbenzenesulphonates, alkanesulphonates, olefinsulphonates, alkyl ether sulphonates, glycerol ether sulphonates, α-methyl ester sulphonates, sulpho fatty acids, alkyl sulphates, alkyl ether sulphates, glycerol ether sulphates, fatty acid ether sulphates, hydroxy mixed ether sulphates, monoglyceride (ether) sulphates, fatty acid amide (ether) sulphates, mono- and dialkyl sulphosuccinates, mono- and dialkyl sulphosuccinamates, sulphotriglycerides, amide soaps, ether carboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants comprise polyglycol ether chains, these can have a conventional homologue distribution, but preferably have a narrowed homologue distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homologue distribution, but preferably have a narrowed homologue distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric and zwitterionic surfactants are alkylbetaines, alkylamidobetaines, aminopropionates, aminoglycinates, imidazoliniumbetaines and sulphobetaines. The specified surfactants are exclusively known compounds. Typical examples of particularly suitable mild, i.e. particularly skin-compatible, surfactants are fatty alcohol polyglycol ether sulphates, monoglyceride sulphates, mono- and/or dialkyl suiphosuccinates, fatty acid isethionates, fatty acid sarcosinates, fatty acid taurides, fatty acid glutamates, α-olefinsulphonates, ether carboxylic acids, alkyl oligoglucosides, fatty acid glucamides, alkylamidobetaines, amphoacetals and/or protein fatty acid condensates, the latter preferably being based on wheat proteins.

Oil Bodies

Suitable oil bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkyl hydroxycarboxylic acids with linear or branched $C_6$-$C_{22}$-fatty alcohols (cf. DE 19756377 A1), in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, squalane, squalene or dialkylcyclohexanes.

Emulsifiers

Suitable emulsifiers are, for example, nonionogenic surfactants from at least one of the following groups:

addition products of from 2 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and the ethoxylated analogues thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

Ethylene Oxide Addition Products

The addition products of ethylene oxide and/or of propylene oxide to fatty alcohols, fatty acids, alkylphenols or to castor oil are known, commercially available products. These are homologue mixtures whose average degree of alkoxylation corresponds to the ratio of the amounts of substance of ethylene oxide and/or propylene oxide and substrate with which the addition reaction is carried out. $C_{12/18}$-fatty acid mono- and diesters of addition products of ethylene oxide to glycerol are known as refatting agents for cosmetic preparations.

Alkyl and/or Alkenyl Oligoglycosides

Alkyl and/or alkenyl oligoglycosides, their preparation and their use are known from the prior art. They are prepared, in particular, by reacting glucose or oligo-saccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homologue distribution customary for such technical-grade products.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxy-stearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide to said sorbitan esters.

Polyglycerol Esters

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers

Furthermore, zwitterionic surfactants can be used as emulsifiers. The term "zwitterionic surfactants" refers to those surface-active compounds which carry at least one quaternary ammonium group and at least one carboxylate and one sulphonate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group, contain at least one free amino group and at least one —COOH or —$SO_3H$ group in the molecule and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acyl-sarcosine. Finally, cationic surfactants are also suitable as emulsifiers, those of the ester quat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which are founded from fatty acids, glycerol, phosphoric acid and choline by esterification. Lecithins are thus also often as phosphatidylcholines (PC) in the specialist world. Examples of natural lecithins which may be mentioned are the cephalins, which are also referred to as phosphatidic acids and constitute derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines or sphingolipids are also suitable.

Pearlescent Waxes

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Consistency Regulators and Thickeners

Suitable consistency regulators are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose, hydroxyethylcellulose and hydroxypropylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS 5PC (Rheox), which is a mixture of cyclopentasiloxane, disteardimonium hectorite and propylene carbonate, have also proven to be particularly effective. Also suitable are surfactants, such as, for example, ethoxylated fatty acid glycerides, esters of fatty acids with polyols such as, for example, pentaerythritol or trimethylolpropane, fatty alcohol ethoxylates having a narrowed homologue distribution or alkyl oligoglucosides, and electrolytes such as sodium chloride and ammonium chloride.

Superfatting Agents

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Stabilizers

Stabilizers which can be used are metal salts of fatty acids, such as, for example, magnesium, aluminium and/or zinc stearate or ricinoleate.

Polymers

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxy-propyl hydrolyzed collagen (Lamequat®L/Grünau), quaternized wheat polypeptides, polyethyleneimine, cationic silicone polymers, such as, for example, amodimethicones, copolymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylamino-ethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Silicone Compounds

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

UV Photoprotective Filters

UV photoprotective factors are, for example, to be understood as meaning organic substances (photoprotective filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor or 3-benzylidenenorcamphor and derivatives thereof, e.g. 3-(4-methyl benzylidene)camphor;
4-aminobenzoic acid derivatives, preferably 2-ethylhexyl 4-(dimethylamino)benzoate, 2-octyl 4-(dimethylamino) benzoate and amyl 4-(dimethylamino)benzoate;
esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);
esters of salicylic acid, preferably 2-ethylhexyl salicylate, 4-isopropylbenzyl salicylate, homomethyl salicylate;
derivatives of benzophenone, preferably 2-hydroxy-4-methoxybenzophenone, 2-hydroxy-4-methoxy-4'-methylbenzophenone, 2,2'-dihydroxy-4-methoxybenzophenone;
esters of benzalmalonic acid, preferably di-2-ethylhexyl 4-methoxybenzalmalonate;
triazine derivatives, such as, for example, 2,4,6-trianilino(p-carbo-2'-ethyl-1'-hexyloxy)-1,3,5-triazine and octyltriazone or dioctylbutamidotriazone (Uvasorb® HEB);
propane-1,3-diones, such as, for example, 1-(4-tert-butylphenyl)-3-(4'-methoxyphenyl)propane-1,3-dione;
ketotricyclo(5.2.1.0)decane derivatives.

Suitable water-soluble substances are:
2-phenylbenzimidazole-5-sulphonic acid and the alkali metal, alkaline earth metal, ammonium, alkylammonium, alkanolammonium and glucammonium salts thereof;
sulphonic acid derivatives of benzophenones, preferably 2-hydroxy-4-methoxybenzophenone-5-sulphonic acid and its salts;
sulphonic acid derivatives of 3-benzylidenecamphor, such as, for example, 4-(2-oxo-3-bornylidenemethyl)benzenesulphonic acid and 2-methyl-5-(2-oxo-3-bornyl-idene)sulphonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UV-A and UV-B filters can of course also be used in mixtures. Particularly favourable combinations consist of the derivatives of benzoylmethane, e.g. 4-tert-butyl-4'-methoxydibenzoylmethane (Parsol® 1789) and 2-ethylhexyl 2-cyano-3,3-phenyl-cinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide.

Biogenic Active Ingredients and Antioxidants

Biogenic active ingredients are understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prunus extract, bambara nut extract and vitamin complexes.

Antioxidants interrupt the photochemical reaction chain which is triggered when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), auro-thioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof)

and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Deodorants and Antimicrobial Agents

Cosmetic deodorants counteract, mask or remove body odours. Body odours arise as a result of the effect of skin bacteria on apocrine perspiration, with the formation of degradation products which have an unpleasant odour. Accordingly, deodorants comprise active ingredients which act as antimicrobial agents, enzyme inhibitors, odour absorbers or odour masking agents.

Antimicrobial Agents

Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl) urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxy-ethanol, glycerol monocaprate, glycerol monocaprylate, glycerol monolaurate (GML), diglycerol monocaprate (DMC), salicylic acid N-alkylamides, such as, for example, N-octylsalicylamide or N-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odour. Other substances which are suitable esterase inhibitors are sterol sulphates or phosphates, such as, for example, lanosterol, cholesterol, campesterol, stigmasterol and sitosterol sulphate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers

Suitable odour absorbers are substances which are able to absorb and largely retain odour-forming compounds. They lower the partial pressure of the individual components, thus also reducing their rate of diffusion. It is important that in this process perfumes must remain unimpaired. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclo-hexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxy-acetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants

Antiperspirants reduce the formation of perspiration by influencing the activity of the eccrine sweat glands, thus counteracting underarm wetness and body odor. Aqueous or anhydrous formulations of antiperspirants typically comprise the following ingredients:
astringent active ingredients,
oil components,
nonionic emulsifiers,
coemulsifiers,
consistency regulators,
auxiliaries, such as, for example, thickeners or complexing agents and/or
nonaqueous solvents, such as, for example, ethanol, propylene glycol and/or glycerol.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be:
anti-inflammatory, skin-protective or perfumed essential oils,
synthetic skin-protective active ingredients and/or
oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Antidandruff Active Ingredients

Suitable antidandruff active ingredients are piroctone olamine (1-hydroxy-4-methyl-6-(2,4,4-trimythylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulphide, sulphur colloidal, sulphur polyethylene glycol sorbitan monooleate, sulphur ricinole polyethoxylate, sulphur tar distillates, salicylic acid (or in combination with hexachlorophene), undecylenic acid monoethanolamide sulpho-succinate Na salt, Lamepon® UD (protein undecylenic acid condensate), zinc pyrithione, aluminium pyrithione and magnesium pyrithione/dipyrithione magnesium sulphate.

Swelling Agents

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

Insect Repellents

Suitable insect repellents are N,N-diethyl-m-toluamide, 1,2-pentanediol or ethyl butylacetylaminopropionate.

Self-Tanning Agents and Depigmentation Agents

A suitable self-tanning agent is dihydroxyacetone. Suitable tyrosine inhibitors, which prevent the formation of melanin and are used in depigmentation agents, are, for example, arbutin, ferulic acid, kojic acid, coumaric acid and ascorbic acid (vitamin C).

Hydrotropic Agents

To improve the flow behaviour, it is also possible to use hydrotropic agents, such as, for example, ethanol, isopropyl alcohol, or polyols. Polyols which are suitable here preferably have 2 to 15 carbon atoms and at least two hydroxyl groups. The polyols can also contain further functional groups, in particular amino groups, or be modified with nitrogen. Typical examples are
glycerol;
alkylene glycols, such as, for example, ethylene glycol, diethylene glycol, propylene glycol, butylene glycol, hexylene glycol, and polyethylene glycols with an average molecular weight of from 100 to 1 000 daltons;
technical-grade oligoglycerol mixtures with a degree of self-condensation of from 1.5 to 10, such as, for example, technical-grade diglycerol mixtures with a diglycerol content of from 40 to 50% by weight;
methylol compounds, such as, in particular, trimethylolethane, trimethylolpropane, trimethylolbutane, pentaerythritol and dipentaerythritol;
lower alkyl glucosides, in particular those having 1 to 8 carbon atoms in the alkyl radical, such as, for example, methyl and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcohol amines, such as diethanolamine or 2-amino-1,3-propanediol.

Preservatives

Suitable preservatives are, for example, phenoxy ethanol, formaldehyde solution, parabens, pentanediol or sorbic acid, and the silver complexes known under the name Surfacins®, and also the other classes of substance listed in Annex 6, Part A and B of the Cosmetics Directive.

Perfume Oils and Aromas

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamon, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable aromas are, for example, peppermint oil, spearmint oil, anise oil, star anise oil, caraway oil, eucalyptus oil, fennel oil, lemon oil, wintergreen oil, oil of cloves, menthol and the like.

Dyes

Dyes which can be used are the substances which are approved and suitable for cosmetic purposes, as are summarized, for example, in the publication "Kosmetische Färbemittel" [Cosmetic Colorants] from the Farbstoffkommission der Deutschen Forschungsgemeinschaft [Dyes Commission of the German Research Council], Verlag Chemie, Weinheim, 1984, pp. 81-106. Examples are cochineal red A (C.I.16255), patent blue V (C.I.42051), indigotin (C.I.73015), chlorophyllin (C.I.75810), quinoline yellow (C.I.47005), titanium dioxide (C.I.77891), indanthrene blue RS (C.I.69800) and madder lake (C.I.58000). As a luminescent dye, it is also possible for luminol to be present. These dyes are customarily used in concentrations of from 0.001 to 0.1% by weight, based on the total mixture.

The total amount of auxiliaries and additives can be 1 to 50% by weight, preferably 5 to 40% by weight, based on the compositions. The compositions can be prepared by customary cold or hot processes; preference is given to using the phase-inversion temperature method.

EXAMPLES

Effects on the Growth of Human Primary Keratinocytes

The aim of this test was to analyse the revitalizing and regenerating activities of oligpopeptides according to the invention on human keratinocyte cultures in vitro.

Human keratinocytes were obtained by trypsinization of skin biopsies. They were incubated in standard medium for cell cultures with foetal calf serum (FCS) and growth factors (EGF 10 ng/ml). After cultivation for 2 days at 37° C. and a $CO_2$ content of 5%, the medium was replaced by standard medium with varying concentrations of peptides. After a further incubation of 4 or 5 days at 37° C. and a $CO_2$ content of 5%, the number of living cells was determined by determining the cellular DNA content using an ethidium bromide fluorescent sample. The fluorescence was determined using a fluorimeter (excitation at 538 nm and emission at 590 nm). The foetal calf serum forms a positive control because it comprises many growth factors, such as, for example, IGF (insulin-like growth factor) and PDGF (platelet derived growth factor).

The results are shown in Table 1 and 2 as the average value from 3 assays in triplicate in % based on a control in which the standard medium comprised no additives.

TABLE 1

| Oligopeptide | Concentration % (w/v) | DNA after culture for 4-5 days |
| --- | --- | --- |
| Control | — | 100 |
| Foetal calf serum | 1 | 117 +/− 13 |
| Example 1 | 0.001 | 124 +/− 15 |
| Arg-Arg-Arg-Pro-Arg-Pro-Pro-Tyr-Leu-Pro-Arg-Pro-Arg-Pro-Pro (Seq. ID No. 341) | 0.003 | 131 +/− 11 |
| Example 2 | 0.001 | 119 +/− 6 |
| Arg-Arg-Arg-Pro-Arg (Seq. ID No. 38) | 0.003 | 126 +/− 8 |
| Example 3 | 0.001 | 97 +/− 1 |
| Arg-Pro-Pro-Tyr-Leu (Seq. ID No. 42) | 0.003 | 118 +/− 10 |
| Example 4 | 0.001 | 150 +/− 26 |
| Pro-Pro-Tyr-Leu (Seq. ID No. 7) | 0.003 | 166 +/− 7 |
| Example 5 | 0.001 | 118 +/− 3 |
| Pro-Tyr-Leu-Pro-Arg (Seq. ID No. 44) | 0.003 | 112 +/− 5 |
| Example 6 | 0.001 | 110 +/− 6 |
| Tyr-Leu-Pro-Arg-Pro (Seq. ID No. 45) | 0.003 | 146 +/− 24 |

TABLE 2

| Peptide | Concentration % (w/v) | DNA after culture for 3 days |
| --- | --- | --- |
| Control | — | 100 |
| Foetal calf serum | 1 | 126 +/− 17 |
| Example 7 | 0.00005 | 136 +/− 13 |
| N-Palmitoyl-Pro-Pro-Tyr-Leu (Seq. ID No. 374) | 0.00015 | 135 +/− 8 |

The oligopeptide consisting of 15 consecutive amino acids of SEQ ID No. 1 (Example 1, R1=H, R2=OH) as well as the oligopeptides consisting of 5 consecutive amino acids, which are identical to 5 consecutive amino acids of SEQ ID No. 1 (examples 2, 3, 5 and 6, R1=H, R2=OH) as well as the oligopeptides consisting of 4 consecutive amino acids, which are identical to 4 consecutive amino acids of SEQ ID No. 1 (example 4, R1=H, R2=OH) stimulate the growth of human keratinocytes cultivated from biopsies of adult subjects. The activity can still be detected after 5 days even without changing the cell culture medium.

The same is true for an oligopeptide according to formula (I), wherein [AA] is Pro-Pro-Tyr-Leu (Seq. ID No. 7), R1 is Palmitoyl and R2 is OH (=example 7).

Stimulation of the Synthesis of Syndecan-1 on Human Keratinocytes

Monoclonal antibody anti-syndecan-1 and secondary antibody FITC conjugated were obtained from TEBU, Le Perray en Yvelines and BIO-RAD, Marnes-la-Coquette; KGF (Keratinocyte Growth Factor) (positive control) was obtained from SIGMA, L'Isle d'Abeau Chesnes.

Human keratinocytes were seeded in DMEM standard medium for 2 days at 37° C., $CO_2$=5%. Then, N-Acetyl-Pro-Pro-Tyr-Leu (Seq. ID No. 375) or positive control KGF are introduced and after 5 days of incubation at 37° C., $CO_2$=5%, the synthesis of syndecan-1 was evaluated on glass slides by immunocytochemistry. Quantification of the staining was carried out by image analysis.

The results are shown in table 3 as the mean of the sum±SEM of the product of number of pixels by green detected values (arbitrary unit).

TABLE 3

| | Control without treatment | Treated with KGF at 10 ng/ml | Treated with N-Acetyl-Pro-Pro-Tyr-Leu | |
|---|---|---|---|---|
| | (DMEM) | (positive control) | 1 µg/ml | 3 µg/ml |
| Sum of product of number of pixel by green detected values for syndecan-1 (arbitrary unit) | 1545 $10^3$ ± 374 $10^3$ | 2408 $10^3$ ± 549 $10^3$ | 2791 $10^3$ ± 573 $10^3$ | 3344 $10^3$ ± 359 $10^3$(*) |

Statistics:
Test PLSD of Fisher
(*)control, p < 0.01

Without treatment, human keratinocytes in culture expressed a small amount of syndecan-1. The treatment with the positive control KGF has induced an increase of syndecan-1 expression in the keratinocytes culture.

The oligopeptide according to formula (I) wherein [AA] is Pro-Pro-Tyr-Leu (Seq. ID No. 7), R1 is Acetyl, and R2 is OH stimulates the synthesis of syndecan-1 in human keratinocytes cultivated from biopsies of adult subjects.

| Cosmetic emulsion | |
|---|---|
| Trade Name [INCI] | % by weight |
| Emulgade SE-PF[2] [Glyceryl Stearate (and) Ceteareth-20 (and) Ceteareth-12 (and) Cethaeryl Alcohol (and) Cetyl palmitate] | 6.00 |
| Lanette O[2] [Cetearyl Alcohol] | 2.50 |
| Cegesoft C24[2] [Ethyl hexyl palmitate] | 6.00 |
| Cetiol PGL[2] [Hexyldecanol (and) Hexyldecyl laurate] | 5.00 |
| Myritol 312[2] [Caprylic/Capric Trigylceride] | 3.00 |
| DC 200-50cts[3] [Dimethicone] | 1.00 |
| Deionized water | add 100 |
| Keltrol T[4] [Xantham Gum] | 0.20 |
| Elestab 50J[1] | 0.40 |

| Cosmetic emulsion -continued | |
|---|---|
| Trade Name [INCI] | % by weight |
| [Chlorphenesin (and) Methylparaben] | |
| Glycerine | 4.00 |
| Carbopol 980[5] 2% [Carbomer] | 15.00 |
| NaOH 10% | 0.60 |
| Perfume Champaline G10415611[6] | 0.10 |
| N-Acetyl-Pro-Pro-Tyr-Leu-OH | 0.0003 |

| Cosmetic fluid serum | |
|---|---|
| Trade Name | % by weight |
| Deionized Water | add 100 |
| Elestab 50J[1] [Chlorphenesin (and) Methylparaben] | 0.35 |
| H-Tyr-Leu-Pro-Arg-Pro-OH | 0.001 |
| Keltrol CGT[4] [Xantham gum] | 0.10 |
| Cosmedia SP[2] [Sodium Polyacrylate] | 0.25 |

Suppliers
[1]Laboratoires Sérobiologiques
[2]Cognis
[3]Dow Corning
[4]Kelco
[5]Noveon
[6]Robertet SEQ ID No. 1 consisting of 39 amino acids:

(=1) Arg Arg Arg Pro Arg Pro Pro Tyr Leu Pro Arg

Pro Arg Pro Pro Pro Phe Phe Pro Pro Arg Leu Pro

Pro Arg Ile Pro Pro Glu Phe Pro Pro Arg Phe Pro

Pro Arg Phe Pro (=39)

The invention claimed is:

1. A cosmetic composition comprising oligopeptides with the structure of formula (I)

$$R1-[AA]_n-R2 \quad (I)$$

wherein [AA] comprises at least 4 consecutive amino acids, which are identical compared to 4 consecutive amino acids of SEQ ID No. 1, wherein n is the total number of amino acids in the oligopeptide, wherein n=4, wherein R1 is linked to the amino-terminal part of [AA] and is selected from the group consisting of
 d) —H,
 e) a linear saturated or unsaturated or branched saturated or unsaturated acyl group having 1 to 24 carbon atoms, wherein said acyl group is optionally functionalised by a —OH, —SH, —COOH or —CONH$_2$ group, and
 f) a sterol or a sphingolipid group which is joined to the amino terminal part of [AA] via a bifunctional linker, and wherein R2 is linked to the C═O group of the carboxy terminal part of [AA] and is selected from the group consisting of
 a) —OH,
 b) —NH$_2$,
 c) is a linear saturated or unsaturated or branched saturated or unsaturated alkoxy group having 1 to 24 carbon atoms, wherein said acyl group is optionally functionalised by a —OH, —SH, —COOH or CONH$_2$ group, and
 d) a sterol or a sphingolipid group.

2. The composition of claim 1, wherein [AA] comprises at least 4 consecutive amino acids identical to amino acids no. 1 to 15 of SEQ ID No. 1.

3. The composition of claim 1, wherein R1=H or a linear saturated or unsaturated or branched saturated or unsaturated acyl group having 1 to 12 carbon atoms.

4. The composition of claim 1, wherein the oligopeptides are present in a concentration of from 0.05 to 500 ppm.

5. A cosmetic composition comprising oligopeptides with the structure of formula (I)

$$R1-[AA]_n-R2 \quad (I)$$

wherein [AA] comprises at least 4 consecutive amino acids, which are identical compared to 4 consecutive amino acids of SEQ ID No. 1, wherein n is the total number of amino acids in the oligopeptide, wherein n=4, wherein R1 is linked to the amino-terminal part of [AA] and is selected from the group consisting of
 i. —H,
 ii. a linear saturated or unsaturated or branched saturated or unsaturated acyl group having 1 to 24 carbon atoms, which may be functionalised by a —OH, —SH, —COOH or —CONH$_2$ group, or
 iii. a sterol or a sphingolipid group which is joined to the amino terminal part of [AA] via a bifunctional linker, wherein R2 is linked to the C═O group of the carboxy terminal part of [AA] and is selected from the group consisting of
 a) —OH,
 b) —NH$_2$,
 c) a linear saturated or unsaturated or branched saturated or unsaturated alkoxy group having 1 to 24 carbon atoms, which may be functionalised by a —OH, —SH, —COOH or —CONH$_2$ group, and
 d) a sterol or a sphingolipid group, with the proviso that if R1 is —H, R2 is not —OH; or that if R2 is —OH, R1 is not —H; and with the further proviso that if R1 is —H, R2 is selected from the group consisting of
 b) —NH$_2$,
 c) a linear saturated or unsaturated or branched saturated or unsaturated alkoxy group having 2 to 24 carbon atoms, or
 d) a sterol or a sphingolipid group.

6. The composition of claim 1, wherein said oligopeptides are present in an amount effective to stimulate the growth of human keratinocytes in-vitro.

7. The composition of claim 1, wherein said at least 4 consecutive amino acids is Pro-Pro-Tyr-Leu (SEQ ID No. 7).

8. A method for strengthening the cutaneous barrier of human skin comprising contacting the skin with the cosmetic composition of claim 1 in an amount effective to stimulate the growth and differentiation of human keratinocytes.

9. A method for strengthening the cutaneous barrier of human skin comprising contacting the skin with the cosmetic composition of claim 1 in an amount effective to stimulate syndecan-1 synthesis.

10. A method for strengthening firmness, epidermal cohesion, and dermo-epidermal junction of human skin comprising contacting the skin with the cosmetic composition of claim 1 in an amount effective to stimulate the growth and differentiation of human keratinoctyes.

11. A method for strengthening firmness, epidermal cohesion, and dermo-epidermal junction of human skin comprising contacting the skin with the cosmetic composition of claim 1 in an amount effective to stimulate syndecan-1 synthesis.

* * * * *